US012797481B2

(12) United States Patent
Wang et al.

(10) Patent No.: US 12,797,481 B2
(45) Date of Patent: Nov. 17, 2026

(54) DEVELOPMENT OF DRUG THERAPEUTIC AGENT CONTAINING ADAPTOR AND USE THEREOF

(71) Applicant: BEIJING TIANNUOJIANCHENG PHARMA TECH CO., LTD., Beijing (CN)

(72) Inventors: Ying Wang, Chengdu (CN); Gang Xu, Chengdu (CN); Bo Chen, Chengdu (CN)

(73) Assignee: Beijing Tiannuojiancheng Pharma Tech Co., Ltd., Beijing (CN)

( * ) Notice: Subject to any disclaimer, the term of this patent is extended or adjusted under 35 U.S.C. 154(b) by 714 days.

(21) Appl. No.: 18/023,332

(22) PCT Filed: Aug. 26, 2021

(86) PCT No.: PCT/CN2021/114847

§ 371 (c)(1),
(2) Date: Feb. 24, 2023

(87) PCT Pub. No.: WO2022/042661

PCT Pub. Date: Mar. 3, 2022

(65) Prior Publication Data

US 2023/0330257 A1 Oct. 19, 2023

(30) Foreign Application Priority Data

Aug. 26, 2020 (CN) ........................ 202010873215.X

(51) Int. Cl.
*A61P 35/02* (2006.01)
*A61K 47/68* (2017.01)
*C07K 16/28* (2006.01)

(52) U.S. Cl.
CPC ...... *A61K 47/6879* (2017.08); *A61K 47/6801* (2017.08); *A61K 47/6849* (2017.08); *A61P 35/02* (2018.01); *C07K 16/2809* (2013.01); *C07K 16/2887* (2013.01)

(58) Field of Classification Search
CPC ............ C07K 16/2809; C07K 16/2887; C07K 2317/24; C07K 2317/33; C07K 2317/515; C07K 2317/52; C07K 2317/524; C07K 2317/526; C07K 2317/53; C07K 2317/565; C07K 2317/567; C07K 2317/92; C07K 2317/94; C07K 2317/31; C07K 2317/70; C07K 2317/71; A61K 2039/505; A61P 35/00
USPC ....................................................... 424/136.1
See application file for complete search history.

(56) References Cited

U.S. PATENT DOCUMENTS

| | | | | |
|---|---|---|---|---|
| 5,635,483 | A | 6/1997 | Pettit et al. | |
| 5,736,137 | A | 4/1998 | Anderson et al. | |
| 5,780,588 | A | 7/1998 | Pettit et al. | |
| 6,214,345 | B1 | 4/2001 | Firestone et al. | |
| 6,485,943 | B2 | 11/2002 | Stevens et al. | |
| 8,529,902 | B2 | 9/2013 | Teeling et al. | |
| 10,544,220 | B2 | 1/2020 | Engelberts et al. | |
| 2010/0015133 | A1 | 1/2010 | Igawa et al. | |
| 2017/0174781 | A1 | 6/2017 | Brownstein | |
| 2017/0355767 | A1* | 12/2017 | Engelberts | A61P 35/02 |
| 2024/0002540 | A1 | 1/2024 | Chen et al. | |
| 2024/0043568 | A1 | 2/2024 | Chen et al. | |

FOREIGN PATENT DOCUMENTS

| | | | |
|---|---|---|---|
| CA | 2885156 | A1 | 3/2014 |
| CN | 1912111 | A | 2/2007 |
| CN | 103709250 | A | 4/2014 |
| CN | 104640881 | A | 5/2015 |
| CN | 108059680 | A | 5/2018 |
| CN | 110088135 | A | 8/2019 |
| CN | 110603266 | A | 12/2019 |
| CN | 111138545 | A | 5/2020 |
| CN | 111356477 | A | 6/2020 |
| CN | 111454357 | A | 7/2020 |
| CN | 112062855 | A | 12/2020 |
| EP | 4257607 | A1 | 10/2023 |
| WO | WO-1988/007089 | A1 | 9/1988 |
| WO | WO-1996/027011 | A1 | 9/1996 |
| WO | WO-1998/050431 | A2 | 11/1998 |
| WO | WO-2000/042072 | A2 | 7/2000 |
| WO | WO-2002088172 | A2 | 11/2002 |
| WO | WO-2003026577 | A2 | 4/2003 |
| WO | WO-2004010957 | A2 | 2/2004 |
| WO | WO-2004/035607 | A2 | 4/2004 |
| WO | WO-2005084390 | A2 | 3/2005 |
| WO | WO-2005081711 | A2 | 9/2005 |
| WO | WO-2005082023 | A2 | 9/2005 |

(Continued)

OTHER PUBLICATIONS

Byers, T. (CA Cancer Journal, 1999, 49: 353-361).*
Alegre, M.L. et al., Effect of a single amino acid mutation on the activating and immunosuppressive properties of a "humanized" OKT3 monoclonal antibody, J. Immunol., 148(11):3461-3468 (1992).
Angal, S. et al., A single amino acid substitution abolishes the heterogeneity of chimeric mouse/human (IgG4) antibody, Mol. Immunol., 30(1):105-108 (1993).
International Search Report for PCT/CN2021/114847, 11 pages, (mailed Nov. 25, 2021).

(Continued)

*Primary Examiner* — Yan Xiao
(74) *Attorney, Agent, or Firm* — Choate, Hall & Stewart LLP; Charles E. Lyon; Rolando Medina

(57) ABSTRACT

Provided are a bispecific antibody binding to CD20 and CD3 and the use thereof. The bispecific antibody contains a first binding domain which binds to CD20 on the surface of a target cell and a second binding domain which binds to CD3 on the surface of T cell. The bispecific antibody is well tolerated, can effectively eliminate B cells under low-dose conditions, and has both better efficacy and safety than similar antibodies.

14 Claims, 19 Drawing Sheets

Specification includes a Sequence Listing.

(56) References Cited

FOREIGN PATENT DOCUMENTS

| | | | |
|---|---|---|---|
| WO | WO-2006/106905 | A1 | 10/2006 |
| WO | WO-2006132670 | A2 | 12/2006 |
| WO | WO-2007011968 | A3 | 1/2007 |
| WO | WO-2012059882 | A2 | 5/2012 |
| WO | WO-2012/130831 | A1 | 10/2012 |
| WO | WO-2012/162067 | A2 | 11/2012 |
| WO | WO-2014047231 | A1 | 9/2013 |
| WO | WO-2016/086189 | A2 | 6/2016 |
| WO | WO-2017112762 | A1 | 6/2017 |
| WO | WO-2019/228406 | A1 | 12/2019 |
| WO | WO-2021/027674 | A1 | 2/2021 |
| WO | WO-2022/042661 | A1 | 3/2022 |
| WO | WO-2022/105924 | A1 | 5/2022 |
| WO | WO-2022/117045 | A1 | 6/2022 |
| WO | WO-2022/117050 | A1 | 6/2022 |
| WO | WO-2024/002308 | A1 | 1/2024 |

OTHER PUBLICATIONS

Lu, C.Y. et al., Tetravalent anti-CD20/CD3 bispecific antibody for the treatment of B cell lymphoma, Biochem. Biophys. Res. Commun., 473(4):808-813 (2016).

Newman, R. et al., Modification of the Fc region of a primatized IgG antibody to human CD4 retains its ability to modulate CD4 receptors but does not deplete CD4(+) T cells in chimpanzees, Clin. Immunol., 98(2):164-174 (2001).

Pessano, S. et al., The T3/T cell receptor complex: antigenic distinction between the two 20-kd T3 (T3-delta and T3-epsilon) subunits, EMBO J., 4(2):337-344 (1985).

Smith, E.J. et al., A novel, native-format bispecific antibody triggering T-cell killing of B-cells is robustly active in mouse tumor models and cynomolgus monkeys, Sci. Rep., 5:17943 (2015).

Written Opinion for PCT/CN2021/114847, 5 pages, (mailed Nov. 25, 2021).

* cited by examiner

SEQUENCE LISTING

```
<160> NUMBER OF SEQ ID NOS: 123

<210> SEQ ID NO 1
<211> LENGTH: 306
<212> TYPE: PRT
<213> ORGANISM: Homo sapiens

<400> SEQUENCE: 1

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Pro Glu Ala Ala Gly Gly
                85                  90                  95

Pro Ser Val Phe Leu Phe Pro Pro Lys Pro Lys Asp Thr Leu Met Ile
            100                 105                 110

Ser Arg Thr Pro Glu Val Thr Cys Val Val Val Asp Val Ser His Glu
        115                 120                 125

Asp Pro Glu Val Lys Phe Asn Trp Tyr Val Asp Gly Val Glu Val His
    130                 135                 140

Asn Ala Lys Thr Lys Pro Arg Glu Glu Gln Tyr Asn Ser Thr Tyr Arg
145                 150                 155                 160

Val Val Ser Val Leu Thr Val Leu His Gln Asp Trp Leu Asn Gly Lys
                165                 170                 175

Glu Tyr Lys Cys Lys Val Ser Asn Lys Ala Leu Pro Ala Ser Ile Glu
            180                 185                 190

Lys Thr Ile Ser Lys Ala Lys Gly Gln Pro Arg Glu Pro Gln Val Cys
        195                 200                 205

Thr Leu Pro Pro Ser Arg Asp Glu Leu Thr Lys Asn Gln Val Ser Leu
    210                 215                 220

Ser Cys Ala Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Val Ser Lys Leu Thr Val Asp
            260                 265                 270

Lys Ser Arg Trp Gln Gln Gly Asn Val Phe Ser Cys Ser Val Met His
        275                 280                 285

Glu Ala Leu His Asn His Tyr Thr Gln Lys Ser Leu Ser Leu Ser Pro
    290                 295                 300

Gly Lys
305


<210> SEQ ID NO 2
<211> LENGTH: 339
<212> TYPE: PRT
<213> ORGANISM: Homo sapiens

<400> SEQUENCE: 2

Gln Asp Gly Asn Glu Glu Met Gly Gly Ile Thr Gln Thr Pro Tyr Lys
```

```
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Ala Pro Glu Ala Ala Gly Gly
            100                 105                 110

Pro Ser Val Phe Leu Phe Pro Pro Lys Pro Lys Asp Thr Leu Met Ile
        115                 120                 125

Ser Arg Thr Pro Glu Val Thr Cys Val Val Val Asp Val Ser His Glu
    130                 135                 140

Asp Pro Glu Val Lys Phe Asn Trp Tyr Val Asp Gly Val Glu Val His
145                 150                 155                 160

Asn Ala Lys Thr Lys Pro Arg Glu Glu Gln Tyr Asn Ser Thr Tyr Arg
                165                 170                 175

Val Val Ser Val Leu Thr Val Leu His Gln Asp Trp Leu Asn Gly Lys
            180                 185                 190

Glu Tyr Lys Cys Lys Val Ser Asn Lys Ala Leu Pro Ala Ser Ile Glu
        195                 200                 205

Lys Thr Ile Ser Lys Ala Lys Gly Gln Pro Arg Glu Pro Gln Val Tyr
    210                 215                 220

Thr Leu Pro Pro Cys Arg Asp Glu Leu Thr Lys Asn Gln Val Ser Leu
225                 230                 235                 240

Trp Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Val
            260                 265                 270

Leu Asp Ser Asp Gly Ser Phe Phe Leu Tyr Ser Lys Leu Thr Val Asp
        275                 280                 285

Lys Ser Arg Trp Gln Gln Gly Asn Val Phe Ser Cys Ser Val Met His
    290                 295                 300

Glu Ala Leu His Asn His Tyr Thr Gln Lys Ser Leu Ser Leu Ser Pro
305                 310                 315                 320

Gly Lys Gly Ser Gly Leu Asn Asp Ile Phe Glu Ala Gln Lys Ile Glu
                325                 330                 335

Trp His Glu


<210> SEQ ID NO 3
<211> LENGTH: 305
<212> TYPE: PRT
<213> ORGANISM: Homo sapiens

<400> SEQUENCE: 3

Gln Ser Phe Glu Glu Asn Arg Lys Leu Asn Val Tyr Asn Gln Glu Asp
1               5                   10                  15

Gly Ser Val Leu Leu Thr Cys His Val Lys Asn Thr Asn Ile Thr Trp
            20                  25                  30

Phe Lys Glu Gly Lys Met Ile Asp Ile Leu Thr Ala His Lys Asn Lys
```

```
        35                  40                  45

Trp Asn Leu Gly Ser Asn Thr Lys Asp Pro Arg Gly Val Tyr Gln Cys
    50                  55                  60

Lys Gly Ser Lys Asp Lys Ser Lys Thr Leu Gln Val Tyr Tyr Arg Met
65                  70                  75                  80

Cys Gln Asn Cys Ile Glu Leu Asn Ala Pro Glu Ala Ala Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Asn Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Ser Ile Glu Lys
            180                 185                 190

Thr Ile Ser Lys Ala Lys Gly Gln Pro Arg Glu Pro Gln Val Cys Thr
        195                 200                 205

Leu Pro Pro Ser Arg Asp Glu Leu Thr Lys Asn Gln Val Ser Leu Ser
    210                 215                 220

Cys Ala Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Val Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300

Lys
305


<210> SEQ ID NO 4
<211> LENGTH: 330
<212> TYPE: PRT
<213> ORGANISM: Homo sapiens

<400> SEQUENCE: 4

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95
```

Ala Pro Glu Ala Ala Gly Gly Pro Ser Val Phe Leu Phe Pro Pro Lys
100 105 110

Pro Lys Asp Thr Leu Met Ile Ser Arg Thr Pro Glu Val Thr Cys Val
115 120 125

Val Val Asp Val Ser His Glu Asp Pro Glu Val Lys Phe Asn Trp Tyr
130 135 140

Val Asp Gly Val Glu Val His Asn Ala Lys Thr Lys Pro Arg Glu Glu
145 150 155 160

Gln Tyr Asn Ser Thr Tyr Arg Val Val Ser Val Leu Thr Val Leu His
165 170 175

Gln Asp Trp Leu Asn Gly Lys Glu Tyr Lys Cys Lys Val Ser Asn Lys
180 185 190

Ala Leu Pro Ala Ser Ile Glu Lys Thr Ile Ser Lys Ala Lys Gly Gln
195 200 205

Pro Arg Glu Pro Gln Val Tyr Thr Leu Pro Pro Cys Arg Asp Glu Leu
210 215 220

Thr Lys Asn Gln Val Ser Leu Trp Cys Leu Val Lys Gly Phe Tyr Pro
225 230 235 240

Ser Asp Ile Ala Val Glu Trp Glu Ser Asn Gly Gln Pro Glu Asn Asn
245 250 255

Tyr Lys Thr Thr Pro Pro Val Leu Asp Ser Asp Gly Ser Phe Phe Leu
260 265 270

Tyr Ser Lys Leu Thr Val Asp Lys Ser Arg Trp Gln Gln Gly Asn Val
275 280 285

Phe Ser Cys Ser Val Met His Glu Ala Leu His Asn His Tyr Thr Gln
290 295 300

Lys Ser Leu Ser Leu Ser Pro Gly Lys Gly Ser Gly Leu Asn Asp Ile
305 310 315 320

Phe Glu Ala Gln Lys Ile Glu Trp His Glu
325 330

<210> SEQ ID NO 5
<211> LENGTH: 109
<212> TYPE: PRT
<213> ORGANISM: Homo sapiens

<400> SEQUENCE: 5

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Trp Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu
100 105

<210> SEQ ID NO 6
<211> LENGTH: 327
<212> TYPE: DNA
<213> ORGANISM: Homo sapiens

<400> SEQUENCE: 6

```
caggctgtgg tcacacaaga gcctagcctg acagtgtctc ctggcggcac agtgaccctg      60
acctgtagat cttctacagg cgccgtgacc accagcaact acgctaattg ggtgcagcag     120
aagcccggcc aggctcctag aggactgatc ggcggaacaa acaagagagc cccttggaca     180
cccgccagat tctctggatc tctgctcggc ggaaaggccg ctctgacact ttctggtgct     240
cagcctgagg acgaggccga gtactattgt gccctgtggt acagcaacct gtgggtgttc     300
ggcggaggca ccaaactgac agttctg                                         327
```

<210> SEQ ID NO 7
<211> LENGTH: 14
<212> TYPE: PRT
<213> ORGANISM: Homo sapiens

<400> SEQUENCE: 7

```
Arg Ser Ser Thr Gly Ala Val Thr Thr Ser Asn Tyr Ala Asn
1               5                   10
```

<210> SEQ ID NO 8
<211> LENGTH: 8
<212> TYPE: PRT
<213> ORGANISM: Homo sapiens

<400> SEQUENCE: 8

```
Gly Gly Thr Asn Lys Arg Ala Pro
1               5
```

<210> SEQ ID NO 9
<211> LENGTH: 9
<212> TYPE: PRT
<213> ORGANISM: Homo sapiens

<400> SEQUENCE: 9

```
Ala Leu Trp Tyr Ser Asn Leu Trp Val
1               5
```

<210> SEQ ID NO 10
<211> LENGTH: 109
<212> TYPE: PRT
<213> ORGANISM: Homo sapiens

<400> SEQUENCE: 10

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 11

<211> LENGTH: 327
<212> TYPE: DNA
<213> ORGANISM: Homo sapiens

<400> SEQUENCE: 11
caggctgtgg tcacacaaga gcctagcctg acagtgtctc ctggcggcac agtgaccctg 60
acctgtagat cttctacagg cgccgtgacc accagcaact acgctaattg ggtgcaggag 120
aagcccggcc aggctcctag aggactgatc ggcggaacaa acaagagagc cccttggaca 180
cccgccagat tctctggatc tctgctcggc ggaaaggccg ctctgacact ttctggtgct 240
cagcctgagg acgaggccga gtactattgt gccctgtggt acagcaacct gtgggtgttc 300
ggcggaggca ccaaactgac agttctg 327

<210> SEQ ID NO 12
<211> LENGTH: 109
<212> TYPE: PRT
<213> ORGANISM: Homo sapiens

<400> SEQUENCE: 12

Glu Ala Val Val Thr Gln Glu Pro Ser Leu Thr Val Ser Pro Gly Gly
1 5 10 15

Thr Val Thr Leu Thr Cys Glu Ser Ser Asp Gly Ala Val Thr Thr Ser
20 25 30

Asn Tyr Ala Asn Trp Val Gln Glu Lys Pro Gly Gln Ala Pro Arg Gly
35 40 45

Leu Ile Gly Gly Thr Asn Lys Glu Ala Pro Trp Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu
100 105

<210> SEQ ID NO 13
<211> LENGTH: 327
<212> TYPE: DNA
<213> ORGANISM: Homo sapiens

<400> SEQUENCE: 13
gaggctgtgg tcacacaaga gcctagcctg acagtgtctc ctggcggcac agtgaccctg 60
acctgtgagt cttctgacgg cgccgtgacc accagcaact acgctaattg ggtgcaggag 120
aagcccggcc aggctcctag aggactgatc ggcggaacaa acaaggaggc cccttggaca 180
cccgccagat tctctggatc tctgctcggc ggaaaggccg ctctgacact ttctggtgct 240
cagcctgagg acgaggccga gtactattgt gccctgtggt acagcaacct gtgggtgttc 300
ggcggaggca ccaaactgac agttctg 327

<210> SEQ ID NO 14
<211> LENGTH: 14
<212> TYPE: PRT
<213> ORGANISM: Homo sapiens

<400> SEQUENCE: 14

Glu Ser Ser Asp Gly Ala Val Thr Thr Ser Asn Tyr Ala Asn
1 5 10

<210> SEQ ID NO 15
<211> LENGTH: 8
<212> TYPE: PRT
<213> ORGANISM: Homo sapiens

<400> SEQUENCE: 15

```
Gly Gly Thr Asn Lys Glu Ala Pro
1               5
```

<210> SEQ ID NO 16
<211> LENGTH: 109
<212> TYPE: PRT
<213> ORGANISM: Homo sapiens

<400> SEQUENCE: 16

```
Gln Ala Val Val Thr Gln Glu Pro Ser Leu Thr Val Ser Pro Gly Gly
1               5                   10                  15

Thr Val Thr Leu Thr Cys Glu Ser Ser Asp Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Glu Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 17
<211> LENGTH: 327
<212> TYPE: DNA
<213> ORGANISM: Homo sapiens

<400> SEQUENCE: 17

```
caggctgtgg tcacacaaga gcctagcctg acagtgtctc ctggcggcac agtgaccctg      60

acctgtgagt cttctgacgg cgccgtgacc accagcaact acgctaattg ggtgcaggag     120

aagcccggcc aggctcctag aggactgatc ggcggaacaa acaaggaggc cccttggaca     180

cccgccagat tctctggatc tctgctcggc ggaaaggccg ctctgacact ttctggtgct     240

cagcctgagg acgaggccga gtactattgt gccctgtggt acagcaacct gtgggtgttc     300

ggcggaggca ccaaactgac agttctg                                         327
```

<210> SEQ ID NO 18
<211> LENGTH: 109
<212> TYPE: PRT
<213> ORGANISM: Homo sapiens

<400> SEQUENCE: 18

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60
```

```
Ser Gly Ser Leu Leu Gly Gly Lys Ala Ala Leu Thr Ile Thr Gly Ala
65                  70                  75                  80

Gln Ala Glu Asp Glu Ala Glu Tyr Tyr Cys Val Leu Trp Tyr Ser Asn
                85                  90                  95

Leu Trp Val Phe Gly Gly Gly Thr Lys Leu Thr Val Leu
            100                 105


<210> SEQ ID NO 19
<211> LENGTH: 327
<212> TYPE: DNA
<213> ORGANISM: Homo sapiens

<400> SEQUENCE: 19

caggctgtgg tcacacaaga gcctagcctg acagtgtctc ctggcggcac agtgaccctg      60

acctgtagat cttctacagg cgccgtgacc accagcaact acgctaattg ggtgcaggag     120

aagcccggcc aggctcctag aggactgatc ggcggaacaa acaagagagc cccttggaca     180

cccgccagat tctctggatc tctgctcggc ggaaaggccg ctctgacaat cactggtgct     240

caggctgagg acgaggccga gtactattgt gtgctgtggt acagcaacct gtgggtgttc     300

ggcggaggca ccaaactgac agttctg                                         327


<210> SEQ ID NO 20
<211> LENGTH: 8
<212> TYPE: PRT
<213> ORGANISM: Homo sapiens

<400> SEQUENCE: 20

Tyr Gly Thr Asn Lys Arg Ala Pro
1               5


<210> SEQ ID NO 21
<211> LENGTH: 9
<212> TYPE: PRT
<213> ORGANISM: Homo sapiens

<400> SEQUENCE: 21

Val Leu Trp Tyr Ser Asn Leu Trp Val
1               5


<210> SEQ ID NO 22
<211> LENGTH: 109
<212> TYPE: PRT
<213> ORGANISM: Homo sapiens

<400> SEQUENCE: 22

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Glu Lys Pro Gly Gln Ala Pro Arg Gly
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Ala Glu Asp Glu Ala Glu Tyr Tyr Cys Val Leu Trp Tyr Ser Asn
                85                  90                  95

Leu Trp Val Phe Gly Gly Gly Thr Lys Leu Thr Val Leu
            100                 105
```

<210> SEQ ID NO 23
<211> LENGTH: 327
<212> TYPE: DNA
<213> ORGANISM: Homo sapiens

<400> SEQUENCE: 23
caggctgtgg tcacacaaga gcctagcctg acagtgtctc ctggcggcac agtgaccctg 60
acctgtagat cttctacagg cgccgtgacc accagcaact acgctaattg gttccaggag 120
aagcccggcc aggctcctag aggactgatc tacggaacaa acaagagagc cccttggaca 180
cccgccagat tctctggatc tctgctcggc ggaaaggccg ctctgacact ttctggtgct 240
caggctgagg acgaggccga gtactattgt gtcctgtggt acagcaacct gtgggtgttc 300
ggcggaggca ccaaactgac agttctg 327

<210> SEQ ID NO 24
<211> LENGTH: 125
<212> TYPE: PRT
<213> ORGANISM: Homo sapiens

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 25
<211> LENGTH: 375
<212> TYPE: DNA
<213> ORGANISM: Homo sapiens

<400> SEQUENCE: 25
gaggtgcagc tggttgaatc tggcggagga ctggttcagc ctggcggatc tctgagactg 60
tcttgtgccg ccagcggctt caccttcaac acctacgcta tgaactgggt ccgacaggcc 120
cctggcaaag gactggaatg ggtgtccaga atcaggtcca agtacaacaa ctacgccacc 180
tactacgccg acagcgtgaa ggacagattc accatcagca gggacgacag caagaacacc 240
ctgtacctgc agatgaacag cctgagagcc gaggacaccg ccgtgtacta ctgtgtcaga 300
cacggcaact tcggcaacag ctatgtgtct tggtttgcct actggggcca gggcacactg 360
gtcacagtta gctct 375

<210> SEQ ID NO 26
<211> LENGTH: 6
<212> TYPE: PRT

<213> ORGANISM: Homo sapiens

<400> SEQUENCE: 26

Asn Thr Tyr Ala Met Asn
1 5

<210> SEQ ID NO 27
<211> LENGTH: 18
<212> TYPE: PRT
<213> ORGANISM: Homo sapiens

<400> SEQUENCE: 27

Ile Arg Ser Lys Tyr Asn Asn Tyr Ala Thr Tyr Tyr Ala Asp Ser Val
1 5 10 15

Lys Asp

<210> SEQ ID NO 28
<211> LENGTH: 14
<212> TYPE: PRT
<213> ORGANISM: Homo sapiens

<400> SEQUENCE: 28

His Gly Asn Phe Gly Asn Ser Tyr Val Ser Trp Phe Ala Tyr
1 5 10

<210> SEQ ID NO 29
<211> LENGTH: 125
<212> TYPE: PRT
<213> ORGANISM: Homo sapiens

<400> SEQUENCE: 29

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Lys Ala Pro Gly Lys Gly Leu Glu Trp Val
35 40 45

Ser Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 30
<211> LENGTH: 375
<212> TYPE: DNA
<213> ORGANISM: Homo sapiens

<400> SEQUENCE: 30
gaggtgcagc tggttgaatc tggcggagga ctggttcagc ctggcggatc tctgagactg 60
tcttgtgccg ccagcggctt caccttctcc acctacgcta tgaactgggt ccgaaaggcc 120
cctggcaaag gactggaatg ggtgtccaga atcaggtcca agtacaacaa ctacgccacc 180
tactacgccg acagcgtgaa ggacagattc accatcagca gggacgacag caagaacacc 240
ctgtacctgc agatgaacag cctgagagcc gaggacaccg ccgtgtacta ctgtgtcaga 300
cacggcaact tcggcaacag ctatgtgtct tggtttgcct actggggcca gggcacactg 360
gtcacagtta gctct 375

<210> SEQ ID NO 31
<211> LENGTH: 6
<212> TYPE: PRT
<213> ORGANISM: Homo sapiens

<400> SEQUENCE: 31

Ser Thr Tyr Ala Met Asn
1 5

<210> SEQ ID NO 32
<211> LENGTH: 125
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Lys Ala Pro Gly Lys Gly Leu Glu Trp Val
35 40 45

Ser Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Glu Ser Tyr Val Ser Trp Phe
100 105 110

Ala Tyr Trp Gly Gln Gly Thr Leu Val Thr Val Ser Ser
115 120 125

<210> SEQ ID NO 33
<211> LENGTH: 375
<212> TYPE: DNA
<213> ORGANISM: Homo sapiens

<400> SEQUENCE: 33
gaggtgcagc tggttgaatc tggcggagga ctggttcagc ctggcggatc tctgagactg 60
tcttgtgccg ccagcggctt caccttctcc acctacgcta tgaactgggt ccgaaaggcc 120
cctggcaaag gactggaatg ggtgtccaga atcaggtcca agtacaacaa ctacgccacc 180
tactacgccg acagcgtgaa ggacagattc accatcagca gggacgacag caagaacacc 240
ctgtacctgc agatgaacag cctgagagcc gaggacaccg ccgtgtacta ctgtgtcaga 300
cacggcaact tcggcgagag ctatgtgtct tggtttgcct actggggcca gggcacactg 360
gtcacagtta gctct 375

<210> SEQ ID NO 34
<211> LENGTH: 14
<212> TYPE: PRT
<213> ORGANISM: Homo sapiens

<400> SEQUENCE: 34

```
His Gly Asn Phe Gly Glu Ser Tyr Val Ser Trp Phe Ala Tyr
1               5                   10


<210> SEQ ID NO 35
<211> LENGTH: 125
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Lys Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Ala Tyr Trp Gly Gln Gly Thr Leu Val Thr Val Ser Ser
        115                 120                 125


<210> SEQ ID NO 36
<211> LENGTH: 375
<212> TYPE: DNA
<213> ORGANISM: Homo sapiens

<400> SEQUENCE: 36

gaggtgcagc tggttgaatc tggcggagga ctggttcagc ctggcggatc tctgagactg     60

tcttgtgccg ccagcggctt caccttctcc acctacgcta tgaactgggt ccgaaaggcc    120

cctggcaaag gactggaatg ggtgtccaga atcaggtcca agtacaacaa ctacgccacc    180

tactacgccg acagcgtgaa ggacagattc accatcagca gggacgacag caagaacacc    240

ctgtacctgc agatgaacag cctgagagcc gaggacaccg ccgtgtacta ctgtgtcaga    300

cacggcaact tcggccagag ctatgtgtct tggtttgcct actggggcca gggcacactg    360

gtcacagtta gctct                                                     375


<210> SEQ ID NO 37
<211> LENGTH: 14
<212> TYPE: PRT
<213> ORGANISM: Homo sapiens

<400> SEQUENCE: 37

His Gly Asn Phe Gly Gln Ser Tyr Val Ser Trp Phe Ala Tyr
1               5                   10


<210> SEQ ID NO 38
<211> LENGTH: 125
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Thr Tyr
            20                  25                  30

Ala Met Asn Trp Val Arg Lys Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125


<210> SEQ ID NO 39
<211> LENGTH: 375
<212> TYPE: DNA
<213> ORGANISM: Homo sapiens

<400> SEQUENCE: 39

gaggtgcagc tggttgaatc tggcggagga ctggttcagc ctggcggatc tctgagactg      60

tcttgtgccg ccagcggctt caccttctcc acctacgcta tgaactgggt ccgaaaggcc     120

cctggcaaag gactggaatg ggtgtccaga atcaggtcca agtacaacaa ctacgccacc     180

tactacgccg acagcgtgaa ggacagattc accatcagca gggacgacag caagaacacc     240

ctgtacctgc agatgaacag cctgagagcc gaggacaccg ccgtgtacta ctgtgtcaga     300

cacggcaact tcggcgacag ctatgtgtct tggtttgcct actggggcca gggcacactg     360

gtcacagtta gctct                                                      375


<210> SEQ ID NO 40
<211> LENGTH: 14
<212> TYPE: PRT
<213> ORGANISM: Homo sapiens

<400> SEQUENCE: 40

His Gly Asn Phe Gly Asp Ser Tyr Val Ser Trp Phe Ala Tyr
1               5                   10


<210> SEQ ID NO 41
<211> LENGTH: 125
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Lys Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

Tyr Cys Val Arg His Gly Asn Phe Gly Thr Ser Tyr Val Ser Trp Phe
100 105 110

Ala Tyr Trp Gly Gln Gly Thr Leu Val Thr Val Ser Ser
115 120 125

<210> SEQ ID NO 42
<211> LENGTH: 375
<212> TYPE: DNA
<213> ORGANISM: Homo sapiens

<400> SEQUENCE: 42
gaggtgcagc tggttgaatc tggcggagga ctggttcagc ctggcggatc tctgagactg 60
tcttgtgccg ccagcggctt caccttctcc acctacgcta tgaactgggt ccgaaaggcc 120
cctggcaaag gactggaatg ggtgtccaga atcaggtcca agtacaacaa ctacgccacc 180
tactacgccg acagcgtgaa ggacagattc accatcagca gggacgacag caagaacacc 240
ctgtacctgc agatgaacag cctgagagcc gaggacaccg ccgtgtacta ctgtgtcaga 300
cacggcaact tcggcaccag ctatgtgtct tggtttgcct actggggcca gggcacactg 360
gtcacagtta gctct 375

<210> SEQ ID NO 43
<211> LENGTH: 14
<212> TYPE: PRT
<213> ORGANISM: Homo sapiens

<400> SEQUENCE: 43

His Gly Asn Phe Gly Thr Ser Tyr Val Ser Trp Phe Ala Tyr
1 5 10

<210> SEQ ID NO 44
<211> LENGTH: 125
<212> TYPE: PRT
<213> ORGANISM: Homo sapiens

<400> SEQUENCE: 44

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Met Asn Trp Val Arg Lys Ala Pro Gly Lys Gly Leu Glu Trp Val
35 40 45

Ser Arg Ile Arg Ser Lys Tyr Asn Asn Tyr Ala Thr Tyr Tyr Ala Asp
50 55 60

Ser Val Glu Asp Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 45
<211> LENGTH: 375
<212> TYPE: DNA
<213> ORGANISM: Homo sapiens

<400> SEQUENCE: 45

```
gaggtgcagc tggttgaatc tggcggagga ctggttcagc ctggcggatc tctgagactg     60

tcttgtgccg ccagcggctt caccttctcc gactacgcta tgaactgggt ccgaaaggcc    120

cctggcaaag gactggaatg ggtgtccaga atcaggtcca agtacaacaa ctacgccacc    180

tactacgccg acagcgtgga ggacagattc accatcagca gggacgacag caagaacacc    240

ctgtacctgc agatgaacag cctgagagcc gaggacaccg ccgtgtacta ctgtgtcaga    300

cacggcaact tcggcaacag ctatgtgtct tggtttgcct actggggcca gggcacactg    360

gtcacagtta gctct                                                     375
```

<210> SEQ ID NO 46
<211> LENGTH: 6
<212> TYPE: PRT
<213> ORGANISM: Homo sapiens

<400> SEQUENCE: 46

```
Ser Asp Tyr Ala Met Asn
1               5
```

<210> SEQ ID NO 47
<211> LENGTH: 18
<212> TYPE: PRT
<213> ORGANISM: Homo sapiens

<400> SEQUENCE: 47

```
Ile Arg Ser Lys Tyr Asn Asn Tyr Ala Thr Tyr Tyr Ala Asp Ser Val
1               5                   10                  15

Glu Asp
```

<210> SEQ ID NO 48
<211> LENGTH: 125
<212> TYPE: PRT
<213> ORGANISM: Homo sapiens

<400> SEQUENCE: 48

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Lys Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 49
<211> LENGTH: 375
<212> TYPE: DNA
<213> ORGANISM: Homo sapiens

<400> SEQUENCE: 49

```
gaggtgcagc tggttgaatc tggcggagga ctggttcagc ctggcggatc tctgagactg     60

tcttgtgccg ccagcggctt caccttcaac acctacgcta tgaactgggt ccgaaaggcc    120

cctggcaaag gactggaatg ggtgggaaga atcaggtcca agtacaacaa ctacgccacc    180

tactacgccg acagcgtgaa ggacagattc accatcagca gggacgacag caagaacagc    240

ctgtacctgc agatgaacag cctgaaaacc gaggacaccg ccgtgtacta ctgtgccaga    300

cacggcaact tcggcaacag ctatgtgtct tggtttgcct actggggcca gggcacactg    360

gtcacagtta gctct                                                     375


<210> SEQ ID NO 50
<211> LENGTH: 125
<212> TYPE: PRT
<213> ORGANISM: Homo sapiens

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Lys Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 51
<211> LENGTH: 375
<212> TYPE: DNA
<213> ORGANISM: Homo sapiens

<400> SEQUENCE: 51

gaggtgcagc tggttgaatc tggcggagga ctggttcagc ctggcggatc tctgagactg     60

tcttgtgccg ccagcggctt caccttcaac acctacgcta tgaactgggt ccgaaaggcc    120

cctggcaaag gactggaatg ggtgggaaga atcaggtcca agtacaacaa ctacgccacc    180

tactacgccg acagcgtgaa ggacagattc accatcagca gggacgacag caagaacagc    240

ctgtacctgc agatgaacag cctgaaaacc gaggacaccg ccgtgtacta ctgtgtcaga    300

cacggcaact tcggcaacag ctatgtgtct tggtttgcct actggggcca gggcacactg    360

gtcacagtta gctct                                                     375


<210> SEQ ID NO 52
<211> LENGTH: 125
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Thr Tyr
            20                  25                  30

Ala Met Asn Trp Val Arg Lys Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 53
<211> LENGTH: 375
<212> TYPE: DNA
<213> ORGANISM: Homo sapiens

<400> SEQUENCE: 53

```
gaggtgcagc tggttgaatc tggcggagga ctggttcagc ctggcggatc tctgagactg     60

tcttgtgccg ccagcggctt caccttcaac acctacgcta tgaactgggt ccgaaaggcc    120

cctggcaaag gactggaatg ggtggccaga atcaggtcca agtacaacaa ctacgccacc    180

tactacgccg acagcgtgaa ggacagattc accatcagca gggacgacag caagaacagc    240

ctgtacctgc agatgaacag cctgaaaacc gaggacaccg ccgtgtacta ctgtgtcaga    300

cacggcaact tcggcaacag ctatgtgtct tggtttgcct actggggcca gggcacactg    360

gtcacagtta gctct                                                      375
```

<210> SEQ ID NO 54
<211> LENGTH: 106
<212> TYPE: PRT
<213> ORGANISM: Homo sapiens

<400> SEQUENCE: 54

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Ile
            20                  25                  30

His Trp Phe Gln Gln Lys Pro Gly Gln Ala Pro Arg Pro Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Thr Ser Asn Pro Pro Thr
                85                  90                  95

Phe Gly Gln Gly Thr Lys Leu Glu Ile Lys
            100                 105
```

<210> SEQ ID NO 55
<211> LENGTH: 318
<212> TYPE: DNA
<213> ORGANISM: Homo sapiens

<400> SEQUENCE: 55

```
gagatcgtgc tgacacagag ccctggcaca ctgtcactgt ctccaggcga gagagccaca      60

ctgagctgta gagccagcag cagcgtgtcc tacatccact ggttccagca gaagcctgga     120

caggccccta gacctctgat ctacgccaca agcaacctgg ccagcggcat ccctgataga     180

ttcagcggct ctggcagcgg caccgactac acactgacaa tcagcagact ggaacccgag     240

gacttcgccg tgtactactg ccagcagtgg accagcaatc ctcctacatt cggccagggc     300

accaagctgg aaatcaag                                                   318


<210> SEQ ID NO 56
<211> LENGTH: 10
<212> TYPE: PRT
<213> ORGANISM: Homo sapiens

<400> SEQUENCE: 56

Arg Ala Ser Ser Ser Val Ser Tyr Ile His
1               5                   10


<210> SEQ ID NO 57
<211> LENGTH: 7
<212> TYPE: PRT
<213> ORGANISM: Homo sapiens

<400> SEQUENCE: 57

Ala Thr Ser Asn Leu Ala Ser
1               5


<210> SEQ ID NO 58
<211> LENGTH: 9
<212> TYPE: PRT
<213> ORGANISM: Homo sapiens

<400> SEQUENCE: 58

Gln Gln Trp Thr Ser Asn Pro Pro Thr
1               5


<210> SEQ ID NO 59
<211> LENGTH: 107
<212> TYPE: PRT
<213> ORGANISM: Homo sapiens

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Lys Leu Glu Ile Lys
            100                 105


<210> SEQ ID NO 60
<211> LENGTH: 321
<212> TYPE: DNA
```

<213> ORGANISM: Homo sapiens

<400> SEQUENCE: 60
gagatcgtgc tgacacagag ccctggcaca ctgtcactgt ctccaggcga gagagccaca 60
ctgagctgta gagccagcca gagcgtgtcc tcttacctgg cctggtatca gcagaagcct 120
ggacaggctc ccagactgct gatctacgac gccagcaaca gagccacagg catccccgat 180
agattcagcg gctctggctc tggcaccgac ttcaccctga caatcagcag actggaaccc 240
gaggacttcg ccgtgtacta ctgccagcag agaagcaact ggcccatcac attcggccag 300
ggcaccaagc tggaaatcaa g 321

<210> SEQ ID NO 61
<211> LENGTH: 11
<212> TYPE: PRT
<213> ORGANISM: Homo sapiens

<400> SEQUENCE: 61

Arg Ala Ser Gln Ser Val Ser Ser Tyr Leu Ala
1 5 10

<210> SEQ ID NO 62
<211> LENGTH: 7
<212> TYPE: PRT
<213> ORGANISM: Homo sapiens

<400> SEQUENCE: 62

Asp Ala Ser Asn Arg Ala Thr
1 5

<210> SEQ ID NO 63
<211> LENGTH: 9
<212> TYPE: PRT
<213> ORGANISM: Homo sapiens

<400> SEQUENCE: 63

Gln Gln Arg Ser Asn Trp Pro Ile Thr
1 5

<210> SEQ ID NO 64
<211> LENGTH: 121
<212> TYPE: PRT
<213> ORGANISM: Homo sapiens

<400> SEQUENCE: 64

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Asn Met His Trp Val Arg Gln Ala Pro Gly Gln Gly Leu Glu Trp Met
35 40 45

Gly Ala Ile Tyr Pro Gly Asn Gly Asp Thr Ser Tyr Asn Gln Lys Phe
50 55 60

Gln Gly Arg Val Thr Leu Thr Ala Asp Lys Ser Ser Ser Thr Ala Tyr
65 70 75 80

Met Glu Leu Ser Ser Leu Arg Ser Glu Asp Thr Ala Val Tyr Tyr Cys
85 90 95

Ala Arg Ser Thr Tyr Tyr Gly Gly Asp Trp Tyr Phe Asn Val Trp Gly
100 105 110

Gln Gly Thr Leu Val Thr Val Ser Ser 115 120

<210> SEQ ID NO 65
<211> LENGTH: 363
<212> TYPE: DNA
<213> ORGANISM: Homo sapiens

<400> SEQUENCE: 65
caggttcagc tggttcagtc tggcgccgaa gtgaagaaac ctggcagcag cgtgaaggtg 60
tcctgcaagg ctagcggcta cacattcacc agctacaaca tgcactgggt ccgacaggcc 120
cctggacagg gacttgaatg gatgggcgct atctaccctg gcaacggcga cacctcctac 180
aaccagaaat tccagggcag agtgaccctg accgccgaca agtctagcag caccgcctac 240
atggaactga gcagcctgag aagcgaggac accgccgtgt actactgtgc cagaagcacc 300
tactacggcg gcgactggta cttcaacgtg tggggacagg gaaccctggt caccgtttct 360
tct 363

<210> SEQ ID NO 66
<211> LENGTH: 5
<212> TYPE: PRT
<213> ORGANISM: Homo sapiens

<400> SEQUENCE: 66

Ser Tyr Asn Met His
1 5

<210> SEQ ID NO 67
<211> LENGTH: 17
<212> TYPE: PRT
<213> ORGANISM: Homo sapiens

<400> SEQUENCE: 67

Ala Ile Tyr Pro Gly Asn Gly Asp Thr Ser Tyr Asn Gln Lys Phe Gln
1 5 10 15

Gly

<210> SEQ ID NO 68
<211> LENGTH: 12
<212> TYPE: PRT
<213> ORGANISM: Homo sapiens

<400> SEQUENCE: 68

Ser Thr Tyr Tyr Gly Gly Asp Trp Tyr Phe Asn Val
1 5 10

<210> SEQ ID NO 69
<211> LENGTH: 121
<212> TYPE: PRT
<213> ORGANISM: Homo sapiens

<400> SEQUENCE: 69

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Asn Met His Trp Val Arg Gln Ala Pro Gly Gln Gly Leu Glu Trp Met
35 40 45

Gly Ala Ile Tyr Pro Gly Asn Gly Asp Thr Ser Tyr Asn Gln Lys Phe
50 55 60

```
Gln Gly Arg Val Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asp Tyr Trp Gly
            100                 105                 110

Gln Gly Thr Leu Val Thr Val Ser Ser
        115                 120


<210> SEQ ID NO 70
<211> LENGTH: 363
<212> TYPE: DNA
<213> ORGANISM: Homo sapiens

<400> SEQUENCE: 70

caggttcagc tggttcagtc tggcgccgaa gtgaagaaac ctggcagcag cgtgaaggtg      60

tcctgcaagg ctagcggcta cacattcacc agctacaaca tgcactgggt ccgacaggcc     120

cctggacagg gacttgaatg gatgggcgct atctaccctg gcaacggcga cacctcctac     180

aaccagaaat tccagggcag agtgaccctg accgccgaca agtctagcag caccgcctac     240

atggaactga gcagcctgag aagcgaggac accgccgtgt actactgtgc cagaagcacc     300

tactacggcg gcgactggta cttcgactat tggggacagg gaaccctggt caccgtttct     360

tct                                                                   363


<210> SEQ ID NO 71
<211> LENGTH: 12
<212> TYPE: PRT
<213> ORGANISM: Homo sapiens

<400> SEQUENCE: 71

Ser Thr Tyr Tyr Gly Gly Asp Trp Tyr Phe Asp Tyr
1               5                   10


<210> SEQ ID NO 72
<211> LENGTH: 121
<212> TYPE: PRT
<213> ORGANISM: Homo sapiens

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Gln Gly Arg Val Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Gln Gly Thr Leu Val Thr Val Ser Ser
        115                 120


<210> SEQ ID NO 73
```

<211> LENGTH: 363
<212> TYPE: DNA
<213> ORGANISM: Homo sapiens

<400> SEQUENCE: 73
gaggtgcagc tggttgaatc tggcggagga ctggttcagc ctggcggatc tctgagactg 60
tcttgtgccg ccagcggcta caccttcacc agctacaata tgcactgggt ccgacaggcc 120
cctggacagg gacttgaatg gatgggcgct atctaccctg gcaacggcga cacctcctac 180
aaccagaaat tccagggcag agtgaccctg accgccgaca agtctagcag caccgcctac 240
atggaactga gcagcctgag aagcgaggac accgccgtgt actactgtgc cagaagcacc 300
tactacggcg gcgactggta cttcaacgtg tggggacagg gaaccctggt caccgtttct 360
tct 363

<210> SEQ ID NO 74
<211> LENGTH: 122
<212> TYPE: PRT
<213> ORGANISM: Homo sapiens

<400> SEQUENCE: 74

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asn Asp Tyr
20 25 30

Ala Met His Trp Val Arg Gln Ala Pro Gly Lys Gly Leu Glu Trp Val
35 40 45

Ser Thr Ile Ser Trp Asn Ser Gly Ser Ile Gly Tyr Ala Asp Ser Val
50 55 60

Lys Gly Arg Phe Thr Ile Ser Arg Asp Asn Ala Lys Lys Thr Leu Tyr
65 70 75 80

Leu Gln Met Asn Ser Leu Arg Ala Glu Asp Thr Ala Val Tyr Tyr Cys
85 90 95

Ala Lys Asp Ile Gln Tyr Gly Asn Tyr Tyr Tyr Gly Met Asp Val Trp
100 105 110

Gly Gln Gly Thr Leu Val Thr Val Ser Ser
115 120

<210> SEQ ID NO 75
<211> LENGTH: 366
<212> TYPE: DNA
<213> ORGANISM: Homo sapiens

<400> SEQUENCE: 75
gaagtgcagc tgctggaatc tggcggagga ctggttcaac ctggcggctc tctgagactg 60
tcttgtgccg cttctggctt caccttcaac gactacgcca tgcactgggt ccgacaggcc 120
cctggaaaag gactggaatg ggtgtccacc atcagctgga acagcggctc tatcggctac 180
gccgattccg tgaagggcag attcaccatc tccagagaca acgccaagaa aaccctgtac 240
ctgcagatga acagcctgag agccgaggac accgccgtgt actactgtgc caaggacatc 300
cagtacggca actactacta cggcatggac gtgtggggcc agggaacact ggttaccgtt 360
agctct 366

<210> SEQ ID NO 76
<211> LENGTH: 5
<212> TYPE: PRT
<213> ORGANISM: Homo sapiens

<400> SEQUENCE: 76

Asp Tyr Ala Met His
1 5

<210> SEQ ID NO 77
<211> LENGTH: 17
<212> TYPE: PRT
<213> ORGANISM: Homo sapiens

<400> SEQUENCE: 77

Thr Ile Ser Trp Asn Ser Gly Ser Ile Gly Tyr Ala Asp Ser Val Lys
1 5 10 15

Gly

<210> SEQ ID NO 78
<211> LENGTH: 13
<212> TYPE: PRT
<213> ORGANISM: Homo sapiens

<400> SEQUENCE: 78

Asp Ile Gln Tyr Gly Asn Tyr Tyr Tyr Gly Met Asp Val
1 5 10

<210> SEQ ID NO 79
<211> LENGTH: 122
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asn Asp Tyr
20 25 30

Ala Met His Trp Val Arg Gln Ala Pro Gly Lys Gly Leu Glu Trp Val
35 40 45

Ser Thr Ile Ser Trp Asn Ser Gly Ser Ile Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Gln Tyr Gly Asn Tyr Tyr Tyr Gly Met Asp Val Trp
100 105 110

Gly Gln Gly Thr Leu Val Thr Val Ser Ser
115 120

<210> SEQ ID NO 80
<211> LENGTH: 366
<212> TYPE: DNA
<213> ORGANISM: Homo sapiens

<400> SEQUENCE: 80
gaagtgcagc tgctggaatc tggtggcgga ctggttcagc ctggcggctc tctgagactg 60
tcttgtgctg ccagcggctt caccttcaac gactacgcta tgcactgggt ccgacaggcc 120
cctggcaaag gacttgaatg ggtgtccacc atcagctgga acagcggctc tatcggctac 180
gccgattccg tgaagggcag attcaccatc tccagagaca acagcaagaa caccctgtac 240
ctgcagatga acagcctgag agccgaggac accgccgtgt actactgtgc caaggacatc 300
cagtacggca actactacta cggcatggac gtgtggggcc agggaacact ggttaccgtt 360
agctct 366

<210> SEQ ID NO 81
<211> LENGTH: 122
<212> TYPE: PRT
<213> ORGANISM: Homo sapiens

<400> SEQUENCE: 81

Glu Val Gln Leu Leu Glu Ser Gly Gly Gly Val Val Gln Pro Gly Gly
1 5 10 15

Ser Leu Arg Leu Ser Cys Ala Ala Ser Gly Phe Thr Phe Asn Asp Tyr
20 25 30

Ala Met His Trp Val Arg Gln Ala Pro Gly Lys Gly Leu Glu Trp Val
35 40 45

Ser Thr Ile Ser Trp Asn Ser Gly Ser Ile Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Gln Tyr Gly Asn Tyr Tyr Tyr Gly Met Asp Val Trp
100 105 110

Gly Gln Gly Thr Leu Val Thr Val Ser Ser
115 120

<210> SEQ ID NO 82
<211> LENGTH: 366
<212> TYPE: DNA
<213> ORGANISM: Homo sapiens

<400> SEQUENCE: 82
gaagtgcagc tgctggaatc tggtggcgga gttgttcagc ctggcggctc tctgagactg 60
tcttgtgctg ccagcggctt caccttcaac gactacgcta tgcactgggt ccgacaggcc 120
cctggcaaag gacttgaatg ggtgtccacc atcagctgga acagcggctc tatcggctac 180
gccgattccg tgaagggcag attcaccatc tccagagaca acagcaagaa caccctgtac 240
ctgcagatga acagcctgag agccgaggac accgccgtgt actactgtgc caaggacatc 300
cagtacggca actactacta cggcatggac gtgtggggcc agggaacact ggttaccgtt 360
agctct 366

<210> SEQ ID NO 83
<211> LENGTH: 122
<212> TYPE: PRT
<213> ORGANISM: Homo sapiens

<400> SEQUENCE: 83

Glu Val Gln Leu Leu Glu Ser Gly Gly Gly Val Val Gln Pro Gly Gly
1 5 10 15

Ser Leu Arg Leu Ser Cys Ala Ala Ser Gly Phe Thr Phe Asn Asp Tyr
20 25 30

Ala Met His Trp Val Arg Gln Ala Pro Gly Lys Gly Leu Glu Trp Val
35 40 45

Ser Thr Ile Ser Trp Asn Ser Gly Ser Ile Gly Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gln Tyr Gly Asn Tyr Tyr Tyr Gly Met Asp Tyr Trp
            100                 105                 110

Gly Gln Gly Thr Leu Val Thr Val Ser Ser
        115                 120


<210> SEQ ID NO 84
<211> LENGTH: 366
<212> TYPE: DNA
<213> ORGANISM: Homo sapiens

<400> SEQUENCE: 84

gaagtgcagc tgctggaatc tggtggcgga gttgttcagc ctggcggctc tctgagactg      60

tcttgtgctg ccagcggctt caccttcaac gactacgcta tgcactgggt ccgacaggcc     120

cctggcaaag gacttgaatg ggtgtccacc atcagctgga acagcggctc tatcggctac     180

gccgattccg tgaagggcag attcaccatc tccagagaca acagcaagaa caccctgtac     240

ctgcagatga acagcctgag agccgaggac accgccgtgt actactgtgc caaggacatc     300

cagtacggca actactacta cggcatggac tactggggcc agggaacact ggttaccgtt     360

agctct                                                                366


<210> SEQ ID NO 85
<211> LENGTH: 13
<212> TYPE: PRT
<213> ORGANISM: Homo sapiens

<400> SEQUENCE: 85

Asp Ile Gln Tyr Gly Asn Tyr Tyr Tyr Gly Met Asp Tyr
1               5                   10


<210> SEQ ID NO 86
<211> LENGTH: 448
<212> TYPE: PRT
<213> ORGANISM: Homo sapiens

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Glu Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Gln Gly Arg Val Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

```
Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Glu Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Cys Thr Leu
            340                 345                 350

Pro Pro Ser Gln Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 87
<211> LENGTH: 1344
<212> TYPE: DNA
<213> ORGANISM: Homo sapiens

<400> SEQUENCE: 87

```
caggttcagc tggttcagtc tggcgccgaa gtgaagaaac ctggcagcag cgtgaaggtg     60

tcctgcaagg ctagcggcta cacattcacc agctacaaca tgcactgggt ccgagaggcc    120

cctggacagg gacttgaatg gatgggcgct atctaccctg gcaacggcga cacctcctac    180

aaccagaaat tccagggcag agtgaccctg accgccgaca agtctagcag caccgcctac    240

atggaactga gcagcctgag aagcgaggac accgccgtgt actactgtgc cagaagcacc    300

tactacggcg gcgactggta cttcgactat tggggacagg gaaccctggt caccgtttct    360

tctgctagca ccaagggccc cagcgtgttc cccctggccc cttgcagcag aagcaccagc    420
```

```
gagagcacag ccgccctggg ctgcctggtg gaggactact tccccgagcc cgtgaccgtg    480

tcctggaaca gcggcgctct gaccagcggc gtgcatacct tccccgccgt gctccagagc    540

agcggactgt actccctgag cagcgtggtg accgtgcctt ccagcagcct gggcaccaag    600

acctacacct gcaacgtgga ccacaagccc agcaacacca aggtggacga gagagtggag    660

agcaagtacg gccctccctg cccccccttgc cctgcccccg agttcgaagg cggacctagc    720

gtgttcctgt tcccccccaa gcccaaggac accctgatga tcagcagaac ccccgaggtg    780

acctgcgtgg tggtggacgt gtcccaggag gaccccgagg tccagtttaa ttggtacgtg    840

gacggcgtgg aagtgcataa cgccaagacc aagcccagag aggagcagtt cgccagcacc    900

tacagagtgg tgtccgtgct gaccgtgctg caccaggact ggctgaacgg caaggaatac    960

aagtgcaagg tctccaacaa gggcctgcct agcagcatcg agaagaccat cagcaaggcc   1020

aagggccagc cacgggagcc ccaggtctgc accctgccac ctagccaaga ggagatgacc   1080

aagaaccagg tgtccctgag ctgtgccgtg aaaggcttct atcccagcga tatcgccgtg   1140

gagtgggaga gcaacggcca gcccgagaac aactacaaga ccaccccccc tgtgctggac   1200

agcgacggca gcttcttcct ggtttccaag ctgaccgtgg acaagtccag atggcaggag   1260

ggcaacgtct tcagctgctc cgtgatgcac gaggccctgc acaaccacta cacccagaag   1320

tccctgagcc tgagcctggg caag                                           1344
```

```
<210> SEQ ID NO 88
<211> LENGTH: 213
<212> TYPE: PRT
<213> ORGANISM: Homo sapiens

<400> SEQUENCE: 88

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Ile
            20                  25                  30

His Trp Phe Gln Lys Lys Pro Gly Gln Ala Pro Arg Pro Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Thr Ser Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Lys Lys Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 89
<211> LENGTH: 639
<212> TYPE: DNA
<213> ORGANISM: Homo sapiens

<400> SEQUENCE: 89
gagatcgtgc tgacacagag ccctggcaca ctgtcactgt ctccaggcga gagagccaca 60
ctgagctgta gagccagcag cagcgtgtcc tacatccact ggttccagaa gaagcctgga 120
caggccccta gacctctgat ctacgccaca agcaacctgg ccagcggcat ccctgataga 180
ttcagcggct ctggcagcgg caccgactac acactgacaa tcagcagact ggaacccgag 240
gacttcgccg tgtactactg ccagcagtgg accagcaatc ctcctacatt cggccagggc 300
accaagctgg aaatcaagcg aactgtggct gcaccatctg tcttcatctt cccgccatct 360
gataagaaat tgaaatctgg aactgcctct gttgtgtgcc tgctgaataa cttctatccc 420
agagaggcca aagtacagtg gaaggtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgt 639

<210> SEQ ID NO 90
<211> LENGTH: 444
<212> TYPE: PRT
<213> ORGANISM: Homo sapiens

<400> SEQUENCE: 90

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Glu Tyr Tyr Cys Val Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr

```
        195                 200                 205

Val Ala Pro Thr Glu Cys Ser Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Ala Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Cys Gln
            340                 345                 350

Glu Glu Met Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 91
<211> LENGTH: 1332
<212> TYPE: DNA
<213> ORGANISM: Homo sapiens

<400> SEQUENCE: 91

```
caggctgtgg tcacacaaga gcctagcctg acagtgtctc ctggcggcac agtgaccctg      60

acctgtagat cttctacagg cgccgtgacc accagcaact acgctaattg ggtgcaggag     120

aagcccggcc aggctcctag aggactgatc ggcggaacaa acaagagagc cccttggaca     180

cccgccagat tctctggatc tctgctcggc ggaaaggccg ctctgacaat cactggtgct     240

caggctgagg acgaggccga gtactattgt gtgctgtggt acagcaacct gtgggtgttc     300

ggcggaggca ccaaactgac agttctgggt cagcccaagg cggcgccctc ggtcactctg     360

ttcccgccct cctctgagga gcttcaagcc aacaaggcca cactggtgtg tctcataagt     420

gacttctatc cgggagccgt gacagtggcc tggaaggcag atagcagccc cgtcaaggcg     480

ggagtggaga ccaccacacc ctccaaacaa agcaacaaca agtacgcggc cagcagctac     540

ctgagcctga cgcctgagca gtggaagtcc cacagaagct acagctgcca ggtcacgcat     600

gaagggagca ccgtggagaa gacagtggcc cctacagaat gttcagagag caagtacggc     660

cctccctgcc ccccttgccc tgcccccgag ttcgagggcg gacctagcgt gttcctgttc     720
```

```
ccccccaagc ccaaggacac cctgatgatc agcagaaccc ccgaggtgac ctgcgtggtg    780

gtggacgtgt cccaggagga ccccgaggtc cagtttaatt ggtacgtgga cggcgtggaa    840

gtgcataacg ccaagaccaa gcccagagag gagcagttcg ccagcaccta cagagtggtg    900

tccgtgctga ccgtgctgca ccaggactgg ctgaacggca aggaatacaa gtgcaaggtc    960

tccaacaagg gcctgcctag cagcatcgag aagaccatca gcaaggccaa gggccagcca   1020

cgggagcccc aggtctacac cctgccacct tgtcaagagg agatgaccaa gaaccaggtg   1080

tccctgtggt gtctggtgaa aggcttctat cccagcgata tcgccgtgga gtgggagagc   1140

aacggccagc ccgagaacaa ctacaagacc acccccccctg tgctggacag cgacggcagc   1200

ttcttcctgt actccaagct gaccgtggac aagtccagat ggcaggaggg caacgtcttc   1260

agctgctccg tgatgcacga ggccctgcac aaccactaca cccagaagtc cctgagcctg   1320

agcctgggca ag                                                       1332


<210> SEQ ID NO 92
<211> LENGTH: 223
<212> TYPE: PRT
<213> ORGANISM: Homo sapiens

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Lys Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val
    210                 215                 220


<210> SEQ ID NO 93
<211> LENGTH: 669
<212> TYPE: DNA
<213> ORGANISM: Homo sapiens

<400> SEQUENCE: 93
```

```
gaggtgcagc tggttgaatc tggcggagga ctggttcagc ctggcggatc tctgagactg     60

tcttgtgccg ccagcggctt caccttcaac acctacgcta tgaactgggt ccgaaaggcc    120

cctggcaaag gactggaatg ggtgggaaga atcaggtcca agtacaacaa ctacgccacc    180

tactacgccg acagcgtgaa ggacagattc accatcagca gggacgacag caagaacagc    240

ctgtacctgc agatgaacag cctgaaaacc gaggacaccg ccgtgtacta ctgtgtcaga    300

cacggcaact tcggcaacag ctatgtgtct tggtttgcct actggggcca gggcacactg    360

gtcacagtta gctctgctag caccaagggc cccagcgtgt tccccctggc cccttgcagc    420

agaagcacca gcgagagcac agccgccctg ggctgcctgg tgaaggacta cttccccgag    480

cccgtgaccg tgtcctggaa cagcggcgct ctgaccagcg gcgtgcatac cttccccgcc    540

gtgctccaga gcagcggact gtactccctg agcagcgtgg tgaccgtgcc ttccagcagc    600

ctgggcacca agacctacac ctgcaacgtg gaccacaagc ccagcaacac caaggtggac    660

aagagagtg                                                            669
```

```
<210> SEQ ID NO 94
<211> LENGTH: 449
<212> TYPE: PRT
<213> ORGANISM: Homo sapiens

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Ala Met His Trp Val Arg Glu Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Glu Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
```

```
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Cys Thr
            340                 345                 350

Leu Pro Pro Ser Gln Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 95
<211> LENGTH: 1347
<212> TYPE: DNA
<213> ORGANISM: Homo sapiens

<400> SEQUENCE: 95

```
gaagtgcagc tgctggaatc tggtggcgga ctggttcagc ctggcggctc tctgagactg     60

tcttgtgctg ccagcggctt caccttcaac gactacgcta tgcactgggt ccgagaggcc    120

cctggcaaag gacttgaatg ggtgtccacc atcagctgga acagcggctc tatcggctac    180

gccgattccg tgaagggcag attcaccatc tccagagaca acagcaagaa caccctgtac    240

ctgcagatga acagcctgag agccgaggac accgccgtgt actactgtgc caaggacatc    300

cagtacggca actactacta cggcatggac gtgtggggcc agggaacact ggttaccgtt    360

agctctgcta gcaccaaggg ccccagcgtg ttcccccctgg cccctgcag cagaagcacc    420

agcgagagca cagccgccct gggctgcctg gtggaggact acttccccga gcccgtgacc    480

gtgtcctgga acagcggcgc tctgaccagc ggcgtgcata ccttccccgc cgtgctccag    540

agcagcggac tgtactccct gagcagcgtg gtgaccgtgc cttccagcag cctgggcacc    600

aagacctaca cctgcaacgt ggaccacaag cccagcaaca ccaaggtgga cgagagagtg    660

gagagcaagt acggccctcc ctgccccccct tgccctgccc ccgagttcga aggcggacct    720

agcgtgttcc tgttcccccc caagcccaag gacaccctga tgatcagcag aacccccgag    780

gtgacctgcg tggtggtgga cgtgtcccag gaggaccccg aggtccagtt taattggtac    840

gtggacggcg tggaagtgca taacgccaag accaagccca gagaggagca gttcgccagc    900

acctacagag tggtgtccgt gctgaccgtg ctgcaccagg actggctgaa cggcaaggaa    960
```

```
tacaagtgca aggtctccaa caagggcctg cctagcagca tcgagaagac catcagcaag   1020

gccaagggcc agccacggga gccccaggtc tgcaccctgc cacctagcca agaggagatg   1080

accaagaacc aggtgtccct gagctgtgcc gtgaaaggct tctatcccag cgatatcgcc   1140

gtggagtggg agagcaacgg ccagcccgag aacaactaca agaccacccc ccctgtgctg   1200

gacagcgacg gcagcttctt cctggtttcc aagctgaccg tggacaagtc cagatggcag   1260

gagggcaacg tcttcagctg ctccgtgatg cacgaggccc tgcacaacca ctacacccag   1320

aagtccctga gcctgagcct gggcaag                                      1347
```

<210> SEQ ID NO 96
<211> LENGTH: 214
<212> TYPE: PRT
<213> ORGANISM: Homo sapiens

<400> SEQUENCE: 96

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Lys Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Lys Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 97
<211> LENGTH: 642
<212> TYPE: DNA
<213> ORGANISM: Homo sapiens

<400> SEQUENCE: 97

```
gagatcgtgc tgacacagag ccctggcaca ctgtcactgt ctccaggcga gagagccaca     60

ctgagctgta gagccagcca gagcgtgtcc tcttacctgg cctggtatca gaagaagcct    120

ggacaggctc ccagactgct gatctacgac gccagcaaca gagccacagg catccccgat    180
```

agattcagcg gctctggctc tggcaccgac ttcaccctga caatcagcag actggaaccc 240
gaggacttcg ccgtgtacta ctgccagcag agaagcaact ggcccatcac attcggccag 300
ggcaccaagc tggaaatcaa gcgaactgtg gctgcaccat ctgtcttcat cttcccgcca 360
tctgataaga aattgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 98
<211> LENGTH: 449
<212> TYPE: PRT
<213> ORGANISM: Homo sapiens

<400> SEQUENCE: 98

Glu Val Gln Leu Leu Glu Ser Gly Gly Gly Val Val Gln Pro Gly Gly
1 5 10 15

Ser Leu Arg Leu Ser Cys Ala Ala Ser Gly Phe Thr Phe Asn Asp Tyr
20 25 30

Ala Met His Trp Val Arg Glu Ala Pro Gly Lys Gly Leu Glu Trp Val
35 40 45

Ser Thr Ile Ser Trp Asn Ser Gly Ser Ile Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Gln Tyr Gly Asn Tyr Tyr Tyr Gly Met Asp Tyr Trp
100 105 110

Gly Gln Gly Thr Leu Val Thr Val Ser Ser Ala Ser Thr Lys Gly Pro
115 120 125

Ser Val Phe Pro Leu Ala Pro Cys Ser Arg Ser Thr Ser Glu Ser Thr
130 135 140

Ala Ala Leu Gly Cys Leu Val Glu Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Lys Thr Tyr Thr Cys Asn Val Asp
195 200 205

His Lys Pro Ser Asn Thr Lys Val Asp Glu Arg Val Glu Ser Lys Tyr
210 215 220

Gly Pro Pro Cys Pro Pro Cys Pro Ala Pro Glu Phe Glu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Gln Glu Asp
260 265 270

Pro Glu Val Gln Phe Asn Trp Tyr Val Asp Gly Val Glu Val His Asn
275 280 285

Ala Lys Thr Lys Pro Arg Glu Glu Gln Phe Ala Ser Thr Tyr Arg Val

```
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Cys Thr
            340                 345                 350

Leu Pro Pro Ser Gln Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 99
<211> LENGTH: 1347
<212> TYPE: DNA
<213> ORGANISM: Homo sapiens

<400> SEQUENCE: 99

gaagtgcagc tgctggaatc tggtggcgga gttgttcagc ctggcggctc tctgagactg      60

tcttgtgctg ccagcggctt caccttcaac gactacgcta tgcactgggt ccgagaggcc     120

cctggcaaag gacttgaatg ggtgtccacc atcagctgga acagcggctc tatcggctac     180

gccgattccg tgaagggcag attcaccatc tccagagaca acagcaagaa caccctgtac     240

ctgcagatga acagcctgag agccgaggac accgccgtgt actactgtgc caaggacatc     300

cagtacggca actactacta cggcatggac tactggggcc agggaacact ggttaccgtt     360

agctctgcta gcaccaaggg ccccagcgtg ttccccctgg ccccttgcag cagaagcacc     420

agcgagagca cagccgccct gggctgcctg gtggaggact acttccccga gcccgtgacc     480

gtgtcctgga acagcggcgc tctgaccagc ggcgtgcata ccttccccgc cgtgctccag     540

agcagcggac tgtactccct gagcagcgtg gtgaccgtgc cttccagcag cctgggcacc     600

aagacctaca cctgcaacgt ggaccacaag cccagcaaca ccaaggtgga cgagagagtg     660

gagagcaagt acggccctcc ctgccccccct tgccctgccc ccgagttcga aggcggacct     720

agcgtgttcc tgttcccccc caagcccaag gacaccctga tgatcagcag aacccccgag     780

gtgacctgcg tggtggtgga cgtgtcccag gaggaccccg aggtccagtt taattggtac     840

gtggacggcg tggaagtgca taacgccaag accaagccca gagaggagca gttcgccagc     900

acctacagag tggtgtccgt gctgaccgtg ctgcaccagg actggctgaa cggcaaggaa     960

tacaagtgca aggtctccaa caagggcctg cctagcagca tcgagaagac catcagcaag    1020

gccaagggcc agccacggga gccccaggtc tgcaccctgc cacctagcca agaggagatg    1080

accaagaacc aggtgtccct gagctgtgcc gtgaaaggct tctatcccag cgatatcgcc    1140

gtggagtggg agagcaacgg ccagcccgag aacaactaca agaccacccc ccctgtgctg    1200
```

gacagcgacg gcagcttctt cctggtttcc aagctgaccg tggacaagtc cagatggcag 1260
gagggcaacg tcttcagctg ctccgtgatg cacgaggccc tgcacaacca ctacacccag 1320
aagtccctga gcctgagcct gggcaag 1347

<210> SEQ ID NO 100
<211> LENGTH: 214
<212> TYPE: PRT
<213> ORGANISM: Homo sapiens

<400> SEQUENCE: 100

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Lys Lys Pro Gly Gln Ala Pro Arg Leu Leu Ile
35 40 45

Tyr Asp Ala Ser Asn Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Arg Ser Asn Trp Pro Ile
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Lys Lys Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 101
<211> LENGTH: 642
<212> TYPE: DNA
<213> ORGANISM: Homo sapiens

<400> SEQUENCE: 101
gagatcgtgc tgacacagag ccctggcaca ctgtcactgt ctccaggcga gagagccaca 60
ctgagctgta gagccagcca gagcgtgtcc tcttacctgg cctggtatca gaagaagcct 120
ggacaggctc ccagactgct gatctacgac gccagcaaca gagccacagg catccccgat 180
agattcagcg gctctggctc tggcaccgac ttcaccctga caatcagcag actggaaccc 240
gaggacttcg ccgtgtacta ctgccagcag agaagcaact ggcccatcac attcggccag 300
ggcaccaagc tggaaatcaa gcgaactgtg gctgcaccat ctgtcttcat cttcccgcca 360
tctgataaga aattgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 102
<211> LENGTH: 214
<212> TYPE: PRT
<213> ORGANISM: Homo sapiens

<400> SEQUENCE: 102

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Arg Ser Asn Trp Pro Ile
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 103
<211> LENGTH: 642
<212> TYPE: DNA
<213> ORGANISM: Homo sapiens

<400> SEQUENCE: 103
gagatcgtgc tgacacagag ccctggcaca ctgtcactgt ctccaggcga gagagccaca 60
ctgagctgta gagccagcca gagcgtgtcc tcttacctgg cctggtatca gcagaagcct 120
ggacaggctc ccagactgct gatctacgac gccagcaaca gagccacagg catccccgat 180
agattcagcg gctctggctc tggcaccgac ttcaccctga caatcagcag actggaaccc 240
gaggacttcg ccgtgtacta ctgccagcag agaagcaact ggcccatcac attcggccag 300
ggcaccaagc tggaaatcaa gcgaactgtg gctgcaccat ctgtcttcat cttcccgcca 360
tctgatgagc agttgaaatc tggaactgcc tctgttgtgt gcctgctgaa taacttctat 420

```
cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642


<210> SEQ ID NO 104
<211> LENGTH: 449
<212> TYPE: PRT
<213> ORGANISM: Homo sapiens

<400> SEQUENCE: 104

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gln Tyr Gly Asn Tyr Tyr Tyr Gly Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Ala Ser Ser Ile Glu Lys
                325                 330                 335
```

```
Thr Ile Ser Lys Ala Lys Gly Gln Pro Arg Glu Pro Gln Val Cys Thr
            340                 345                 350

Leu Pro Pro Ser Gln Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 105
<211> LENGTH: 1347
<212> TYPE: DNA
<213> ORGANISM: Homo sapiens

<400> SEQUENCE: 105

gaagtgcagc tgctggaatc tggtggcgga gttgttcagc ctggcggctc tctgagactg      60

tcttgtgctg ccagcggctt caccttcaac gactacgcta tgcactgggt ccgacaggcc     120

cctggcaaag gacttgaatg ggtgtccacc atcagctgga acagcggctc tatcggctac     180

gccgattccg tgaagggcag attcaccatc tccagagaca acagcaagaa caccctgtac     240

ctgcagatga acagcctgag agccgaggac accgccgtgt actactgtgc caaggacatc     300

cagtacggca actactacta cggcatggac tactggggcc agggaacact ggttaccgtt     360

agctctgcta gcaccaaggg ccccagcgtg ttccccctgg ccccttgcag cagaagcacc     420

agcgagagca cagccgccct gggctgcctg gtgaaggact acttccccga gcccgtgacc     480

gtgtcctgga acagcggcgc tctgaccagc ggcgtgcata ccttccccgc cgtgctccag     540

agcagcggac tgtactccct gagcagcgtg gtgaccgtgc cttccagcag cctgggcacc     600

aagacctaca cctgcaacgt ggaccacaag cccagcaaca ccaaggtgga caagagagtg     660

gagagcaagt acggccctcc ctgccccccct tgccctgccc ccgagttcga gggcggacct     720

agcgtgttcc tgttcccccc caagcccaag gacaccctga tgatcagcag aacccccgag     780

gtgacctgcg tggtggtgga cgtgtcccag gaggaccccg aggtccagtt taattggtac     840

gtggacggcg tggaagtgca taacgccaag accaagccca gagaggagca gttcaacagc     900

acctacagag tggtgtccgt gctgaccgtg ctgcaccagg actggctgaa cggcaaggaa     960

tacaagtgca aggtctccaa caagggcctg gccagcagca tcgagaagac catcagcaag    1020

gccaagggcc agccacggga gccccaggtc tgcaccctgc cacctagcca agaggagatg    1080

accaagaacc aggtgtccct gagctgtgcc gtgaaaggct tctatcccag cgatatcgcc    1140

gtggagtggg agagcaacgg ccagcccgag aacaactaca agaccacccc ccctgtgctg    1200

gacagcgacg gcagcttctt cctggtttcc aagctgaccg tggacaagtc cagatggcag    1260

gagggcaacg tcttcagctg ctccgtgatg cacgaggccc tgcacaacca ctacacccag    1320

aagtccctga gcctgagcct gggcaag                                        1347


<210> SEQ ID NO 106
```

<211> LENGTH: 215
<212> TYPE: PRT
<213> ORGANISM: Homo sapiens

<400> SEQUENCE: 106

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Glu Tyr Tyr Cys Val Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 107
<211> LENGTH: 645
<212> TYPE: DNA
<213> ORGANISM: Homo sapiens

<400> SEQUENCE: 107

```
caggctgtgg tcacacaaga gcctagcctg acagtgtctc ctggcggcac agtgaccctg      60

acctgtagat cttctacagg cgccgtgacc accagcaact acgctaattg ggtgcagcag     120

aagcccggcc aggctcctag aggactgatc ggcggaacaa acaagagagc cccttggaca     180

cccgccagat tctctggatc tctgctcggc ggaaaggccg ctctgacaat cactggtgct     240

caggctgagg acgaggccga gtactattgt gtgctgtggt acagcaacct gtgggtgttc     300

ggcggaggca ccaaactgac agttctgggt cagcccaagg cggcgccctc ggtcactctg     360

ttcccgccct cctctgagga gcttcaagcc aacaaggcca cactggtgtg tctcataagt     420

gacttctatc cgggagccgt gacagtggcc tggaaggcag atagcagccc cgtcaaggcg     480

ggagtggaga ccaccacacc ctccaaacaa agcaacaaca agtacgcggc cagcagctac     540

ctgagcctga cgcctgagca gtggaagtcc cacagaagct acagctgcca ggtcacgcat     600

gaagggagca ccgtggagaa gacagtggcc cctacagaat gttca                     645
```

<210> SEQ ID NO 108
<211> LENGTH: 452
<212> TYPE: PRT
<213> ORGANISM: Homo sapiens

<400> SEQUENCE: 108

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Ala Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Gln Glu Glu Met Thr Lys Asn Gln Val
        355                 360                 365

Ser Leu Trp Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450


<210> SEQ ID NO 109
<211> LENGTH: 1356
<212> TYPE: DNA
<213> ORGANISM: Homo sapiens

<400> SEQUENCE: 109

gaggtgcagc tggttgaatc tggcggagga ctggttcagc ctggcggatc tctgagactg     60

tcttgtgccg ccagcggctt caccttcaac acctacgcta tgaactgggt ccgacaggcc    120

cctggcaaag gactggaatg ggtgggaaga atcaggtcca agtacaacaa ctacgccacc    180

tactacgccg acagcgtgaa ggacagattc accatcagca gggacgacag caagaacagc    240

ctgtacctgc agatgaacag cctgaaaacc gaggacaccg ccgtgtacta ctgtgtcaga    300

cacggcaact tcggcaacag ctatgtgtct tggtttgcct actggggcca gggcacactg    360

gtcacagtta gctctgctag caccaagggc cccagcgtgt tcccccctggc cccttgcagc    420

agaagcacca gcgagagcac agccgccctg ggctgcctgg tgaaggacta cttccccgag    480

cccgtgaccg tgtcctggaa cagcggcgct ctgaccagcg gcgtgcatac cttccccgcc    540

gtgctccaga gcagcggact gtactccctg agcagcgtgg tgaccgtgcc ttccagcagc    600

ctgggcacca agacctacac ctgcaacgtg gaccacaagc ccagcaacac caaggtggac    660

aagagagtgg agagcaagta cggccctccc tgcccccctt gccctgcccc cgagttcgag    720

ggcggaccta gcgtgttcct gttccccccc aagcccaagg acaccctgat gatcagcaga    780

acccccgagg tgacctgcgt ggtggtggac gtgtcccagg aggaccccga ggtccagttt    840

aattggtacg tggacggcgt ggaagtgcat aacgccaaga ccaagcccag agaggagcag    900

ttcaacagca cctacagagt ggtgtccgtg ctgaccgtgc tgcaccagga ctggctgaac    960

ggcaaggaat acaagtgcaa ggtctccaac aagggcctgg ccagcagcat cgagaagacc   1020

atcagcaagg ccaagggcca gccacgggag ccccaggtct acaccctgcc accttgtcaa   1080

gaggagatga ccaagaacca ggtgtccctg tggtgtctgg tgaaaggctt ctatcccagc   1140

gatatcgccg tggagtggga gagcaacggc cagcccgaga acaactacaa gaccaccccc   1200

cctgtgctgg acagcgacgg cagcttcttc ctgtactcca agctgaccgt ggacaagtcc   1260

agatggcagg agggcaacgt cttcagctgc tccgtgatgc acgaggccct gcacaaccac   1320

tacacccaga agtccctgag cctgagcctg ggcaag                              1356


<210> SEQ ID NO 110
<211> LENGTH: 214
<212> TYPE: PRT
<213> ORGANISM: Homo sapiens

<400> SEQUENCE: 110

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Ser Tyr
20 25 30

Leu Ala Trp Tyr Gln Lys Lys Pro Gly Gln Ala Pro Arg Leu Leu Ile
35 40 45

Tyr Asp Ala Ser Asn Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Arg Ser Asn Trp Pro Ile
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 111
<211> LENGTH: 642
<212> TYPE: DNA
<213> ORGANISM: Homo sapiens

<400> SEQUENCE: 111
gagatcgtgc tgacacagag ccctggcaca ctgtcactgt ctccaggcga gagagccaca 60
ctgagctgta gagccagcca gagcgtgtcc tcttacctgg cctggtatca gaagaagcct 120
ggacaggctc ccagactgct gatctacgac gccagcaaca gagccacagg catccccgat 180
agattcagcg gctctggctc tggcaccgac ttcaccctga caatcagcag actggaaccc 240
gaggacttcg ccgtgtacta ctgccagcag agaagcaact ggcccatcac attcggccag 300
ggcaccaagc tggaaatcaa gcgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 112
<211> LENGTH: 449
<212> TYPE: PRT
<213> ORGANISM: Homo sapiens

<400> SEQUENCE: 112

Glu Val Gln Leu Leu Glu Ser Gly Gly Gly Val Val Gln Pro Gly Gly

-continued

```
1               5                   10                  15

Ser Leu Arg Leu Ser Cys Ala Ala Ser Gly Phe Thr Phe Asn Asp Tyr
            20                  25                  30

Ala Met His Trp Val Arg Glu Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gln Tyr Gly Asn Tyr Tyr Tyr Gly Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Ala Ser Ser Ile Glu Lys
                325                 330                 335

Thr Ile Ser Lys Ala Lys Gly Gln Pro Arg Glu Pro Gln Val Cys Thr
            340                 345                 350

Leu Pro Pro Ser Gln Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Glu Gly Asn Val Phe Ser Cys Ser Val Met His Glu
            420                 425                 430
```

Ala Leu His Asn His Tyr Thr Gln Lys Ser Leu Ser Leu Ser Leu Gly
435 440 445

Lys

<210> SEQ ID NO 113
<211> LENGTH: 1347
<212> TYPE: DNA
<213> ORGANISM: Homo sapiens

<400> SEQUENCE: 113
gaagtgcagc tgctggaatc tggtggcgga gttgttcagc ctggcggctc tctgagactg 60
tcttgtgctg ccagcggctt caccttcaac gactacgcta tgcactgggt ccgagaggcc 120
cctggcaaag gacttgaatg ggtgtccacc atcagctgga acagcggctc tatcggctac 180
gccgattccg tgaagggcag attcaccatc tccagagaca acagcaagaa caccctgtac 240
ctgcagatga acagcctgag agccgaggac accgccgtgt actactgtgc caaggacatc 300
cagtacggca actactacta cggcatggac tactggggcc agggaacact ggttaccgtt 360
agctctgcta gcaccaaggg ccccagcgtg ttccccctgg ccccttgcag cagaagcacc 420
agcgagagca cagccgccct gggctgcctg gtgaaggact acttccccga gcccgtgacc 480
gtgtcctgga acagcggcgc tctgaccagc ggcgtgcata ccttccccgc cgtgctccag 540
agcagcggac tgtactccct gagcagcgtg gtgaccgtgc cttccagcag cctgggcacc 600
aagacctaca cctgcaacgt ggaccacaag cccagcaaca ccaaggtgga caagagagtg 660
gagagcaagt acggccctcc ctgccccccct tgccctgccc ccgagttcga gggcggacct 720
agcgtgttcc tgttcccccc caagcccaag gacaccctga tgatcagcag aacccccgag 780
gtgacctgcg tggtggtgga cgtgtcccag gaggaccccg aggtccagtt taattggtac 840
gtggacggcg tggaagtgca taacgccaag accaagccca gagaggagca gttcaacagc 900
acctacagag tggtgtccgt gctgaccgtg ctgcaccagg actggctgaa cggcaaggaa 960
tacaagtgca aggtctccaa caagggcctg gccagcagca tcgagaagac catcagcaag 1020
gccaagggcc agccacggga gccccaggtc tgcaccctgc cacctagcca agaggagatg 1080
accaagaacc aggtgtccct gagctgtgcc gtgaaaggct tctatcccag cgatatcgcc 1140
gtggagtggg agagcaacgg ccagcccgag aacaactaca agaccacccc ccctgtgctg 1200
gacagcgacg gcagcttctt cctggtttcc aagctgaccg tggacaagtc cagatggcag 1260
gagggcaacg tcttcagctg ctccgtgatg cacgaggccc tgcacaacca ctacacccag 1320
aagtccctga gcctgagcct gggcaag 1347

<210> SEQ ID NO 114
<211> LENGTH: 215
<212> TYPE: PRT
<213> ORGANISM: Homo sapiens

<400> SEQUENCE: 114

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Gly Gln Ala Pro Arg Gly
35 40 45

Leu Ile Gly Gly Thr Asn Lys Arg Ala Pro Trp Thr Pro Ala Arg Phe
50 55 60

```
Ser Gly Ser Leu Leu Gly Gly Lys Ala Ala Leu Thr Ile Thr Gly Ala
65                  70                  75                  80

Gln Ala Glu Asp Glu Ala Glu Tyr Tyr Cys Val Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 115
<211> LENGTH: 645
<212> TYPE: DNA
<213> ORGANISM: Homo sapiens

<400> SEQUENCE: 115

caggctgtgg tcacacaaga gcctagcctg acagtgtctc ctggcggcac agtgaccctg      60

acctgtagat cttctacagg cgccgtgacc accagcaact acgctaattg ggtgcaggag     120

aagcccggcc aggctcctag aggactgatc ggcggaacaa acaagagagc cccttggaca     180

cccgccagat tctctggatc tctgctcggc ggaaaggccg ctctgacaat cactggtgct     240

caggctgagg acgaggccga gtactattgt gtgctgtggt acagcaacct gtgggtgttc     300

ggcggaggca ccaaactgac agttctgggt cagcccaagg cggcgccctc ggtcactctg     360

ttcccgccct cctctgagga gcttcaagcc aacaaggcca cactggtgtg tctcataagt     420

gacttctatc cgggagccgt gacagtggcc tggaaggcag atagcagccc cgtcaaggcg     480

ggagtggaga ccaccacacc ctccaaacaa agcaacaaca agtacgcggc cagcagctac     540

ctgagcctga cgcctgagca gtggaagtcc cacagaagct acagctgcca ggtcacgcat     600

gaagggagca ccgtggagaa gacagtggcc cctacagaat gttca                     645


<210> SEQ ID NO 116
<211> LENGTH: 452
<212> TYPE: PRT
<213> ORGANISM: Homo sapiens

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Lys Ala Pro Gly Lys Gly Leu Glu Trp Val
        35                  40                  45

Gly Arg Ile Arg Ser Lys Tyr Asn Asn Tyr Ala Thr Tyr Tyr Ala Asp
```

```
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Ala Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Gln Glu Glu Met Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 117

<211> LENGTH: 1356
<212> TYPE: DNA
<213> ORGANISM: Homo sapiens

<400> SEQUENCE: 117

```
gaggtgcagc tggttgaatc tggcggagga ctggttcagc ctggcggatc tctgagactg     60

tcttgtgccg ccagcggctt caccttcaac acctacgcta tgaactgggt ccgaaaggcc    120

cctggcaaag gactggaatg ggtgggaaga atcaggtcca agtacaacaa ctacgccacc    180

tactacgccg acagcgtgaa ggacagattc accatcagca gggacgacag caagaacagc    240

ctgtacctgc agatgaacag cctgaaaacc gaggacaccg ccgtgtacta ctgtgtcaga    300

cacggcaact tcggcaacag ctatgtgtct tggtttgcct actggggcca gggcacactg    360

gtcacagtta gctctgctag caccaagggc cccagcgtgt tccccctggc cccttgcagc    420

agaagcacca gcgagagcac agccgccctg ggctgcctgg tgaaggacta cttccccgag    480

cccgtgaccg tgtcctggaa cagcggcgct ctgaccagcg gcgtgcatac cttccccgcc    540

gtgctccaga gcagcggact gtactccctg agcagcgtgg tgaccgtgcc ttccagcagc    600

ctgggcacca agacctacac ctgcaacgtg gaccacaagc ccagcaacac caaggtggac    660

aagagagtgg agagcaagta cggccctccc tgccccccctt gccctgcccc cgagttcgag    720

ggcggaccta gcgtgttcct gttccccccc aagcccaagg acaccctgat gatcagcaga    780

acccccgagg tgacctgcgt ggtggtggac gtgtcccagg aggaccccga ggtccagttt    840

aattggtacg tggacggcgt ggaagtgcat aacgccaaga ccaagcccag agaggagcag    900

ttcaacagca cctacagagt ggtgtccgtg ctgaccgtgc tgcaccagga ctggctgaac    960

ggcaaggaat acaagtgcaa ggtctccaac aagggcctgg ccagcagcat cgagaagacc   1020

atcagcaagg ccaagggcca gccacgggag ccccaggtct acaccctgcc accttgtcaa   1080

gaggagatga ccaagaacca ggtgtccctg tggtgtctgg tgaaaggctt ctatcccagc   1140

gatatcgccg tggagtggga gagcaacggc cagcccgaga acaactacaa gaccaccccc   1200

cctgtgctgg acagcgacgg cagcttcttc ctgtactcca agctgaccgt ggacaagtcc   1260

agatggcagg agggcaacgt cttcagctgc tccgtgatgc acgaggccct gcacaaccac   1320

tacacccaga agtccctgag cctgagcctg ggcaag                              1356
```

<210> SEQ ID NO 118
<211> LENGTH: 214
<212> TYPE: PRT
<213> ORGANISM: Homo sapiens

<400> SEQUENCE: 118

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Lys Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Lys Leu Glu Ile Lys Arg Thr Val Ala Ala
```

```
            100                 105                 110

Pro Ser Val Phe Ile Phe Pro Pro Ser Asp Lys Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 119
<211> LENGTH: 642
<212> TYPE: DNA
<213> ORGANISM: Homo sapiens

<400> SEQUENCE: 119

gagatcgtgc tgacacagag ccctggcaca ctgtcactgt ctccaggcga gagagccaca      60

ctgagctgta gagccagcca gagcgtgtcc tcttacctgg cctggtatca gaagaagcct     120

ggacaggctc ccagactgct gatctacgac gccagcaaca gagccacagg catccccgat     180

agattcagcg gctctggctc tggcaccgac ttcaccctga caatcagcag actggaaccc     240

gaggacttcg ccgtgtacta ctgccagcag agaagcaact ggcccatcac attcggccag     300

ggcaccaagc tggaaatcaa gcgaactgtg gctgcaccat ctgtcttcat cttcccgcca     360

tctgataaga aattgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 120
<211> LENGTH: 449
<212> TYPE: PRT
<213> ORGANISM: Homo sapiens

<400> SEQUENCE: 120

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asn Asp Tyr
            20                  25                  30

Ala Met His Trp Val Arg Glu Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Asp Ile Gln Tyr Gly Asn Tyr Tyr Tyr Gly Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Glu Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Ala Ser Ser Ile Glu Lys
                325                 330                 335

Thr Ile Ser Lys Ala Lys Gly Gln Pro Arg Glu Pro Gln Val Cys Thr
            340                 345                 350

Leu Pro Pro Ser Gln Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 121
<211> LENGTH: 1347
<212> TYPE: DNA
<213> ORGANISM: Homo sapiens

<400> SEQUENCE: 121

```
gaagtgcagc tgctggaatc tggtggcgga gttgttcagc ctggcggctc tctgagactg      60

tcttgtgctg ccagcggctt caccttcaac gactacgcta tgcactgggt ccgagaggcc     120
```

```
cctggcaaag gacttgaatg ggtgtccacc atcagctgga acagcggctc tatcggctac    180
gccgattccg tgaagggcag attcaccatc tccagagaca acagcaagaa caccctgtac    240
ctgcagatga acagcctgag agccgaggac accgccgtgt actactgtgc caaggacatc    300
cagtacggca actactacta cggcatggac tactggggcc agggaacact ggttaccgtt    360
agctctgcta gcaccaaggg ccccagcgtg ttcccccctgg ccccttgcag cagaagcacc    420
agcgagagca cagccgccct gggctgcctg gtggaggact acttccccga gcccgtgacc    480
gtgtcctgga acagcggcgc tctgaccagc ggcgtgcata ccttccccgc cgtgctccag    540
agcagcggac tgtactccct gagcagcgtg gtgaccgtgc cttccagcag cctgggcacc    600
aagacctaca cctgcaacgt ggaccacaag cccagcaaca ccaaggtgga cgagagagtg    660
gagagcaagt acggccctcc ctgccccccct tgccctgccc ccgagttcga aggcggacct    720
agcgtgttcc tgttcccccc caagcccaag gacaccctga tgatcagcag aacccccgag    780
gtgacctgcg tggtggtgga cgtgtcccag gaggaccccg aggtccagtt taattggtac    840
gtggacggcg tggaagtgca taacgccaag accaagccca gagaggagca gttcaacagc    900
acctacagag tggtgtccgt gctgaccgtg ctgcaccagg actggctgaa cggcaaggaa    960
tacaagtgca aggtctccaa caagggcctg gccagcagca tcgagaagac catcagcaag   1020
gccaagggcc agccacggga gccccaggtc tgcaccctgc cacctagcca agaggagatg   1080
accaagaacc aggtgtccct gagctgtgcc gtgaaaggct tctatcccag cgatatcgcc   1140
gtggagtggg agagcaacgg ccagcccgag aacaactaca agaccacccc ccctgtgctg   1200
gacagcgacg gcagcttctt cctggtttcc aagctgaccg tggacaagtc cagatggcag   1260
gagggcaacg tcttcagctg ctccgtgatg cacgaggccc tgcacaacca ctacacccag   1320
aagtccctga gcctgagcct gggcaag                                       1347
```

```
<210> SEQ ID NO 122
<211> LENGTH: 109
<212> TYPE: PRT
<213> ORGANISM: Mus musculus

<400> SEQUENCE: 122

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105


<210> SEQ ID NO 123
<211> LENGTH: 125
<212> TYPE: PRT
<213> ORGANISM: Mus musculus

<400> SEQUENCE: 123
```

-continued

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

DEVELOPMENT OF DRUG THERAPEUTIC AGENT CONTAINING ADAPTOR AND USE THEREOF

CROSS REFERENCE TO RELATED APPLICATIONS

This application is a national stage application under 35 U.S.C. § 371 of International Application No. PCT/CN2021/114847, filed internationally on Aug. 26, 2021, which claims priority to Chinese Application No. 202010873215.X filed on Aug. 26, 2020. The contents of the above patent applications are incorporated by reference herein in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 166102001400SEQLIST.TXT, date recorded: Feb. 24, 2023, size: 130,886 bytes).

TECHNICAL FIELD

The present disclosure relates to a bispecific antibody and use thereof, and particularly to a bispecific antibody binding to CD20 and CD3 and use thereof.

BACKGROUND ART

CD20 is a glycosylated membrane protein expressed on the surface of B lymphocytes, and human B cells express the CD20 antigen throughout nearly the entire differentiation cycle except for precursor B cells and terminal plasma cells (Tedder et al. J. Immunol. 135(2): 973-979, 1985). CD20 is also a B-cell tumor-associated antigen and expressed in more than 95% of B-cell non-Hodgkin lymphoma (B-NHL) and other B-cell malignant tumors (Anderson et al. Blood 63(6): 1424-1433, 1984). The CD20-specific chimeric antibody Rituximab had been approved in 1997. The 5-year mean survival rate of patients who receive combination treatment of Rituximab and other drugs can reach 60-70%. The second-generation CD20-specific antibody Ofatumumab (Teeling et al. Blood 104(6): 1793-800, 2004) and the third-generation CD20-specific antibodies, such as obinutuzumab and Ocrelizumab, have been developed for the treatment of chronic lymphocytic leukemia or multiple sclerosis. Although the CD20-specific monoclonal antibodies are effective to most patients with B-NHL, more than 10% of patients are primary and intractable. In addition, about 30-40% of patients cured by Rituximab will suffer from recrudesce within 2-3 years and become resistant to the existing treatment, and has a mean survival time of only 6.3 months. Therefore, it is urgent to develop a therapeutic drug with a novel mechanism for the needs of these patients.

A T-cell bispecific antibody (or also referred to as a T-cell adaptor) is a special antibody molecule that is artificially constructed, of which one end (antigen arm) recognizes an antigen on the surface of a target cell and the other end (CD3 arm) binds to the CD3 receptor of a T cell. By using an antibody targeting the CD3ε chain, CD3 on T cells is aggregated in a manner similar to TCR/peptide/HLA, so as to activate T cells and kill tumors Killing of tumor cells by bispecific antibodies was reported in 1980s (Nature. 1985 Apr. 18-24; 314 (6012): 628-31; Nature. 1985 Jul. 25-31; 316 (6026): 354-6), and in 2005, Gall et al. reported killing Rituximab-resistant tumor cells by using a CD20×CD3 bispecific antibody (2005 Experimental Hematology 33: 452) Similar reports include a bispecific antibody Bi20/FBTA05 constructed by Stanglmaier et al. from mouse and rat IgG (Int. J. Cancer: 123, 1181, 2008), a novel DVD-Ig antibody developed by Wu et al. (Nat Biotechnol. 25: 1290-1297, 2007), a CD20-TDB bispecific antibody developed by Sun et al. based on the CD3 antibody UCHT1 (Science translational medicine. 2015; 7: 287ra270-287ra270), REGN1979 developed by Smith based on VelocImmune mice (Clin Trans Immunol. 2015; 4: e31), etc.

A CD20×CD3 bispecific molecule is a T-cell bispecific (TCB) antibody targeting CD20 expressed on a B cell and the CD3ε chain (CD3e) present on a T cell. Mechanism of action of the CD20×CD3 bispecific molecule includes simultaneous binding to CD20+ B cells and CD3+ T cells to induce the activation of T cells and the T cell-mediated B cell killing.

During a normal immune response, TCR binds, with low affinity (about 1-100 μM), to an exogenous peptide-human leukocyte antigen (HLA) complexes on transfected or mutant cells and conducts a activation signal into the nucleus through CD3, so as to activate the expression of a transcription factor and its downstream proteins (a cytokine, a granzyme, perforin, etc.), and the strength of the signal generated by the TCR complex will determine the fate of T cells. The ε, γ, δ, and ζ subunits of the signal transduction complex associate with each other to form a CD3ε-γ heterodimer, a CD3ε-δ heterodimer, and a CD3ζ-ζ homodimer. However, most of the early developed CD3 bispecific antibodies based on a few murine antibodies such as OKT3, L2K, UCHT1, and TR66 with high affinity Through clinical studies, it is found that too high affinity of a CD3-specific antibody will lead to overactivation of T cells and release of a large number of cytokines to form cytokine storm syndrome; and meanwhile, high affinity also leads to the enrichment of bispecific antibodies in secondary lymphoid organs to reduce the exposure in tumor tissues. The Fcγ receptor binding ability of the Fc portion of an antibody is another important factor affecting drug safety, because the Fcγ receptors are expressed in many normal tissues, after a bispecific antibody to the Fcγ receptor on the cell membrane through Fc, the cross-linking and activation of the CD3 receptor bound to the other end will be caused by the aggregation of the Fcγ receptor, resulting in severe off-target toxicity. For example, the early approved catumaxomab triggers rapid release of cytokines due to the binding of the Fc fragment to the Fcγ receptor expressed by liver Kupffer cells. The human IgG2 subtype or IgG4 subtype with weak Fcγ receptor binding ability is used, or further amino acids at corresponding sites on CH2 are substituted, e.g., Armour et al. substitute the 233rd site to the 236th site (EU sequence serial number) on IgG1 and IgG4 with a corresponding IgG2 sequence to reduce the binding to the Fcγ receptor (Eur. J. Immunol. 1999), Newman et al. introduce mutant Ser228Pro and Leu235Glu into IgG4 to stabilize the IgG4 structure and reduce the binding to the Fcγ receptor at the same time (Clin Immunol. 2001), and Idusogie et al. have found that the substitution of Asp270, Lys322, Pro329 or Pro331 with Ala can reduce the binding of IgG1 to the complement C1q (J Immunol. 2000).

SUMMARY OF THE INVENTION

In order to solve the problems in the prior art, the present disclosure provides a novel CD2O-CD3 κλ bispecific antibody, which adopts a full-length IgG configuration. Through the introduction of charge and optimization of affinity, the κλ bispecific antibody can be preferentially localized to a $CD20^+$ tumor tissue, recruit and activate T cells at low concentration to effectively kill target cells, will not activate T cells in a case that there is no target cell; and meanwhile, the κλ bispecific antibody will not bind to receptors such as FcγRI, FcγRIIA, and FcγRIIIA, reducing the risk of cytokine storm. Efficacy tests verify that an extremely low dose of novel CD20-CD3 κλ bispecific antibody can inhibit the tumor growth and effectively inhibit the growth of transplantation tumors in immune reconstituted mice. Toxicology studies in cynomolgus monkeys also reveal that the novel CD20-CD3 κλ bispecific antibody is well tolerated by the animals and can effectively eliminate B cells under low-dose conditions, and the efficacy and safety of the novel CD20-CD3 κλ bispecific antibody are better than those of similar antibodies.

Therefore, in an aspect, the present disclosure provides a bispecific antibody or an antigen-binding portion thereof.

In an aspect, the present disclosure provides a nucleic acid encoding the bispecific antibody or the antigen-binding portion thereof of the aforementioned aspect.

In an aspect, the present disclosure provides a vector containing the nucleic acid of the aforementioned aspect.

In an aspect, the present disclosure provides a cell containing the nucleic acid or the vector of the aforementioned aspect.

According to the antibody or the antigen-binding portion thereof of any one of the aforementioned aspects, the antibody or the antigen-binding portion thereof is humanized.

In an aspect, the present disclosure provides a pharmaceutical composition or kit containing the antibody or the antigen-binding portion thereof or the nucleic acid encoding the antibody or the antigen-binding portion thereof of any one of the aforementioned aspects and a pharmaceutically acceptable carrier.

In an aspect, the present disclosure provides an antibody-drug conjugate containing the antibody or the antigen-binding portion thereof of any one of the aforementioned aspects, or a bispecific or multispecific molecule that is covalently attached to a therapeutic moiety.

In an aspect, the present disclosure provides a method for treating a CD20-associated disease, which includes the following steps: administering a therapeutically effective amount of antibody or antigen-binding fragment thereof, nucleic acid, vector, cell and/or pharmaceutical composition of any one of the aforementioned aspects to a mammal.

In an aspect, the present disclosure provides use of the antibody or the antigen-binding fragment thereof, the nucleic acid, the vector, the cell and/or the pharmaceutical composition of any one of the aforementioned aspects in the preparation of a drug or kit for treating a CD20-associated disease in a mammal The antibody of the present disclosure can be used in a variety of applications such as detection of CD20 protein, and diagnosis, treatment or prevention of CD20-associated diseases.

BRIEF DESCRIPTION OF THE DRAWINGS

FIG. 9 shows the killing activity of different CD20×CD3 antibody combinations to Raji cells and the activation of T cells, wherein FIG. 9A shows TDCC killing effects mediated by different CD20×CD3 antibody combination; FIG. 9B shows that the CD20×CD3 antibody combinations can stimulate upregulation of T cell activation markers CD69 and CD25 during TDCC killing

FIG. 20 shows the killing of Nalm-6 cells and the activation of T cells by a CD20×CD3 κλ bispecific antibody, wherein FIG. 20A shows the killing of Nalm-6 cells, and FIG. 20B shows the activation of T cells.

FIG. 21 shows the killing of TMD-8 cells and the activation of T cells by a CD20×CD3 κλ bispecific antibody, wherein FIG. 21A shows the killing of TMD-8 cells, and FIG. 21B shows the activation of T cells.

FIG. 22 shows the killing of Toledo cells and the activation of T cells by a CD20×CD3 κλ bispecific antibody, wherein FIG. 22A shows the killing of Toledo cells, and FIG. 22B shows the activation of T cells.

FIG. 24 to FIG. 26 show that a CD20×CD3 κλ bispecific antibody activates the release of cytokines, wherein FIG. 24 shows the TDCC activity of the CD20×CD3 κλ bispecific antibody to Raji cells and the activation of T cells in the process; FIG. 25 shows the elimination of autologous B cells by the CD20×CD3 κλ bispecific antibody and the activation of T cells in the process; and FIG. 26 shows the release of related cytokines during killing of Raji cells and elimination of autologous B cells.

FIG. 28 and FIG. 29 show an inhibiting effect of a CD20×CD3 κλ bispecific antibody on immunodeficient mouse models of subcutaneous transplantation tumor that are inoculated with human PBMCs and Raji, wherein FIG. 29 shows the comparison of efficacies of low-dose groups.

DETAILED DESCRIPTION OF THE INVENTION

I. Definitions

Figure 1:
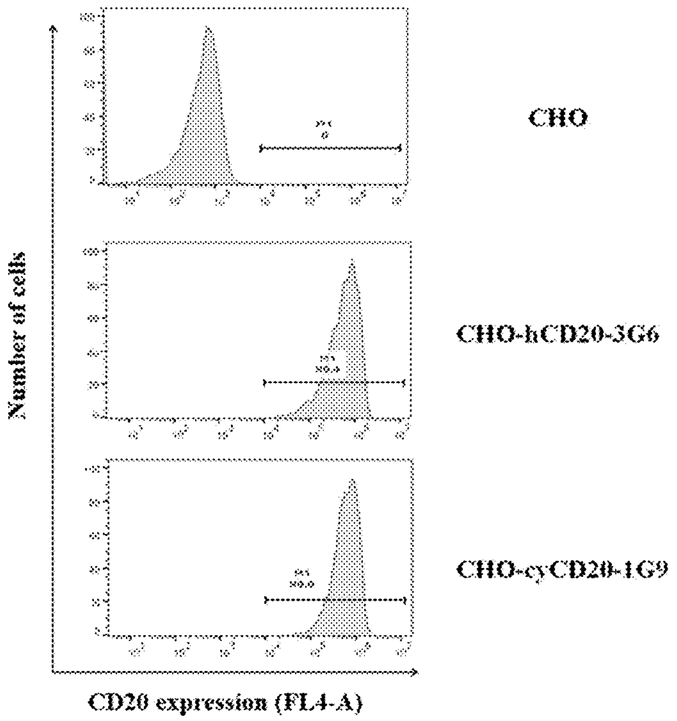
FIG. 1 shows flow cytometry results of human and monkey CD20 stably transfected cells, both the human CD20 stably transfected cells (CHO-hCD20-3G6) and the monkey CD20 stably transfected cells (CHO-cyCD20-1G9) expressing high levels of CD20.

In the present disclosure, unless otherwise specified, scientific and technical terms used herein have the meanings commonly understood by those skilled in the art. Moreover, protein and nucleic acid chemistry, molecular biology, cell and tissue culture, microbiology, and immunology-related terms and laboratory procedures used herein are terms and conventional procedures widely used in corresponding arts. Meanwhile, in order to better understand the present disclosure, definitions and explanations of relevant terms are provided below.

CD20 (also referred to as a B-lymphocyte antigen CD20, B-lymphocyte surface antigen B1, Leu-16, Bp35, BM5 or LF5; a human protein characterized in UniProt database entry P11836) is a hydrophobic transmembrane protein that is expressed on precursor B and mature B-lymphocytes and has a molecular weight of about 35 kD (Valentine, M. A. et al., J. Biol. Chem. 264 (1989) 11282-11287; Tedder, T. F .et al., Proc. Natl .Acad. Sci. U.S.A. 85 (1988) 208-212; Stamenkovic, I. et al., J. Exp. Med. 167 (1988) 1975-1980; Einfeld, D. A. et al., EMBO J. 7 (1988) 711-717; Tedder, T. F. et al., J. Immunol. 142 (1989) 2560-2568). The corresponding human gene is membrane-spanning 4-domains, subfamily A, member 1, also referred to as MS4A1. The gene encodes a member of the membrane-spanning 4A gene family Members of the nascent protein family are characterized by common structural features and similar intron/exon splice boundaries and demonstrate unique expression patterns among hematopoietic cells and non-lymphoid tissues. The gene encodes a B-lymphocyte surface molecule that plays a role in the development and differentiation of B cells into plasma cells. The family member is localized to 11q12, among a cluster of family members. Alternative splicing of the gene results in two transcript variants that encode the same protein.

As used herein, the term "CD20" refers to any natural CD20 from any vertebrate including mammals such as primates (e.g., humans) and rodents (e.g., mice and rats), unless otherwise specified. The term encompasses "full length", unprocessed CD20 as well as any form of processed CD20 derived from a cell. The term also encompasses naturally occurring variants of CD20, such as splice variants and allelic variants. In an embodiment, CD20 is human CD20. An exemplary amino acid sequence of human CD20 is shown as SEQ ID NO: 1.

The terms "anti-CD20 antibody" and "CD20-binding antibody" refer to an antibody that can bind to CD20 with sufficient affinity such that the antibody is useful in targeting CD20 as a diagnostic and/or therapeutic agent. In an embodiment, the binding ability of the anti-CD20 antibody to unrelated non-CD20 protein is less than about 10% of the binding ability of the antibody to CD20 that is determined by, for example, radioimmunoassay (RIA). In certain embodiments, the CD20 binding antibody has a dissociation constant ($K_d$)≤1 μM, ≤100 nM, ≤10 nM, ≤1 nM, ≤0.1 nM, ≤0.01 nM or ≤0.001 nM (e.g., $10^{-8}$ M or less such as $10^{-8}$-$10^{-13}$ M, and $10^{-9}$-$10^{-13}$ M). In certain embodiments, the anti-CD20 antibody binds to conservative CD20 epitopes among CD20 from different species.

"CD3" refers to any natural CD3 from any vertebrate including mammals such as primates (e.g., humans), non-human primates (e.g., *Macaca fascicularis*) and rodents (e.g., mice and rats), unless otherwise specified. The term encompasses "full-length", unprocessed CD3 and any form of processed CD3 from a cell. The term also encompasses naturally occurring variants of CD3, such as splice variants and allelic variants. In an embodiment, CD3 is human CD3, especially the epsilon subunit of human CD3 (CD3ε). An amino acid sequence of human CD3ε is shown in UniProt (www.uniprot.org) accession number P07766 (version 144) or NCBI (www.ncbi.nlm.nih.gov/) RefSeq NP_000724.1. An amino acid sequence of cynomolgus monkey CD3ε is shown in NCBI GenBank no. BAB71849.1.

The term "cell surface" is used according to its normal meaning in the art and thus includes the outside of a cell which is accessible through binding to proteins and other molecules.

As used herein, unless otherwise specified, the term "about" or "approximate" means within plus or minus 10% of a given value or range. In a case that integers are required, the term means rounding up or down to the nearest integer within plus or minus 10% of a given value or range. With respect to antibody chain polypeptide sequences, the phrase substantially identical is to be understood as at least 60%, 65%, 70%, 75%, 80%, 85%, 90%, 95%, 96%, 97%, 98%, 99% or higher sequence identity of an antibody chain to a reference polypeptide sequence. With respect to nucleic acid sequences, the term is to be understood as at least greater than 60%, 65%, 70%, 75%, 80%, 85%, 90%, 95%, 96%, 97%, 98%, 99% or higher sequence identity of a nucleotide sequence to a reference nucleic acid sequence.

The sequence "identity" has a meaning recognized in the art, and the percentage of sequence identity between two nucleic acids or polypeptide molecules or regions can be calculated by disclosed technologies. The sequence identity can be measured along the full length of polynucleotides or polypeptides or along regions of the molecules. There are many methods for measuring the identity between two polynucleotides or polypeptides, but the term identity is well known to the skilled person (Carrillo, H. & Lipman, D., SIAM J Applied Math 48: 1073 (1988)).

A "substitution" variant refers to a variant obtained by removing at least one amino acid residue from a natural sequence and inserting a different amino acid at the same site. The substitution may be a single substitution, that is, only one amino acid in the molecule is substituted; or the substitution may be multiple substitutions, that is, two or more amino acids in the same molecule are substituted. The multiple substitutions may be at consecutive sites. Similarly, an amino acid can be substituted with multiple residues, and thus such a variant includes substitution and insertion. An insertion variant is a variant obtained by inserting one or more amino acids immediately adjacent to an amino acid at a specific site on a natural sequence. Immediately adjacent to an amino acid means linking with the α-carboxyl or α-amino functional group of the amino acid. A "deletion" variant refers to a variant obtained by removing one or more amino acids from a natural amino acid sequence. Usually, a deletion variant has one or two amino acid deletions in a specific region of its molecule.

With respect to variable domains of antibodies, the term "variable" refers to certain portions of relevant molecules that have extensive sequence differences between antibodies, and are used for the specific recognition and binding to a specific antibody against its specific target. However, the variability is not uniformly distributed throughout the variable domains of antibodies. The variability is concentrated in three segments known as complementarity-determining regions (CDRs; i.e., CDR1, CDR2, and CDR3) or hypervariable regions, which are located within variable domains of light chains and heavy chains A more conservative portion within the variable domain is referred to as a framework region (FR) or framework sequence. Each variable domain of a natural heavy chain or light chain includes four FRs, which mainly adopt a β-folded configuration and linked together through three CDRs, the CDRs form a loop, and the loop is linked with the β-folded configuration and forms a part of the β-folded configuration in certain cases. CDRs of each chain are usually linked adjacently by an FR region and contribute to the formation of a target binding site (epitope or determinant) of an antibody by virtue of CDRs from other chains As used herein, the numbering of amino acid residues of immunoglobulin is based on the numbering system of amino acid residues of immunoglobulin developed by Kabat et al., unless otherwise specified. A CDR may have the ability to specifically bind to a cognate epitope.

As used herein, an "antibody fragment" or "antigen-binding fragment" of an antibody refers to any portion of a full-length antibody, which is shorter than the full-length antibody, at least contains a partial variable region (e.g., one or more CDRs and/or one or more antibody-binding sites) of the antibody that binds to an antigen, and thus retains the binding specificity and at least partial specific binding ability of the full-length antibody. Therefore, the antigen-binding fragment refers to an antibody fragment that contains an antigen-binding portion binding to the same antigen as the antibody from which the antibody fragment is derived. The antibody fragment includes an antibody derivative that is produced by enzymatic treatment of the full-length antibody, and a synthesized derivative such as a recombinant derivative. The antibody includes the antibody fragment. Examples of the antibody fragment include, but are not limited to, Fab, Fab', F(ab')2, single-stranded Fv(scFv), Fv, dsFv, double antibody, Fd and a Fd' fragment, and other fragments, including a modified fragment. The fragment may include multiple chains that are linked together through, for example, disulfide bonds and/or peptide adaptors. The antibody fragment generally contains at least or about 50 amino acids, typically at least or about 200 amino acids. The antigen-binding fragment includes any antibody fragment, which is inserted into an antibody framework (e.g., by replacing a corresponding region) to obtain an antibody specifically binding to (that is, with a binding constant Ka of about 107-108M-1) an antigen. A "functional fragment" or "analog of an anti-CD20 antibody" is a fragment or analog that can prevent or substantially reduce the ability of the receptor to bind to a ligand or initiate signal transduction. As used herein, the functional fragment generally has the same meaning as an antibody fragment, and with respect to an antibody, it may refer to a fragment that can prevent the receptor from binding to a ligand or from initiating signal transduction or substantially reduce the ability of the receptor to bind to a ligand or initiate signal transduction. The Fv fragment consists of a dimer (VH-VL dimer) formed by non-covalent binding of a variable domain of a heavy chain and a variable region of a light chain. In this configuration, three CDRs of each variable domain interact to define a target binding site on the surface of the VH-VL dimer, as in the case of an intact antibody. The six CDRs together confer the target binding specificity to the intact antibody. However, even a single variable domain (or half of Fv containing 3 target-specific CDRs only) can still have the ability to recognize and bind to a target.

As used herein, the term "bispecific antibody (BsAb)" refers to an antibody and/or antigen-binding molecule that can specifically bind to two different antigenic determinants, and usually, the bispecific antibody and/or antigen-binding molecule contains two antigen-binding sites each of which is specific to different antigenic determinants. In certain embodiments, the bispecific antibody and/or antigen-binding molecule can bind to two antigenic determinants at the same time, particularly two antigenic determinants that are expressed on two different types of cells.

As used herein, a "monoclonal antibody" refers to a population of identical antibodies, meaning that each individual antibody molecule in the population of monoclonal antibodies is identical to the other antibody molecules. This characteristic is in contrast to that of a polyclonal population of antibodies, which contain antibodies with a variety of different sequences. Monoclonal antibodies can be prepared by many well-known methods (Smith et al. (2004) J.Clin. Pathol. 57, 912-917; and Nelson et al., J Clin Pathol (2000), 53, 111-117). For example, monoclonal antibodies can be prepared by immortalizing B cells, for example, fusing with myeloma cells to produce a hybridoma cell line or infecting B cells with virus such as EBV. Recombination can also be used to prepare antibodies in vitro from clonal populations of host cells by transforming the host cells with plasmids carrying artificial sequences of nucleotides encoding the antibodies As used herein, the term "hybridoma" or "hybridoma cell" refers to a cell or cell line (usually myeloma or lymphoma cells) produced by fusing lymphocytes that produce antibodies with cancer cells that do not produce antibodies. As is known to those of ordinary skill in the art, a hybridoma can proliferate and continuously supply and produce specific monoclonal antibodies. The method for producing a hybridoma is known in the art. When the term "hybridoma" or "hybridoma cell" is referred to, it also includes a subclone and progeny cells of the hybridoma.

As used herein, a full-length antibody is an antibody that has two full-length heavy chains (e.g., VH-CH1-CH2-CH3 and VH-CH1-CH2-CH3-CH4), two full-length light chains (VL-CL), and hinge regions, such as an antibody produced naturally by antibody-secreting B cells and a synthesized antibody with the same domains.

The term "chimeric antibody" refers to an antibody that contains a variable region sequence derived from a species and a constant region sequence derived from another species. For example, the variable region sequence is derived from a mouse antibody and the constant region sequence is derived from a human antibody.

A "humanized" antibody refers to a non-human (e.g., mouse) antibody form, which is a chimeric immunoglobulin, immunoglobulin chain or a fragment thereof (e.g., Fv, Fab, Fab', F(ab')2 or other antigen-binding subsequences of an antibody), containing the minimal sequence derived from a non-human immunoglobulin. Preferably, the humanized antibody is a human immunoglobulin (recipient antibody), and residues in a complementary determining region (CDR) of the recipient antibody are substituted with CDR residues in a non-human species, such as a mouse, a rat and a rabbit, that has the desired specificity, affinity and ability.

In addition, during humanization, amino acid residues within CDR1, CDR2 and/or CDR3 regions of VH and/or VL may be mutated, so as to improve one or more binding characteristics (e.g., the affinity). A mutation can be introduced, for example, by performing PCR-mediated mutation, the influence of which on antibody binding or other functional characteristics can be assessed using the in vitro or in vivo assay described herein. Usually, a conservative mutation is introduced. Such a mutation may be amino acid substitution, addition or deletion. In addition, there are usually no more than one or two mutations within a CDR. Therefore, the humanized antibody of the present disclosure also covers an antibody of which a CDR contains 1 or 2 amino acid mutations.

As used herein, the term "CDR" refers to a complementarity-determining region, and each heavy chain or light chain of a known antibody molecule has 3 CDRs. CDR is also referred to as a hypervariable region that exists in a variable region of each heavy chain or light chain of an antibody, and the primary structure of CDR has a site with very high variability. In this description, CDRs of a heavy chain are represented by CDR1, CDR2, and CDR3 derived from the amino-terminus of the amino-terminal sequence of the heavy chain, and CDRs of a light chain are represented by CDR1, CDR2, and CDR3 derived from the amino-terminus of the amino-terminal sequence of the light chain These sites are adjacent to each other in the tertiary structure and determine the specificity of an antigen to which an antibody binds.

As used herein, the term "epitope" refers to any antigenic determinant on an antigen to which a paratope of an antibody binds. An epitope determinant usually contains a chemically active surface type of a molecule, such as an amino acid and a sugar side chain, and usually has specific three-dimensional structural characteristics and specific charge characteristics.

As used herein, the "specific binding" or "immunospecific binding" of an antibody or an antigen-binding fragment thereof are interchangeable herein, and refers to the ability of the antibody or the antigen-binding fragment thereof to form one or more non-covalent bonds with the same antigen through non-covalent interaction of the antibody and an antibody-binding site of an antigen. The antigen may be a separated antigen or present in tumor cells. Usually, an antibody immunospecifically binding (or specifically binding) to an antigen binds to the antigen with an affinity constant Ka of about $1\times10^{7}$ $M^{-1}$ or $1\times10^{8}$ $M^{-1}$ or greater (or with a dissociation constant (Kd) of $1\times10^{-7}$ M or $1\times10^{-8}$ M or less). An affinity constant can be measured by standard kinetic methods for antibody responses, such as immunoassay, surface plasmon resonance (SPR) (Rich and Myszka (2000) Curr. Opin. Biotechnol 11: 54; and Englebienne (1998) Analyst. 123: 1599), isothermal titration calorimetry (ITC), and other dynamic interaction known in the art (also referring to U.S. Pat. No. 7,229,619 describing exemplary SPR and ITC methods for calculating the binding affinity of antibodies). Instruments and methods for real-time detection and monitoring of binding rates are known and commercially available (referring to BiaCore 2000, Biacore AB, Upsala, Sweden and GE Healthcare Life Sciences; Malmqvist (2000) Biochem. Soc. Trans. 27: 335).

As used herein, the terms "polynucleotide" and "nucleic acid molecule" refer to an oligomer or polymer that contains at least two linked nucleotides or nucleotide derivatives, including deoxyribonucleic acid (DNA) and ribonucleic acid (RNA) that are usually linked together through phosphodiester bonds. As used herein, the term "nucleic acid molecule" is intended to include DNA molecules and RNA molecules. A DNA molecule may be single-stranded or double-stranded, and may be cDNA.

As used herein, a separated nucleic acid molecule is a nucleic acid molecule that is separated from other nucleic acid molecules present in a natural source of the nucleic acid molecule. A "separated" nucleic acid molecule, such as a cDNA molecule, may be substantially free of other cellular materials or culture medium when prepared by recombination, or substantially free of chemical precursors or other chemical components when chemically synthesized. Exemplary separated nucleic acid molecules provided herein include a separated nucleic acid molecule encoding the antibody or antigen-binding fragment provided.

As used herein, "operably linking" of nucleic acid sequences, regions, elements or domains means that the nucleic acid regions are functionally related to each other. For example, a promoter can be operably linked to a nucleic acid encoding a polypeptide such that the promoter regulates or mediates transcription of the nucleic acid.

"Conservative sequence modifications" of the sequences in the sequence listings herein are also provided, i.e., nucleotide and amino acid sequence modifications that do not eliminate the binding of an antibody encoded by the nucleotide sequence or containing the amino acid sequence to an antigen. These conservative sequence modifications include conservative nucleotide and amino acid substitutions, nucleotide and amino acid additions, and deletions. For example, a modification can be introduced into the sequence listings herein by the standard technology (e.g., site-directed mutagenesis and PCR-mediated mutagenesis) known in the art. The conservative sequence modifications include amino acid substitutions in which amino acid residues are substituted with amino acid residues with similar side chains Families of amino acid residues with similar side chains are defined in the art. The families include amino acids with basic side chains (e.g., lysine, arginine, and histidine), amino acids with acidic side chains (e.g., aspartic acid and glutamic acid), amino acids with uncharged polar side chains (e.g., glycine, asparagine, glutamine, serine, threonine, tyrosine, cysteine, and tryptophan), amino acids with non-polar side chains (e.g., alanine, valine, leucine, isoleucine, proline, phenylalanine, and methionine), amino acids with β branched side chains (e.g., threonine, valine, and isoleucine), and amino acids with aromatic side chains (e.g., tyrosine, phenylalanine, tryptophan, and histidine). Therefore, a predicted nonessential amino acid residue in an anti-CD20 antibody is preferably substituted with another amino acid residue from the same side chain family Methods for identifying nucleotide and amino acid conservative substitutions that do not eliminate binding to an antigen are well known in the art (for example, referring to Brummell et al., Biochem. 32: (1180-1187 (1993); Kobayashi et al., Protein Eng. 12(10): 879-884 (1999); Burks et al., Proc. Natl. Acad. Sci. USA 94: 412-417 (1997)).

As another option, in another embodiment, mutations can be introduced randomly along all or a portion of the anti-CD20 antibody coding sequence by, for example, saturation mutagenesis, and the obtained modified anti-CD20 antibodies can be screened for improved binding activity.

As used herein, "expression" refers to the process of producing a polypeptide by the transcription and translation of a polynucleotide. An expression level of a polypeptide can be assessed by any method known in the art, including, for example, methods for determining the amount of polypeptides produced by a host cell. Such methods may include, but are not limited to, quantification of polypeptides in a cell lysate by ELISA, Coomassie blue staining after gel electrophoresis, Lowry protein assay, and Bradford protein assay.

As used herein, a "host cell" is a cell for receiving, maintaining, replicating and amplifying a vector. The host cell can also be used for expressing polypeptides encoded by the vector. When the host cell divides, a nucleic acid contained in the vector is replicated such that the nucleic acid is amplified. The host cell may be a eukaryotic cell or prokaryotic cell. Suitable host cells include, but are not limited to, CHO cells, various COS cells, HeLa cells, and HEK cells such as HEK 293 cells.

As used herein, the "vector" is a replicable nucleic acid from which one or more heterologous proteins can be expressed when the vector is transformed into an appropriate host cell. The vector includes those vectors into which nucleic acids encoding polypeptides or fragments thereof can be introduced, usually by restriction digestion and ligation. The vector also includes those vectors that contain nucleic acids encoding polypeptides. The vector is used to introduce a nucleic acid encoding a polypeptide into the host cell, so as to amplify the nucleic acid or express/display the polypeptide encoded by the nucleic acid. The vector is usually free, but can be designed to allow integration of a gene or a portion thereof into a chromosome of a genome. Vectors for artificial chromosome are also contemplated, such as a yeast artificial vector and a mammal artificial chromosome. Selection and use of such intermedia are well-known to those skilled in the art.

As used herein, the vector also includes a "virus vector" or "viral vector". The viral vector is an engineered virus that is operably linked to an exogenous gene to transfer (as an intermedium or shuttle) the exogenous gene into cells.

As used herein, an "expression vector" includes vectors that can express DNA, and the DNA is operably linked to a regulatory sequence that can affect the expression of such DNA fragments, such as a promoter. Such additional fragments may include promoter and terminator sequences, and optionally may include one or more origins of replication, one or more selectable markers, enhancers, polyadenylation signals, etc. The expression vector is usually derived from a plasmid or virus DNA, or may contain elements of both. Therefore, the expression vector refers to a recombinant DNA or RNA construct, such as a plasmid, a phage, a recombinant virus, and other vectors, which expresses cloned DNA when introduced into an appropriate host cell, Appropriate expression vectors are well-known to those skilled in the art, and include expression vectors that can be replicated in eukaryotic cells and/or prokaryotic cells, free expression vectors, and expression vectors for integration into the genome of a host cell.

As used herein, "treatment" of a disease or disease condition in an individual means that individual's symptoms are partially or fully alleviated, or remain unchanged after treatment. Therefore, treatment includes prophylaxis, treatment and/or cure. Prophylaxis refers to prevention of an underlying disease and/or prevention of symptomatic deterioration or disease development. Treatment also includes any pharmaceutical use of any provided antibody or antigen-binding fragment thereof and composition provided herein.

As used herein, a "therapeutic effect" means an effect resulting from treatment of an individual that alters, usually improves or ameliorates symptoms of a disease or disease condition, or cures a disease or disease condition.

As used herein, the "therapeutically effective amount" or "therapeutically effective dose" refers to the amount of a substance, compound, material or composition containing a compound that is at least sufficient to produce a therapeutic effect when administered to a subject. Therefore, it is the amount necessary to prevent, cure, ameliorate, arrest or partially arrest symptoms of a disease or disorder.

As used herein, the "prophylactically effective amount" or "prophylactically effective dose" refers to the amount of a substance, compound, material, or composition containing a compound that, when administered to a subject, will have the desired prophylactic effect, such as preventing or delaying the onset or recurrence of a disease or symptom, and reducing the likelihood of the onset or recurrence of a disease or symptom. A full prophylactically effective dose does not have to occur by administering one dose, and may only occur after administering a series of doses. Therefore, the prophylactically effective amount may be administered in one or more administrations.

As used herein, the term "patient" refers to a mammal, such as humans.

II. Detailed Description of Specific Embodiments

In an aspect, the present disclosure provides a bispecific antibody or an antigen-binding portion thereof, which contains a first binding domain that binds to CD20 on the surface of a target cell and a second binding domain that binds to CD3 on the surface of a T cell. The first binding domain contains a first light chain and a first heavy chain, the first light chain contains a light chain CDR selected from amino acid sequences SEQ ID NO: 56, 57, 58, 61, 62, 63, or any variant thereof, and/or the first heavy chain contains a heavy chain CDR selected from amino acid sequences SEQ ID NO: 66, 67, 68, 71, 76, 77, 78, 85, or any variant thereof.

According to the antibody or the antigen-binding portion thereof of the aforementioned aspect, the first light chain of the first binding domain contains a light chain CDR1 selected from amino acid sequences SEQ ID NO: 56, 61, or any variant thereof, a light chain CDR2 selected from amino acid sequences SEQ ID NO: 57, 62, or any variant thereof, a light chain CDR3 selected from amino acid sequences SEQ ID NO: 58, 63, or any variant thereof; and/or the first heavy chain of the first binding domain contains a heavy chain CDR1 selected from amino acid sequences SEQ ID NO: 66, 76, or any variant thereof, a heavy chain CDR2 selected from amino acid sequences SEQ ID NO: 67, 77, or any variant thereof, a heavy chain CDR3 selected from amino acid sequences SEQ ID NO: 68, 71, 78, 85, or any variant thereof.

According to the antibody or the antigen-binding portion thereof of the aforementioned aspect, the first binding domain contains a light chain and heavy chain CDR combination selected from:

(1) first light chain CDR1, CDR2 and CDR3 sequences respectively containing SEQ ID NO: 56-58, and/or first heavy chain CDR1, CDR2 and CDR3 sequences respectively containing SEQ ID NO: 66-68;

(2) first light chain CDR1, CDR2 and CDR3 sequences respectively containing SEQ ID NO: 56-58, and/or first heavy chain CDR1, CDR2 and CDR3 respectively containing SEQ ID NO: 66, 67 and 71;

(3) first light chain CDR1, CDR2 and CDR3 sequences respectively containing SEQ ID NO: 61-63, and/or first heavy chain CDR1, CDR2 and CDR3 sequences respectively containing SEQ ID NO: 76-78; and (4) first light chain CDR1, CDR2 and CDR3 sequences respectively containing SEQ ID NO: 61-63, and/or first heavy chain CDR1, CDR2 and CDR3 respectively containing SEQ ID NO: 76, 77 and 85.

According to the antibody or the antigen-binding portion thereof of the aforementioned aspect, the first binding domain contains a light chain variable region selected from amino acid sequences SEQ ID NO: 54, 59 , or any variant thereof, and/or a heavy chain variable region selected from amino acid sequences SEQ ID NO: 64, 69, 72, 74, 79, 81, 83, or any variant thereof.

In some embodiments, the first binding domain contains a first light chain variable region of amino acid sequence SEQ ID NO: 54 or any variant thereof, and a first heavy chain variable region of amino acid sequence SEQ ID NO: 64 or any variant thereof.

In some embodiments, the first binding domain contains a first light chain variable region of amino acid sequence SEQ ID NO: 54 or any variant thereof, and a first heavy chain variable region of amino acid sequence SEQ ID NO: 69 or any variant thereof.

In some embodiments, the first binding domain contains a first light chain variable region of amino acid sequence SEQ ID NO: 54 or any variant thereof, and a first heavy chain variable region of amino acid sequence SEQ ID NO: 72 or any variant thereof.

In some embodiments, the first binding domain contains a first light chain variable region of amino acid sequence SEQ ID NO: 59 or any variant thereof, and a first heavy chain variable region of amino acid sequence SEQ ID NO: 74 or any variant thereof.

In some embodiments, the first binding domain contains a first light chain variable region of amino acid sequence SEQ ID NO: 59 or any variant thereof, and a first heavy chain variable region of amino acid sequence SEQ ID NO: 79 or any variant thereof.

In some embodiments, the first binding domain contains a first light chain variable region of amino acid sequence SEQ ID NO: 59 or any variant thereof, and a first heavy chain variable region of amino acid sequence SEQ ID NO: 81 or any variant thereof.

In some embodiments, the first binding domain contains a first light chain variable region of amino acid sequence SEQ ID NO: 59 or any variant thereof, and a first heavy chain variable region of amino acid sequence SEQ ID NO: 83 or any variant thereof.

According to the antibody or the antigen-binding portion thereof of the aforementioned aspect, the second binding domain contains a second light chain CDR1 selected from amino acid sequences SEQ ID NO: 7, 14, or any variant thereof, a second light chain CDR2 selected from amino acid sequences SEQ ID NO: 8, 15, 20, or any variant thereof, and a second light chain CDR3 selected from amino acid sequences SEQ ID NO: 9, 21, or any variant thereof; and/or a second heavy chain CDR1 selected from amino acid sequences SEQ ID NO: 26, 31, 46, or any variant thereof, a second heavy chain CDR2 selected from amino acid sequences SEQ ID NO: 27, 47, or any variant thereof, a second heavy chain CDR3 selected from amino acid sequences 28, 34, 37, 40, 43, or any variant thereof.

In some embodiments, the second binding domain contains a second light chain and a second heavy chain, and the second binding domain contains a light chain and heavy chain CDR combination selected from:

(1) second light chain CDR1, CDR2 and CDR3 sequences respectively containing SEQ ID NO: 7, 8 and 9, and second heavy chain CDR1, CDR2 and CDR3 sequences respectively containing SEQ ID NO: 26, 27 and 28;

(2) second light chain CDR1, CDR2 and CDR3 sequences respectively containing SEQ ID NO: 7, 8 and 9, and second heavy chain CDR1, CDR2 and CDR3 sequences respectively containing SEQ ID NO: 31, 27 and 28;

(3) second light chain CDR1, CDR2 and CDR3 sequences respectively containing SEQ ID NO: 7, 8 and 9, and second heavy chain CDR1, CDR2 and CDR3 sequences respectively containing SEQ ID NO: 31, 27 and 34;

(4) second light chain CDR1, CDR2 and CDR3 sequences respectively containing SEQ ID NO: 7, 8 and 9, and second heavy chain CDR1, CDR2 and CDR3 sequences respectively containing SEQ ID NO: 31, 27 and 37;

(5) second light chain CDR1, CDR2 and CDR3 sequences respectively containing SEQ ID NO: 7, 8 and 9, and second heavy chain CDR1, CDR2 and CDR3 sequences respectively containing SEQ ID NO: 31, 27 and 40;

(6) second light chain CDR1, CDR2 and CDR3 sequences respectively containing SEQ ID NO: 7, 8 and 9, and second heavy chain CDR1, CDR2 and CDR3 sequences respectively containing SEQ ID NO: 31, 27 and 43;

(7) second light chain CDR1, CDR2 and CDR3 sequences respectively containing SEQ ID NO: 7, 8 and 9, and second heavy chain CDR1, CDR2 and CDR3 sequences respectively containing SEQ ID NO: 46, 47 and 28;

(8) second light chain CDR1, CDR2 and CDR3 sequences respectively containing SEQ ID NO: 14, 15 and 9, and second heavy chain CDR1, CDR2 and CDR3 sequences respectively containing SEQ ID NO: 26, 27 and 28;

(9) second light chain CDR1, CDR2 and CDR3 sequences respectively containing SEQ ID NO: 14, 15 and 9, and second heavy chain CDR1, CDR2 and CDR3 sequences respectively containing SEQ ID NO: 31, 27 and 28;

(10) second light chain CDR1, CDR2 and CDR3 sequences respectively containing SEQ ID NO: 14, 15 and 9, and second heavy chain CDR1, CDR2 and CDR3 sequences respectively containing SEQ ID NO: 31, 27 and 34;

(11) second light chain CDR1, CDR2 and CDR3 sequences respectively containing SEQ ID NO: 14, 15 and 9, and second heavy chain CDR1, CDR2 and CDR3 sequences respectively containing SEQ ID NO: 31, 27 and 37;

(12) second light chain CDR1, CDR2 and CDR3 sequences respectively containing SEQ ID NO: 14, 15 and 9, and second heavy chain CDR1, CDR2 and CDR3 sequences respectively containing SEQ ID NO: 31, 27 and 40;

(13) second light chain CDR1, CDR2 and CDR3 sequences respectively containing SEQ ID NO: 14, 15 and 9, and second heavy chain CDR1, CDR2 and CDR3 sequences respectively containing SEQ ID NO: 31, 27 and 43;

(14) second light chain CDR1, CDR2 and CDR3 sequences respectively containing SEQ ID NO: 14, 15 and 9, and second heavy chain CDR1, CDR2 and CDR3 sequences respectively containing SEQ ID NO: 46, 47 and 28;

(15) second light chain CDR1, CDR2 and CDR3 sequences respectively containing SEQ ID NO: 7, 8 and 21, and second heavy chain CDR1, CDR2 and CDR3 sequences respectively containing SEQ ID NO: 26, 27 and 28;

(16) second light chain CDR1, CDR2 and CDR3 sequences respectively containing SEQ ID NO: 7, 8 and 21, and second heavy chain CDR1, CDR2 and CDR3 sequences respectively containing SEQ ID NO: 31, 27 and 28;

(17) second light chain CDR1, CDR2 and CDR3 sequences respectively containing SEQ ID NO: 7, 8 and 21, and second heavy chain CDR1, CDR2 and CDR3 sequences respectively containing SEQ ID NO: 31, 27 and 34;

(18) second light chain CDR1, CDR2 and CDR3 sequences respectively containing SEQ ID NO: 7, 8 and 21, and second heavy chain CDR1, CDR2 and CDR3 sequences respectively containing SEQ ID NO: 31, 27 and 37;

(19) second light chain CDR1, CDR2 and CDR3 sequences respectively containing SEQ ID NO: 7, 8 and 21, and second heavy chain CDR1, CDR2 and CDR3 sequences respectively containing SEQ ID NO: 31, 27 and 40;

(20) second light chain CDR1, CDR2 and CDR3 sequences respectively containing SEQ ID NO: 7, 8 and 21, and second heavy chain CDR1, CDR2 and CDR3 sequences respectively containing SEQ ID NO: 31, 27 and 43;

(21) second light chain CDR1, CDR2 and CDR3 sequences respectively containing SEQ ID NO: 7, 8 and 21, and second heavy chain CDR1, CDR2 and CDR3 sequences respectively containing SEQ ID NO: 46, 47 and 28;

(22) second light chain CDR1, CDR2 and CDR3 sequences respectively containing SEQ ID NO: 7, 20 and 21, and second heavy chain CDR1, CDR2 and CDR3 sequences respectively containing SEQ ID NO: 26, 27 and 28;

(23) second light chain CDR1, CDR2 and CDR3 sequences respectively containing SEQ ID NO: 7, 20 and 21, and second heavy chain CDR1, CDR2 and CDR3 sequences respectively containing SEQ ID NO: 31, 27 and 28;

(24) second light chain CDR1, CDR2 and CDR3 sequences respectively containing SEQ ID NO: 7, 20 and 21, and second heavy chain CDR1, CDR2 and CDR3 sequences respectively containing SEQ ID NO: 31, 27 and 34;

(25) second light chain CDR1, CDR2 and CDR3 sequences respectively containing SEQ ID NO: 7, 20 and 21, and second heavy chain CDR1, CDR2 and CDR3 sequences respectively containing SEQ ID NO: 31, 27 and 37;

(26) second light chain CDR1, CDR2 and CDR3 sequences respectively containing SEQ ID NO: 7, 20 and 21, and second heavy chain CDR1, CDR2 and CDR3 sequences respectively containing SEQ ID NO: 31, 27 and 40;

(27) second light chain CDR1, CDR2 and CDR3 sequences respectively containing SEQ ID NO: 7, 20 and 21, and second heavy chain CDR1, CDR2 and CDR3 sequences respectively containing SEQ ID NO: 31, 27 and 43;

(28) second light chain CDR1, CDR2 and CDR3 sequences respectively containing SEQ ID NO: 7, 20 and 21, and second heavy chain CDR1, CDR2 and CDR3 sequences respectively containing SEQ ID NO: 46, 47 and 28.

In some embodiments, the second binding domain contains a light chain variable region selected from amino acid sequences SEQ ID NO: 5, 10, 12, 16, 18, 22, or any variant thereof, and/or a heavy chain variable region selected from amino acid sequences SEQ ID NO: 24, 29, 32, 35, 38, 41, 44, 48, 50, 52, or any variant thereof.

In some embodiments, the second binding domain contains a second light chain variable region of amino acid sequence SEQ ID NO: 5 or any variant thereof, and a second heavy chain variable region of amino acid sequence SEQ ID NO: 48 or any variant thereof.

In some embodiments, the second binding domain contains a second light chain variable region of amino acid sequence SEQ ID NO: 5 or any variant thereof, and a second heavy chain variable region of amino acid sequence SEQ ID NO: 50 or any variant thereof.

In some embodiments, the second binding domain contains a second light chain variable region of amino acid sequence SEQ ID NO: 10 and any variant thereof, and a second heavy chain variable region of amino acid sequence SEQ ID NO: 50 and any variant thereof.

In some embodiments, the second binding domain contains a second light chain variable region of amino acid sequence SEQ ID NO: 12 and any variant thereof, and a second heavy chain variable region of amino acid sequence SEQ ID NO: 50 and any variant thereof.

In some embodiments, the second binding domain contains a second light chain variable region of amino acid sequence SEQ ID NO: 18 and any variant thereof, and a second heavy chain variable region of amino acid sequence SEQ ID NO: 24 and any variant thereof.

In some embodiments, the second binding domain contains a second light chain variable region of amino acid sequence SEQ ID NO: 18 and any variant thereof, and a second heavy chain variable region of amino acid sequence SEQ ID NO: 48 and any variant thereof.

In some embodiments, the second binding domain contains a second light chain variable region of amino acid sequence SEQ ID NO: 18 and any variant thereof, and a second heavy chain variable region of amino acid sequence SEQ ID NO: 50 and any variant thereof.

According to the antibody or the antigen-binding portion thereof of the aforementioned aspect, the first light chain contains a light chain selected from SEQ ID NO: 88, 96, 100, 102, 110, 118, or any variant thereof, the first heavy chain contains a heavy chain selected from SEQ ID NO: 86, 94, 98, 104, 112, 120, or any variant thereof.

According to the antibody or the antigen-binding portion thereof of the aforementioned aspect, the second light chain contains a light chain selected from SEQ ID NO: 92, 106, 114, or any variant thereof, the second heavy chain contains a heavy chain selected from SEQ ID NO: 90, 108, 116, or any variant thereof.

In some embodiments, the first binding domain contains a first light chain of amino acid sequence SEQ ID NO: 88 or any variant thereof, and a first heavy chain of amino acid sequence SEQ ID NO: 86 or any variant thereof.

In some embodiments, the first binding domain contains a first light chain of amino acid sequence SEQ ID NO: 96 or any variant thereof, and a first heavy chain of amino acid sequence SEQ ID NO: 94 or any variant thereof.

In some embodiments, the first binding domain contains a first light chain of amino acid sequence SEQ ID NO: 100 or any variant thereof, and a first heavy chain of amino acid sequence SEQ ID NO: 98 or any variant thereof.

In some embodiments, the first binding domain contains a first light chain of amino acid sequence SEQ ID NO: 102 or any variant thereof, and a first heavy chain of amino acid sequence SEQ ID NO: 104 or any variant thereof.

In some embodiments, the first binding domain contains a first light chain of amino acid sequence SEQ ID NO: 110 or any variant thereof, and a first heavy chain of amino acid sequence SEQ ID NO: 112 or any variant thereof.

In some embodiments, the first binding domain contains a first light chain of amino acid sequence SEQ ID NO: 118 or any variant thereof, and a first heavy chain of amino acid sequence SEQ ID NO: 120 or any variant thereof.

In some embodiments, the second binding domain contains a second light chain of amino acid sequence SEQ ID NO: 92 or any variant thereof, and a second heavy chain of amino acid sequence SEQ ID NO: 90 or any variant thereof.

In some embodiments, the second binding domain contains a second light chain of amino acid sequence SEQ ID NO: 106 or any variant thereof, and a second heavy chain of amino acid sequence SEQ ID NO: 108 or any variant thereof.

In some embodiments, the second binding domain contains a second light chain of amino acid sequence SEQ ID NO: 114 or any variant thereof, and a second heavy chain of amino acid sequence SEQ ID NO: 116 or any variant thereof.

In some embodiments, the bispecific antibody contains a first light chain of amino acid sequence SEQ ID NO: 88 or any variant thereof, a first heavy chain of amino acid sequence SEQ ID NO: 86 or any variant thereof, a second light chain of amino acid sequence SEQ ID NO: 92 or any variant thereof, and a second heavy chain of amino acid sequence SEQ ID NO: 90 or any variant thereof.

In some embodiments, the bispecific antibody contains a first light chain of amino acid sequence SEQ ID NO: 96 or any variant thereof, a first heavy chain of amino acid sequence SEQ ID NO: 94 or any variant thereof, a second light chain of amino acid sequence SEQ ID NO: 92 or any variant thereof, and a second heavy chain of amino acid sequence SEQ ID NO: 90 or any variant thereof.

In some embodiments, the bispecific antibody contains a first light chain of amino acid sequence SEQ ID NO: 100 or any variant thereof, a first heavy chain of amino acid sequence SEQ ID NO: 98 or any variant thereof, a second light chain of amino acid sequence SEQ ID NO: 92 or any variant thereof, and a second heavy chain of amino acid sequence SEQ ID NO: 90 or any variant thereof.

In some embodiments, the bispecific antibody contains a first light chain of amino acid sequence SEQ ID NO: 102 or any variant thereof, a first heavy chain of amino acid sequence SEQ ID NO: 104 or any variant thereof, a second light chain of amino acid sequence SEQ ID NO: 106 or any variant thereof, a second heavy chain of amino acid sequence SEQ ID NO: 108 or any variant thereof.

In some embodiments, the bispecific antibody contains a first light chain of amino acid sequence SEQ ID NO: 110 or any variant thereof, a first heavy chain of amino acid sequence SEQ ID NO: 112 or any variant thereof, a second light chain of amino acid sequence SEQ ID NO: 114 or any variant thereof, and a second heavy chain of amino acid sequence SEQ ID NO: 116 or any variant thereof.

In some embodiments, the bispecific antibody contains a first light chain of amino acid sequence SEQ ID NO: 118 or any variant thereof, a first heavy chain of amino acid sequence SEQ ID NO: 120 or any variant thereof, a second light chain of amino acid sequence SEQ ID NO: 114 or any variant thereof, and a second heavy chain of amino acid sequence SEQ ID NO: 116 or any variant thereof.

In some embodiments, the bispecific antibody contains a first light chain of amino acid sequence SEQ ID NO: 110 or any variant thereof, a first heavy chain of amino acid sequence SEQ ID NO: 112 or any variant thereof, a second light chain of amino acid sequence SEQ ID NO: 106 or any variant thereof, a second heavy chain of amino acid sequence SEQ ID NO: 108 or any variant thereof.

In some embodiments, the bispecific antibody contains a first light chain of amino acid sequence SEQ ID NO: 102 or any variant thereof, a first heavy chain of amino acid sequence SEQ ID NO: 104 or any variant thereof, a second light chain of amino acid sequence SEQ ID NO: 114 or any variant thereof, and a second heavy chain of amino acid sequence SEQ ID NO: 116 or any variant thereof.

A CD20-binding antibody or an antigen-binding portion thereof that has at least greater than 60%, 65%, 70%, 75%, 80%, 85%, 90%, 95%, 96%, 97%, 98%, 99% or higher sequence identity with the antibody or the antigen-binding portion thereof of any one of the aforementioned aspects is provided.

A nucleic acid encoding the antibody or the antigen-binding portion thereof of any one of the aforementioned aspects, or a nucleic acid molecule having at least greater than 60%, 65%, 70%, 75%, 80%, 85%, 90%, 95%, 96%, 97%, 98%, 99% or higher sequence identity with the antibody or the antigen-binding portion thereof of any one of the aforementioned aspects is provided.

In some embodiments, a nucleic acid encoding the first light variable region is a nucleic acid sequence selected from SEQ ID NO: 55, 60, or any variant thereof.

In some embodiments, a nucleic acid encoding the first heavy chain variable region is a nucleic acid sequence selected from SEQ ID NO: 65, 70, 73, 75, 80, 82, 84, or any variant thereof.

In some embodiments, a nucleic acid encoding the second light chain variable region is a nucleic acid sequence selected from SEQ ID NO: 6, 11, 13, 17, 19, 23, or any variant thereof.

In some embodiments, a nucleic acid encoding the second heavy chain variable region is a nucleic acid sequence selected from SEQ ID NO: 25, 30, 33, 36, 39, 42, 45, 49, 51, 53, or any variant thereof.

In some embodiments, a nucleic acid encoding the first light chain is a nucleic acid sequence selected from SEQ ID NO: 89, 97, 101, 103, 111, 119, or any variant thereof.

In some embodiments, a nucleic acid encoding the first heavy chain is a nucleic acid sequence selected from SEQ ID NO: 87, 95, 99, 105, 113, 121, or any variant thereof.

In some embodiments, a nucleic acid encoding the second light chain is a nucleic acid sequence selected from SEQ ID NO: 93, 107, 115, or any variant thereof.

In some embodiments, a nucleic acid encoding the second heavy chain is a nucleic acid sequence selected from SEQ ID NO: 91, 109, 117, or any variant thereof.

A vector containing the above nucleic acid is provided.

A cell containing the above nucleic acid or vector is provided.

A composition containing the above bispecific antibody or antigen-binding portion thereof, nucleic acid, vector and/or cell is provided.

An antibody-drug conjugate containing the above bispecific antibody or antigen-binding portion thereof that is covalently attached to a therapeutic moiety is provided.

Preferably, the therapeutic moiety is selected from a cytotoxic moiety, a chemotherapeutic agent, a cytokine, an immunosuppressant, an immunostimulator, a lytic peptide, and a radioisotope.

The antibody of the present disclosure is used as a therapeutic or diagnostic tool for various diseases in which CD20 is unfavorably expressed or found.

In an embodiment of a CD20-associated disease, the expression of CD20 is increased in cells of a diseased tissue or organ compared to the state in a healthy tissue or organ. Increase refers to an increase of at least 10%, especially at least 20%, at least 50%, at least 100%, at least 200%, at least 500%, at least 1000%, at least 10000% or even more. In an embodiment, expression is found in a diseased tissue only, and the expression in a corresponding health tissue is depressed. According to the present disclosure, CD20-associated diseases include B-cell diseases, such as B-cell proliferative disorders, especially CD20-positive B-cell disorders.

"B-cell proliferative disorder" means a disease in which the number of B cells in a patient is increased compared to the number of B cells in a healthy subject, especially in which the increased number of B cells is a cause or marker of the disease. "CD20-positive B-cell proliferative disorder" is a B-cell proliferative disorder in which B cells, especially malignant B cells (except for normal B cells), express CD20.

Exemplary B-cell proliferative disorders include non-Hodgkin lymphoma (NHL), acute lymphoblastic leukemia (ALL), chronic lymphocytic leukemia (CLL), diffuse large B-cell lymphoma (DLBCL), follicular lymphoma (FL), mantle cell lymphoma (MCL), marginal zone lymphoma (MZL), and some types of multiple myeloma (MM) and Hodgkin lymphoma (HL).

The method of the present disclosure is applicable to a variety of diseases, depending on a therapeutic agent used. However, this method is particularly useful in the treatment of B-cell proliferative disorders, particularly CD20-positive B-cell disorders, in which (CD20-positive) B cells are present in large numbers (i.e., the increased numbers of B cells are present in a subject with the disorder compared to a healthy subject). Thus, in an embodiment, the disease is a B-cell proliferative disorder, particularly a CD20-positive B-cell disorder.

In some embodiments, the therapeutic agent contains an antibody indicated for the treatment of cancer. In an embodiment, the therapeutic agent is indicated for the treatment of cancer. In an embodiment, the cancer is a B-cell proliferative disorder. In an embodiment, the cancer is a CD20-positive B-cell proliferative disorder. In an embodiment, the cancer is selected from a group consisting of non-Hodgkin lymphoma (NHL), acute lymphoblastic leukemia (ALL), chronic lymphocytic leukemia (CLL), diffuse large B-cell lymphoma (DLBCL), follicular lymphoma (FL), mantle cell lymphoma (MCL), marginal zone lymphoma (MZL), multiple myeloma (MM), and Hodgkin lymphoma (HL). In an embodiment, the therapeutic agent is an immunotherapeutic agent.

In some embodiments, the therapeutic agent contains an antibody specifically binding to activated T-cell antigen.

In an embodiment, the therapeutic agent contains an antibody specifically binding to CD3, particularly CD3ε.

In a specific embodiment, the disease is NHL, particularly relapsed/refractory (r/r) NHL. In an embodiment, the disease is DLBCL. In an embodiment, the disease is FL. In an embodiment, the disease is MCL. In an embodiment, the disease is MZL.

A method for treating a disease or disorder with the anti-CD20 antibody of the present disclosure includes the following steps: a therapeutically effective amount of antibody or antigen-binding fragment thereof or nucleic acid molecule or vector or cell or pharmaceutical composition of any one of the aforementioned aspects is administered to a mammal.

In some embodiments, the present disclosure provides a method for treating or preventing cancer, which includes the following steps: an antibody that can bind to CD20 is administered to a patient, so as to provide a serum level of at least 40 μg/mL. In different embodiments, the antibody is administered to provide at a serum level of at least 50 μg/mL, at least 150 μg/mL, at least 300 μg/mL, at least 400 μg/mL or at least 500 μg/mL. In different embodiments, the antibody is administered to provide a serum level of no more than 800 μg/mL, 700 μg/mL, 600 μg/mL, 550 μg/mL or 500 μg/mL. In an embodiment, the provided serum level is 40 μg/mL to 700 μg/mL, preferably 40 μg/mL to 600 μg/mL, preferably 50 μg/mL to 500 μg/mL, such as 150 μg/mL to 500 μg/mL and 300 μg/mL to 500 μg/mL. The term "serum level" as used in this description refers to the concentration of the substance in question in the serum. In an embodiment, the serum level is provided for at least 7 days or at least 14 days. In an embodiment, the method includes the following steps: the antibody is administered in a dose of at least 300 $mg/m^2$, such as at least 600 $mg/m^2$, preferably up to 1500 $mg/m^2$, up to 1200 $mg/m^2$ or up to 1000 $mg/m^2$.

In some embodiments, the present disclosure provides a method for treating or preventing cancer, which includes the following step: an antibody that can bind to CD20 is administered to a patient in a dose of at least 300 $mg/m^2$, such as at least 600 $mg/m^2$, and preferably up to 1500 $mg/m^2$, up to 1200 $mg/m^2$ or up to 1000 $mg/m^2$.

In some embodiments, the present disclosure provides a method for treating or preventing cancer, which includes the following steps: an antibody that can bind to CD20 is administered to a patient in whom the at least 50%, preferably 60%, 70%, 80% or 90%, of cancer cells are positive to CD20 and/or at least 40%, preferably 50% or 60%, of cancer cells are positive to the surface expression of CD20. In this aspect, the present disclosure also provides a method for treating or preventing cancer, which includes the following steps: a. at least 50%, preferably 60%, 70%, 80% or 90%, of CD20-positive cancer cells and/or at least 40%, preferably 50% or 60%, of cancer cells in a patient were identified and shown, the cancer cells are positive to the surface expression of CD20; and b. an antibody that can bind to CD20 is administered to the patient. In an embodiment, at least 95% or at least 98% of cancer cells in the patient are positive to CD20. In an embodiment, at least 70%, at least 80% or at least 90% of cancer cells in the patient are positive to the surface expression of CD20.

In an embodiment of the method of any aspect described herein, the outcome of cancer treatment is to achieve disease stabilization In an embodiment, the disease stabilization is achieved for at least 2 months, at least 3 months or at least 6 months.

In some embodiments, the present disclosure provides a method for achieving the disease stabilization of a cancer patient, which includes the following steps: an antibody that can bind to CD20 is administered to a patient. In an embodiment, the disease stabilization is achieved for at least 2 months, at least 3 months or at least 6 months.

In an embodiment of the method of any aspect described herein, the antibody is administered in a single dose or multiple doses.

In some embodiments, the present disclosure provides a method for treating or preventing cancer, which includes the following steps: an antibody that can bind to CD20 is administered to a patient in multiple doses.

In a case that the antibody is administered in multiple doses according to the present disclosure, the antibody is administered in preferably at least 3 doses, at least 4 doses, at least 5 doses, at least 6 doses, at least 7 doses, at least 8 doses, at least 9 doses or at least 10 doses, and preferably up to 30 doses, 25 doses, 20 doses, 15 doses or 10 doses. Doses of the antibody are preferably administered at intervals of at least 7 days, at least 10 days, at least 14 days or at least 20 days. Doses of the antibody are preferably administered at intervals of 7 to 30 days or 10 to 20 days, preferably about 14 days.

In an embodiment, the antibody is administered to provide a serum level of at least 40 μg/mL. In different embodiments, the antibody is administered to provide a serum level of at least 50 μg/mL, at least 150 μg/mL, at least 300 μg/mL, at least 400 μg/mL or at least 500 μg/mL. In different embodiments, the antibody is administered to provide a serum level of no more than 800 μg/mL, 700 μg/mL, 600 μg/mL, 550 μg/mL or 500 μg/mL. In an embodiment, the provided serum level is 40 μg/mL to 700 μg/mL, preferably 40 μg/mL to 600 μg/mL, preferably 50 μg/mL to 500 μg/mL, such as 150 μg/mL to 500 μg/mL or 300 μg/mL to 500 μg/mL. In an embodiment, the serum level is provided for at least 7 days or at least 14 days. In an embodiment, the method includes the following steps: the antibody is administered in a dose of at least 300 $mg/m^2$ such as at least 600 $mg/m^2$, and preferably up to 1500 $mg/m^2$, up to 1200 $mg/m^2$ or up to 1000 $mg/m^2$.

Use of the antibody or the antigen-binding fragment thereof or the nucleic acid or the vector or the cell or the pharmaceutical composition of any one of the aforementioned aspects in the preparation of a drug for treating a CD20-associated disorder in a mammal is provided.

According to any one of the aforementioned aspects, optionally, the antibody is conjugated to other drugs such as a labelled or cytotoxic conjugate.

In an aspect, the present disclosure also includes a kit. For example, the kit includes the antibody or a fragment or homologue or derivative thereof of the present disclosure, such as a labelled or cytotoxic conjugate, antibody operating instructions, a conjugate that kills specific types of cells, etc. The instructions may include directions for using the antibody, conjugate, etc. in vitro, in vivo, or ex vivo. The antibody may be in the form of a liquid or solid, and is usually lyophilized. This kit may contain other appropriate reagents, such as a buffer, a reconstitution solution, and other components necessary for the intended use. A reagent combination packaged in predetermined doses and instructions for its use are contemplated, and the use is, for example, therapeutic use or diagnostic assay. In a case that the antibody is labelled with, for example, an enzyme, the kit may include a substrate and a cofactor required for the enzyme (e.g., a substrate precursor that provides a detectable chromophore or fluorophore). In addition, other additives, such as a stabilizer and a buffer (e.g., a blocking buffer and a lysis buffer), may be included. The relative amounts of various reagents can be varied such that a concentrate of a reagent solution is provided, which achieves user flexibility, space savings, reagent savings, etc. These reagents may also be provided in the form of dry powder, usually in a lyophilized form, including an excipient, which can provide a reagent solution at an appropriate concentration when dissolved.

Use of the antibody or the functional fragment or the nucleic acid or the vector or the cell or the pharmaceutical composition or the kit of any one of the aforementioned aspects in the preparation of a reagent for inhibiting the binding to CD20 is provided.

In addition, the antibody of the present disclosure can also be used for immunoassay, a purification method, and other methods using immunoglobulins or fragments thereof. Such use is well-known to those skilled in the art.

Correspondingly, the present disclosure also provides a composition containing the anti-CD20 antibody or the fragment thereof of the present disclosure, and the antibody is conveniently combined with a pharmaceutically acceptable carrier, a diluent or an excipient, as is common practice in the art.

The term "pharmaceutical composition" refers to a preparation of various preparations. A preparation containing a therapeutically effective amount of polyvalent antibody is a sterile liquid solution, liquid suspension or lyophilized form, optionally containing a stabilizer or excipient.

The antibody of the present disclosure may be used as a composition that is administered alone, or used in combination with other active agents.

In some embodiments, the humanized antibody of the present disclosure is conjugated to a therapeutic moiety (i.e., a drug). The therapeutic moiety may be, for example, a cytotoxin, a chemotherapeutic agent, a cytokine, an immunosuppressive drug, an immunostimulant, a lytic peptide or a radioisotope. Such a conjugate is referred to as an "antibody-drug conjugate" or "ADC" herein.

In some embodiments, the antibody is conjugated to a cytotoxic moiety. The cytotoxic moiety may be selected from, for example, paclitaxel; cytochalasin B; gramicidin D; ethidium bromide; emetine; mitomycin; etoposide; teniposide; vincristine; vinblastine; colchicine; doxorubicin; daunorubicin; dihydroxy anthrenedione; a tubulin inhibitor such as maytansine or an analog or derivative thereof; an antimitotic agent such as monomethyl auristatins E or F or an analog or derivative thereof; dolastatin 10 or 15 or analogs thereof; irinotecan or an analog thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an anti-metabolite such as methotrexate, 6-mercaptopurine, 6-thioguanine, cytarabine, fludarabine, 5-fluorouracil, decarbazine, hydroxyure, asparaginase, gemcitabine, or cladribine; an alkylating agent such as dichloromethyldiethylamine, a thiopurine, chlorambucil, melphalan, carmustine (BSNU), lomustine (CCNU), cyclophosphamide, busulfan, dibromomannitol, streptozotocin, dacarbazine (DTIC), procarbazine, or mitomycin C; a platinum derivative such as cisplatin or carboplatin; duocarmycin A, duocarmycin SA, rachelmycin (CC-1065), or analogs or derivatives thereof; an antibiotic such as actinomycin, bleomycin, daunorubicin, doxorubicin, idarubicin, mithramycin, mitomycin, mitoxantrone, perimycin, anthramycin (AMC); pyrrolo [2,1-c][1,4]-benzodiazepine (PDB); diphtheria toxin and related molecules such as diphtheria A chain and an active fragment and a hybrid molecule thereof, ricin such as ricin A or deglycosylated ricin A chain toxin, cholera toxin, a Shiga-like toxin such as SLT I, SLT II, SLT IIV, LT toxin, C3 toxin, a Shiga toxin, pertussis toxin, tetanus toxin, a soybean Bowman-Birk protease inhibitor, *Pseudomonas* exotoxin, alorin, saporin, modeccin, gelanin, abrin A chain, modeccin A chain, α-sarcin, *Aleurites fordii* protein, dianthin protein, a *Phytolacca americana* protein such as PAPI, PAPII and PAP-S, a *Momordica charantia* inhibitor, curcin, crotin, a *Sapaonaria officinalis* inhibitor, gelonin, mitomycin, restrictocin, phenomycin, and enomycin toxin; ribonuclease (RNase); DNase I, Staphylococcal endotoxin A; pokeweed antiviral protein; diphtheria toxin and *Pseudomonas* endotoxin.

In some embodiments, the antibody is conjugated to an auristatin or a peptide analog, derivative or prodrug thereof. It has been shown that auristatins interfere with microtubule dynamics, GTP hydrolysis, and nuclear and cell division, and have anticancer and antifungal activity. For example, auristatin E can react with p-acetylbenzoic acid or benzoylvaleric acid to respectively produce AEB and AEVB. Other typical auristatin derivatives include AFP, monomethyl auristatin F (MMAF), and monomethyl auristatin E (MMAE). Appropriate auristatins and analogs, derivatives, and prodrugs thereof, as well as appropriate adaptor for conjugating auristatins to Ab are described in, for example, U.S. Pat. Nos. 5,635,483, 5,780,588 and 6,214,345, as well as international patent application publications WO02088172, WO2004010957, WO2005081711, WO2005084390, WO2006132670, WO03026577, WO200700860, WO207011968 and WO205082023.

In some embodiments, the antibody is conjugated to pyrrolo[2,1-c][1,4]-benzodiazepine (PDB) or a peptide analog, derivative or prodrug thereof. Appropriate PDB and PDB derivatives as well as related technologies are described in, for example, Hartley J. A. et al., Cancer Res 2010; 70 (17): 6849-6858; Antonow D. et al., Cancer J 2008; 14 (3): 154-169; Howard P. W. et al., Bioorg Med Chem Lett 2009; 19: 6463-6466, and Sagnou et al., Bioorg Med Chem Lett 2000; 10 (18): 2083-2086.

In some embodiments, the antibody is conjugated to a cytotoxic moiety of an anthracycline, maytansine, a calicheamicin, duocarmycin, rapamycin (CC-1065), dolastatin 10, dolastatin 15, irinotecan, monomethyl auristatin E, monomethyl auristatin F, PDB, or any analog, derivative or prodrug thereof.

In some embodiments, the antibody is conjugated to an anthracycline, or an analog, derivative or prodrug thereof. In some embodiments, the antibody is conjugated to maytansine, or an analog, derivative or prodrug thereof. In some embodiments, the antibody is conjugated to a calicheamicin, or an analog, derivative or prodrug thereof In some embodiments, the antibody is conjugated to duocarmycin, or an analog, derivative or prodrug thereof In some embodiments, the antibody is conjugated to rapamycin (CC-1065), or an analog, derivative or prodrug thereof In some embodiments, the antibody is conjugated to dolastatin 10, or an analog, derivative or prodrug thereof. In some embodiments, the antibody is conjugated to dolastatin 15, or an analog, derivative or prodrug thereof. In some embodiments, the antibody is conjugated to monomethyl auristatin E, or an analog, derivative or prodrug thereof In some embodiments, the antibody is conjugated to monomethyl auristatin F, or an analog, derivative or prodrug thereof. In some embodiments, the antibody is conjugated to pyrrolo [2,1-c][1,4]-benzodiazepine, or an analog, derivative or prodrug thereof. In some embodiments, the antibody is conjugated to irinotecan, or an analog, derivative or prodrug thereof.

In some embodiments, the antibody is conjugated to a cytokine (e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa).

In some embodiments, the antibody is conjugated to a radioisotope or a chelate containing a radioisotope. For example, the antibody may be conjugated to a chelate adaptor (e.g., DOTA, DTPA, and thiacetam) that allows the antibody to be complexed with the radioisotope. The antibody may also or optionally contain one or more radiolabeled amino acids or other radiolabeled molecules or is conjugated to the radiolabeled amino acids or radiolabeled molecules. Radioisotopes include, but are not limited to, $^{3}H$, $^{14}C$, $^{15}N$, $^{35}S$, $_{90}Y$, $^{99}Tc$, $^{125}I$, $^{131}I$, $^{186}Re$, $^{213}Bi$, $^{225}$ Ac, and $^{227}Th$. For therapeutic purposes, radioisotopes that emit β or a particle radiation, such as $^{131}I$, $^{90}Y$, $^{211}At$ $^{212}Bi$, $^{67}Cu$, $^{186}Re$, $^{188}Re$, and $^{212}Pb$, may be used.

The technologies for conjugating molecules to antibodies are well-known in the art. Usually, a nucleic acid molecule is covalently linked to lysine or cysteine on an antibody through an N-hydroxysuccinimide eater or maleimide functional group. It is reported that the homogeneity of a conjugate can be improved by conjugation methods using engineered cysteine or integrating unnatural amino acids. Particularly, those skilled in the art can also expect to use a tag (e.g., a tag containing Gin peptide and a Q-tag) containing glutamine serving as an acyl donor or polypeptide engineering (e.g., amino acid deletions, insertions, substitutions and mutations on a polypeptide) to generate a reactive endogenous glutamine engineered Fc-containing polypeptide. Then, a transglutaminase can be covalently cross-linked with an amine donor agent (e.g., a small molecule containing or linked to a reactive amine) to form a population of stable and homogeneous engineered Fc-containing polypeptide conjugates in which the amine donor agent is specifically conjugated to the Fc-containing polypeptide through the tag containing glutamine serving as an acyl donor tag or accessible/exposed/reactive endogenous glutamine sites (WO2012059882).

It should be understood that therapeutic agents according to the described embodiments will be administered with suitable pharmaceutically acceptable carriers, excipients, and other reagents incorporated into the preparation to provide improved transfer, delivery, tolerability, etc. A large number of appropriate preparations can be found in the pharmacopoeia known to all medicinal chemists: Remington's Pharmaceutical Sciences (the 15th edition, Mack Publishing Company, Easton, Pa. (1975)), especially Chapter 87 of Blaug and Seymour therein. These preparations include, for example, powders, pastes, ointments, gels, waxes, oils, lipids, lipid-containing (cation or anion) carriers (such as Lipofectin™), DNA conjugates, anhydrous slurries, oil-in-water and water-in-oil emulsions, emulsion polyethylene glycols (polyethylene glycols of various molecular weights), semisolid gels, and semisolid mixtures containing polyethylene glycol. Any of the above mixtures is applicable to the treatment or therapy according to the present disclosure under the conditions that an active ingredient of the preparation is not inactivated by the preparation, and the preparation is physiologically compatible and tolerates the route of administration.

In an embodiment, the antibody can be used as a therapeutic agent. Such a therapeutic agent is usually used for treating, alleviating and/or preventing a disease or pathology associated with aberrant CD20 expression, activity and/or signaling in a subject. A treatment regimen can be implemented using standard methods by identifying a subject, such as a human patient suffering from (or at risk of or developing) CD20-associated symptoms such as a disease or disorder associated with aberrant CD20 expression, activity and/or signaling. An antibody preparation, preferably an antibody preparation with high specificity and high affinity for its target antigen, is administered to a subject and will generally produce an effect due to its binding to the target.

The administered antibody can eliminate or inhibit or hinder the expression, activity and/or signal transduction function of the target (e.g., CD20). The administered antibody can eliminate or inhibit or hinder the binding of the target (e.g., CD20) to an endogenous ligand to which it naturally binds. For example, the antibody binds to the target and regulates, blocks, inhibits, reduces, antagonizes, neutralizes and/or hinders the expression, activity and/or signal transduction of CD20 in other ways. In some embodiments, in order to treat an abnormal CD20 expression-associated disease or disorder, an antibody having heavy chain and light chain CDRs can be administered to a subject.

In another embodiment, antibodies against CD20 can used in methods known in the art related to CD20 localization and/or quantification (e.g., measurement of CD20 and/or a CD20 level in an appropriate physiological sample, diagnostic methods, and protein imaging). In a given embodiment, an antibody having the specificity for CD20 or a derivative, fragment, analog or homolog thereof and containing an antigen-binding domain derived from the antibody is used as a pharmaceutically active compound (referred to as a "therapeutic agent" hereinafter).

In another embodiment, an antibody having the specificity for CD20 is used for separating CD20 polypeptide through a standard technology such as immunoaffinity, chromatography and immunoprecipitation. An antibody (or a fragment thereof) against CD20 protein can be used for detecting proteins in a biological sample. In some embodiments, detection of CD20 in a biological sample can be used as part of a clinical testing procedure, for example, used for determining the efficacy of a given treatment regimen. Detection can be facilitated by conjugating (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, and acetylcholinesterase; examples of suitable prosthetic groups include streptavidin/biotin and avidin/biotin; examples of suitable fluorescent materials include umbelliferone, fluorescein, fluorescein isothiocyanate, rhodamine, dichlorotriazine fluorescein, dansyl chloride, and phycoerythrin; an example of the luminescent material includes luminol; examples of the bioluminescent materials include luciferase, fluorescein and aequorin, and examples of suitable radioactive materials include $^{125}I$, $^{131}I$, $^{35}S$, and $^{3}H$.

In another embodiment, the antibody of the present disclosure can be used as a reagent for detecting the presence of CD20 or a protein fragment thereof in a sample. In some embodiment, the antibody contains a detectable label. The antibody is a polyclonal antibody, or more preferably a monoclonal antibody. The whole antibody or a fragment (e.g., Fab, scFv, and F(ab')2) is used. The term "label" with respect to an antibody is intended to include direct labelling of the antibody by conjugating (i.e., physically linking) a detectable substance to the antibody, and indirect labelling of the antibody by reaction with another directly labelled reagent. Examples of indirect labelling include detection of a primary antibody with a fluorescently-labelled secondary antibody, and end-labelling of the antibody with biotin to enable detection with fluorescently-labeled streptavidin. The term "biological sample" is intended to include tissues, cells, and biological fluids separated from a subject, as well as tissues, cells, and fluids present in the subject. Therefore, the term "biological sample" used includes blood and fractions or components of blood, including serum, plasma, and lymph. In other words, the detection method of the embodiment can be used to detect an analyte mRNA, protein or genomic DNA in a biological sample both in vitro and in vivo. For example, the analyte mRNA in-vitro detection technologies include Norhtern hybridization and in situ hybrization. The analyte protein in-vitro detection technologies include enzyme-linked immunosorbent assay (ELISA), Western blotting, immunoprecipitation, and immunofluorescence. The analyte genomic DNA in-vitro detection technologies include Southern hybrization. Immunoassay procedures are described, for example, in "ELISA: Theory and Practice: Methods in Molecular Biology", Volume 42, J. R. Crowther (editor) Human Press, Totowa, N. J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. In addition, the analyte protein in-vivo detection technologies include introduction of a labelled anti-analyte protein antibody into a subject. For example, the antibody may be labelled with a radioactive label, and the presence and position of the radioactive label in the subject are detected by the standard imaging technology.

The antibody or the derivative, fragment, analog and homolog thereof described herein can be incorporated into pharmaceutical composition suitable for administration. The principles and considerations involved in the preparation of such a composition and guidance for selecting components are well known in the art, for example, with reference to Remington's Pharmaceutical Sciences: The Science And Practice Of Pharmacy, 19th edition (Alfonso R. Gennaro et al. eds) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Volume 4), 1991, M. Dekker, New York.

Such a composition usually contains an antibody and a pharmaceutically acceptable carrier. In a case that an antibody fragment is used, the minimum inhibitory fragment that specifically binds to a binding domain of a target protein may be preferred. For example, based on the variable region of the antibody, a peptide molecule that retains the ability to bind to the sequence of the target protein can be designed. Such a peptide can by chemically synthesized and/or by DNA recombination (referring to, for example, Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial agents and antifungal agents, isotonic agents and absorption delaying agents, etc., compatible with pharmaceutical administration. Suitable pharmaceutically acceptable carriers are described in the latest edition of Remington's Pharmaceutical Sciences, which is a standard reference work in the art and incorporated herein by reference. Preferred examples of such carriers or diluents include, but are not limited to, water, saline, Ringer's solution, dextrose solution, and 5% human serum albumin. Liposomes and non-aqueous carriers, such as immobilized oils, can also be used. The use of such media and reagents for pharmaceutically active substances is well known in the art. Except for their incompatibility with the antibody, use of any conventional medium or reagent in the composition is envisioned.

The pharmaceutical composition of the embodiment is prepared to be compatible with its intended route of administration. Examples of routes of administration include parenteral administration, such as intravenous, intradermal, subcutaneous, oral (e.g., inhalation), transdermal (i.e., topical), transmucosal and rectal administration. A solution or suspension for parenteral, intradermal or subcutaneous administration may include the following components: a sterile diluent for injection such as water, a saline solution, a fixed oil, polyethylene glycol, glycerin, propylene glycol, or other synthesized solvent; an antibacterial agent such as benzyl alcohol or methylparaben; an antioxidant such as ascorbic acid or sodium bisulfite; a chelating agent such as ethylenediaminetetraacetic acid (EDTA); a buffer such as acetate, citrate, or phosphate; and a reagent that regulates osmotic pressure such as sodium chloride or dextrose. The pH can be regulated with an acid or base, such as hydrochloric acid or sodium hydroxide. A parenteral administration may be packaged into an ampoule, a disposable syringe or a glass or plastic multi-dose vial.

Pharmaceutical composition suitable for injection includes sterile aqueous solutions (water-soluble herein) or dispersions and sterile powders for the extemporaneous preparation of sterile injectable solutions or dispersions. For intravenous administration, suitable pharmaceutically acceptable carriers include normal saline, bacteriostatic water, Cremophor EL™ (BASF, Parsippany, N.J.) or phosphate buffered saline (PBS). In all cases, the composition is required to be sterile and should be fluid to the extent of ease of injection. The composition is required to be stable under the preparation and storage conditions and is required to prevent the contamination of microorganisms such as bacteria and fungi. The carrier may be a solvent or dispersion medium containing, for example, water, ethanol, and polyol (e.g., glycerin, propylene glycol, and liquid polyethylene glycol), or an appropriate mixture thereof. For example, for a dispersion, the required particle size is maintained through a coating such as lecithin, and appropriate liquidity can be kept through a surfactant. The action of microorganisms can be prevented through various antibacterial and antifungal agents, such as a paraben, chlorobutanol, phenol, ascorbic acid, and thimerosal. In many cases, the composition preferably contains an isotonic agent, such as saccharide, a polyol (such as mannitol and sorbitol), and sodium chloride. Absorption of the composition for injection can be prolonged by adding a reagent for delaying absorption, such as aluminum monostearate and gelatin, in the composition.

As required, a sterile injectable solution can be prepared by incorporating a required amount of antibody into a suitable solvent with one or a combination (as required) of the ingredients enumerated above, filtering, and sterilizing In general, a dispersion is prepared by incorporating an antibody into a sterile carrier containing an alkaline dispersion medium and required other ingredients among those enumerated above. For sterile powder for preparation of a sterile injectable solution, the preparation methods are vacuum-drying and freeze-drying to obtain powder that contains an active ingredient and any additional desired ingredient from a sterile-filtered solution of these ingredients described above.

For inhalation administration, a compound is delivered as an aerosol spray from a pressurized vessel or dispenser or nebulizer containing a suitable propellant, such as a gas such as carbon dioxide.

Systemic administration can also be performed via transmucosal or transdermal routes. For transmucosal or transdermal administration, a penetrant suitable for permeating the barrier is used in a preparation. Such a penetrant is generally known in the art and includes, for example, a detergent, a bile salt and a fusidic acid derivative for transmucosal administration. Transmucosal administration can be performed by using a nasal spray or suppository. For transdermal administration, one or more antibodies can be prepared into a paste, ointment, gel or cream as generally known in the art.

The compound can also be prepared into the form of suppository (e.g., with a conventional suppository base such as cocoa butter and other glycerides) or retention enema for delivery via the rectum.

In an embodiment, the antibody can be prepared with a carrier that will protect the antibody from rapid elimination from the body, such as a sustained release/controlled release preparation, including an implant and a microencapsulated delivery system. Biodegradable or biocompatible polymers such as ethylene vinyl acetate, a polyanhydride, polyglycolic acid, collagen, a polyorthoester, and polylactic acid, can be used. Preparation methods of such preparations are apparent to those skilled in the art.

It is especially advantageous to prepare parenteral compositions in the dose unit form for ease of administration and uniformity of dose. As used herein, the dose unit form refers to a physically separable unit suitable as a unit dose for a subject to be treated; and each unit contains predetermined amounts of one or more antibodies that are calculated to achieve a desired therapeutic effect when used in combination with a required drug carrier. The specification for the dose unit form of the embodiment is dictated by and directly dependent on the unique characteristics of the antibody and a particular therapeutic effect to be achieved, and the limitations inherent in the art of formulation of such antibodies for treatment of individuals.

The pharmaceutical composition may be placed in a vessel, pack or dispenser together with instructions for administration.

The preparation described herein may also contain more than one antibody, preferably those with complementary activities that do not adversely affect each other, depending on the particular condition to be treated. Alternatively or in addition, a composition may contain, for example, an agent that enhances its function, such as a cytotoxic agent, a cytokine, a chemotherapeutic agent, or a growth inhibitor. Such molecules are appropriately present together in amounts effective for the intended purpose. For example, the molecules may be present together in a kit or use together. In an embodiment, one or more antibodies can be administered in combination treatment, that is, administered in combination with other agents such as a therapeutic agent (which can be used for treating a pathological condition or disorder, such as various forms of cancer, autoimmune disorders and inflammatory diseases). The term "combination" herein refers to substantially synchronous, simultaneous or sequential administration of reagents. In a case of sequential administration, when a second compound is started to be administered, a first compound of the two compounds is still preferably detected at a treatment site at an effective concentration. In one case, "combination" may also be that the kit contains both the antibody of the present disclosure and other therapeutic agents.

For example, combination treatment may include co-preparation and/or co-administration of one or more antibodies described herein and one or more additional therapeutic agents (e.g., one or more cytokine and growth factor inhibitors, immunosuppressants, anti-inflammatory agents, metabolic inhibitors, enzyme inhibitors, and/or cytotoxins or cytostatic agents, as described in more detail below). Such combination treatment can advantageously utilize lower doses of the therapeutic agents administered, thus avoiding possible toxicity or complications associated with various monotherapies.

In an embodiment, the administration of the anti-CD20 antibody and the therapeutic agent can reduce the number of B cells in the subject.

In an embodiment, compared with a corresponding therapeutic regimen without administration of the anti-CD20 antibody, the therapeutic regimen effectively reduces the cytokine release in the subject that is associated with the administration of the T cell activation therapeutic agent.

For purposes of clarity and conciseness of description, features are described herein as part of the same or separate embodiments. However, it should be understood that the scope of the present disclosure may include some embodiments with combinations of all or some of the described features.

Example 1 CD20 Stably Transfected Cells and Recombinant CD3 Antigen

1. Construction of Human or Monkey CD20 Stably Transfected Line

A lentiviral vector plasmid containing a human CD20 or cynomolgus monkey CD20 full-length sequence (cDNA purchased from Sino Biological, HG11007-UT, CG90052-G) was constructed, the constructed lentiviral plasmid and a packaging plasmid were co-transfected into HEK293T cells by using a lentivirus packaging kit (Lenti-Pac HIV Expression Packaging Kit, Gene Copoeia, #HPK-LvTR-20), and a supernatant was collected after 48 h. 10 μL of culture supernatant containing lentiviral particles was added to CHO cells in the logarithmic growth phase, and after 2 days, 10 μg/mL puromycin was added for screening. Resistant clones were subjected to limiting dilution to further obtain a stably transfected cell line CHO-human CD20 (clone 3G6) or CHO-cynomolgus monkey CD20 (clone 1G9) highly expressing human or monkey CD20.

FIG. 1 shows that flow cytometry results of an APC-labelled CD20 antibody (BioLegend #302309), compared with untransfected CHO cells, both the human CD20 stably transfected cells (CHO-hCD20-3G6) and the monkey CD20 stably transfected cells (CHO-cyCD20-1G9) express high levels of CD20.

2. Construction of Human or Monkey CD3εγ Heterodimer

Figure 2:
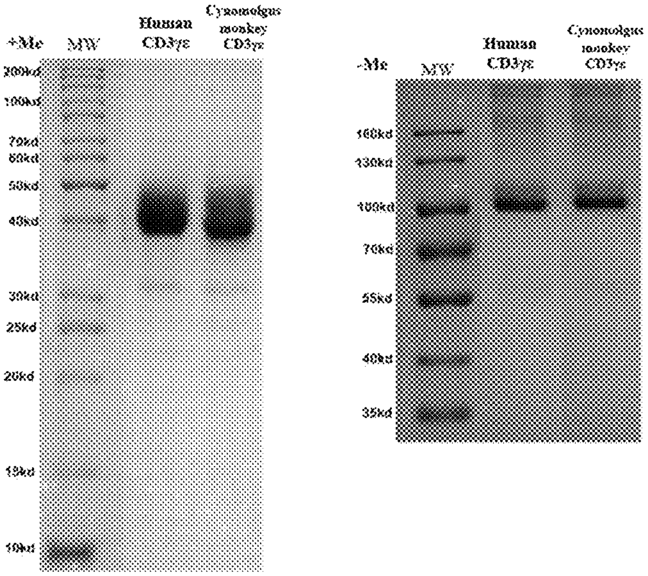
FIG. 2 shows SDS-PAGE results of recombinant CD3εγ-Fc protein.

Nucleotide sequences of extracellular regions of human CD3γ (UniProt P09693, $Gln_{23}$-$Asn_{116}$) and CD3ε (UniProt P07766, $Gln_{23}$-$Asp_{126}$) were synthesized, C-termini were respectively fused with human IgG Fc hole or Fc knob, and a human CD3εγ-Fc heterodimer was formed by expression (an amino acid sequence of human CD3γ IgG Fc (hole) is shown as SEQ ID NO: 1, and an amino acid sequence of human CD3ε IgG Fc (knob) is shown as SEQ ID NO: 2). Similarly, cynomolgus monkey CD3γ (UniProt Q95LI7, $Gln_{23}$-$Asn_{110}$) and CD3ε (UniProt Q95LI5, $Gln_{22}$-$Asp_{117}$) were synthesized, C-termini were respectively fused with cynomolgus monkey IgG Fc hole or Fc knob, a cynomolgus monkey CD3εγ-Fc heterodimer was formed by expression (an amino acid sequence of cynomolgus monkey CD3γ IgG Fc (hole) is shown as SEQ ID NO: 3, and an amino acid sequence of cynomolgus monkey CD3γ IgG Fc (knob) is shown as SEQ ID NO: 4). A recombinant plasmid expressing CD3γ -Fc and CD3ε-Fc was mixed with 3 mg/mL PEI (Polysciences, #24765-2), co-transfected into HEK293E cells (culture medium OPM-293 CD03 DPM), and cultured at 37° C. and 120 rpm under 5% $CO_2$ for 7 d, a culture supernatant was collected and purified by Protein A affinity chromatography to obtain a recombinant human or cynomolgus monkey CD3εγ-Fc protein with the SDS-PAGE purity higher than 95% (see FIG. 2).

Example 2 Humanized Anti-CD3 Antibodies

A murine anti-hybridoma CD3 antibody (EMBO J.1985. 4 (2): 337-344; J. Immunol. 1986, 137 (4): 1097-100; J. Exp. Med. 1991, 174: 319-326; J. Immunol. 1991,147 (9): 3047-52) recognizes human and monkey CD3 receptors, and its sequence is as follows:

amino acid sequence of a light chain of the anti-CD3 mouse monoclonal antibody (SEQ ID NO: 122):
QAVVTQESALTTSPGETVTLTCRSSTGAVTTSNYANWVQQKPDHLFTGL
IGGTNKRAPGVPARFSGSLIGDKAALTITGAQTEDEAIYFCALWYSNLW
VFGGGTKLTVL amino acid sequence of a heavy chain of the anti-CD3 mouse monoclonal antibody (SEQ ID NO: 123):
EVQLVESGGGLVQPKGSLKLSCAASGFTFNTYAMNWVRQAPGKGLEWVA
RIRSKYNNYATYYADSVKDRFTISRDDSQSILYLQMNNLKTEDTAMYYC
VRHGNFGNSYVSWFAYWGQGTLVTVSS The anti-CD3 mouse monoclonal antibody was humanized Human germline gene IMGT_hVL7-43 with the highest homology was selected for light chain CDR transplantation, and human IGLJ3*02 was selected as FM4. Human IMGT_hVH3-73 was selected for heavy chain CDR transplantation, and human IGHJ4*01 was selected as FM4. Different heavy chain variants and light chain variants were designed and obtained (see Tables 1 and 2).

TABLE 1

Light chain variable region sequences of humanized anti-CD3 antibodies

| | SEQ ID NOs: 5-23 | | | | |
|---|---|---|---|---|---|
| | LCVR | | LCDR1 | LCDR2 | LCDR3 |
| Humanized anti-CD3 antibody | Amino acid sequence | Nucleotide sequence | Amino acid sequence | Amino acid sequence | Amino acid sequence |
| hVL1 | 5 | 6 | 7 | 8 | 9 |
| hVL2 | 10 | 11 | 7 | 8 | 9 |
| hVL3 | 12 | 13 | 14 | 15 | 9 |
| hVL4 | 16 | 17 | 14 | 15 | 9 |
| hVL5 | 18 | 19 | 7 | 8 | 21 |
| hVL6 | 22 | 23 | 7 | 20 | 21 |

hVL1:
QAVVTQEPSLTVSPGGTVTLTCRSSTGAVTTSNYANWVQQKPGQAPRGL
IGGTNKRAPWTPARFSGSLLGGKAALTLSGAQPEDEAEYYCALWYSNLW
VFGGGTKLTVL hVL2:
QAVVTQEPSLTVSPGGTVTLTCRSSTGAVTTSNYANWVQEKPGQAPRGL
IGGTNKRAPWTPARFSGSLLGGKAALTLSGAQPEDEAEYYCALWYSNLW
VFGGGTKLTVL hVL3:
EAVVTQEPSLTVSPGGTVTLTCESSDGAVTTSNYANWVQEKPGQAPRGL
IGGTNKEAPWTPARFSGSLLGGKAALTLSGAQPEDEAEYYCALWYSNLW
VFGGGTKLTVL hVL4:
QAVVTQEPSLTVSPGGTVTLTCESSDGAVTTSNYANWVQEKPGQAPRGL
IGGTNKEAPWTPARFSGSLLGGKAALTLSGAQPEDEAEYYCALWYSNLW
VFGGGTKLTVL

-continued hVL5:
QAVVTQEPSLTVSPGGTVTLTCRSSTGAVTTSNYANWVQEKPGQAPRGL
IGGTNKRAPWTPARFSGSLLGGKAALTITGAQAEDEAEYYCVLWYSNLW
VFGGGTKLTVL hVL6:
QAVVTQEPSLTVSPGGTVTLTCRSSTGAVTTSNYANWFQEKPGQAPRGL
IYGTNKRAPWTPARFSGSLLGGKAALTLSGAQAEDEAEYYCVLWYSNLW
VFGGGTKLTVL

TABLE 2

Heavy chain variable region sequences of humanized anti-CD3 antibodies

| | SEQ ID NOs: 24-53 | | | | |
|---|---|---|---|---|---|
| | HCVR | | HCDR1 | HCDR2 | HCDR3 |
| Humanized anti-CD3 antibody | Amino acid sequence | Nucleotide sequence | Amino acid sequence | Amino acid sequence | Amino acid sequence |
| hVH1 | 24 | 25 | 26 | 27 | 28 |
| hVH2 | 29 | 30 | 31 | 27 | 28 |
| hVH3 | 32 | 33 | 31 | 27 | 34 |
| hVH4 | 35 | 36 | 31 | 27 | 37 |
| hVH5 | 38 | 39 | 31 | 27 | 40 |
| hVH6 | 41 | 42 | 31 | 27 | 43 |
| hVH7 | 44 | 45 | 46 | 47 | 28 |
| hVH8 | 48 | 49 | 26 | 27 | 28 |
| hVH9 | 50 | 51 | 26 | 27 | 28 |
| hVH10 | 52 | 53 | 26 | 27 | 28 |

hVH1:
EVQLVESGGGLVQPGGSLRLSCAASGFTFNTYAMNWVRQAPGKGLEWVS
RIRSKYNNYATYYADSVKDRFTISRDDSKNTLYLQMNSLRAEDTAVYYC
VRHGNFGNSYVSWFAYWGQGTLVTVSS hVH2:
EVQLVESGGGLVQPGGSLRLSCAASGFTFSTYAMNWVRKAPGKGLEWVS
RIRSKYNNYATYYADSVKDRFTISRDDSKNTLYLQMNSLRAEDTAVYYC
VRHGNFGNSYVSWFAYWGQGTLVTVSS hVH3:
EVQLVESGGGLVQPGGSLRLSCAASGFTFSTYAMNWVRKAPGKGLEWVS
RIRSKYNNYATYYADSVKDRFTISRDDSKNTLYLQMNSLRAEDTAVYYC
VRHGNFGESYVSWFAYWGQGTLVTVSS hVH4:
EVQLVESGGGLVQPGGSLRLSCAASGFTFSTYAMNWVRKAPGKGLEWVS
RIRSKYNNYATYYADSVKDRFTISRDDSKNTLYLQMNSLRAEDTAVYYC
VRHGNFGQSYVSWFAYWGQGTLVTVSS hVH5:
EVQLVESGGGLVQPGGSLRLSCAASGFTFSTYAMNWVRKAPGKGLEWVS
RIRSKYNNYATYYADSVKDRFTISRDDSKNTLYLQMNSLRAEDTAVYYC
VRHGNFGDSYVSWFAYWGQGTLVTVSS hVH6:
EVQLVESGGGLVQPGGSLRLSCAASGFTFSTYAMNWVRKAPGKGLEWVS
RIRSKYNNYATYYADSVKDRFTISRDDSKNTLYLQMNSLRAEDTAVYYC
VRHGNFGTSYVSWFAYWGQGTLVTVSS hVH7:
EVQLVESGGGLVQPGGSLRLSCAASGFTFSDYAMNWVRKAPGKGLEWVS
RIRSKYNNYATYYADSVEDRFTISRDDSKNTLYLQMNSLRAEDTAVYYC
VRHGNFGNSYVSWFAYWGQGTLVTVSS hVH8:
EVQLVESGGGLVQPGGSLRLSCAASGFTFNTYAMNWVRKAPGKGLEWVG
RIRSKYNNYATYYADSVKDRFTISRDDSKNSLYLQMNSLKTEDTAVYYC
ARHGNFGNSYVSWFAYWGQGTLVTVSS

-continued hVH9:
EVQLVESGGGLVQPGGSLRLSCAASGFTFNTYAMNWVRKAPGKGLEWVG
RIRSKYNNYATYYADSVKDRFTISRDDSKNSLYLQMNSLKTEDTAVYYC
VRHGNFGNSYVSWFAYWGQGTLVTVSS hVH10:
EVQLVESGGGLVQPGGSLRLSCAASGFTFNTYAMNWVRKAPGKGLEWVA
RIRSKYNNYATYYADSVKDRFTISRDDSKNSLYLQMNSLKTEDTAVYYC
VRHGNFGNSYVSWFAYWGQGTLVTVSS After the complete sequences being respectively synthesized, the humanized light and heavy chain variants were cloned into a eukaryotic expression vector containing an antibody lambda light chain constant region or human IgG4 heavy chain constant regions CH1-CH3, co-transfected into HEK293E cells, and cultured at 37° C. and 120 rpm under 5% $CO_2$ for 5-6 d, and a culture supernatant was collected and purified through a Protein A chromatographic column.

ELISA Affinity Assay

Human CD3εγ protein was coated onto a plate and placed at 4° C. overnight. After the human CD3εγ protein was blocked with 2% skimmed milk, CD3 antibodies with different dilution ratios were added to the wells, the mixture was incubated for 1 h, HPR-labelled goat anti-human IgG Fc was added as a secondary antibody, and after a TMB solution was added for color developing, the reaction was terminated with concentrated sulfuric acid, and the absorbance at 450 nm was read (results are shown in FIG. 3).

Figure 3:
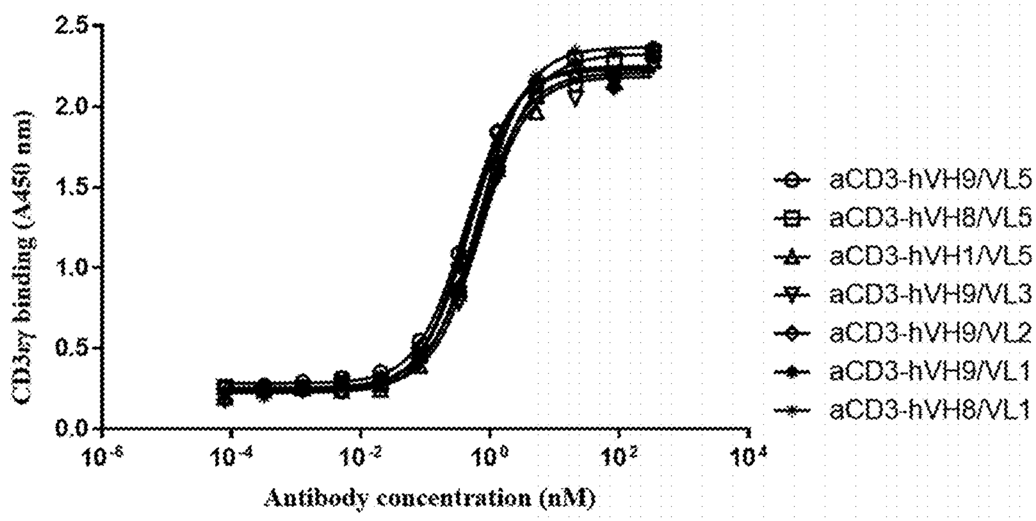
FIG. 3 shows the binding of a humanized CD3 antibody to recombinant CD3εγ-Fc protein.

FIG. 3 shows a combination of humanized anti-CD3 antibodies (including aCD3-hVH8/VL1, aCD3-hVH9/VL1, aCD3-hVH9/VL2, aCD3-hVH9/VL3, aCD3-hVH1/VL5, aCD3-hVH8/VLS, and aCD3-hVH9/VL5) binding to human CD3εγ protein, and the humanized anti-CD3 antibody binds to recombinant CD3ελ protein with high affinity.

Jurkat T Cell Affinity Assay

Jurkat cells in the logarithmic growth phase were taken, blocked with 3% BSA for 30 min, added to a 96-well U-shaped plate according to a density of $5\times10^4$ cells per well, and centrifuged, a supernatant was discarded, 50 μL of gradient-diluted antibody (the initial concentration of 30 μg/mL, 3-fold dilution, 5 gradients) was added to each well, and the mixture was incubated at 4° C. for 1 h. After the primary antibody was washed away, Alexa Fluro647-labelled goat anti-human IgG Fc (Jackson ImmunoResearch, 109-606-170) diluted in 1:300 was added as a secondary antibody, the mixture was incubated at 4° C. for 45 min, and after being washed, cells in each well were resuspended in 50 μL of PBS for FACS (iQue, Intellicyt) (results are shown in FIG. 4).

Figure 4:
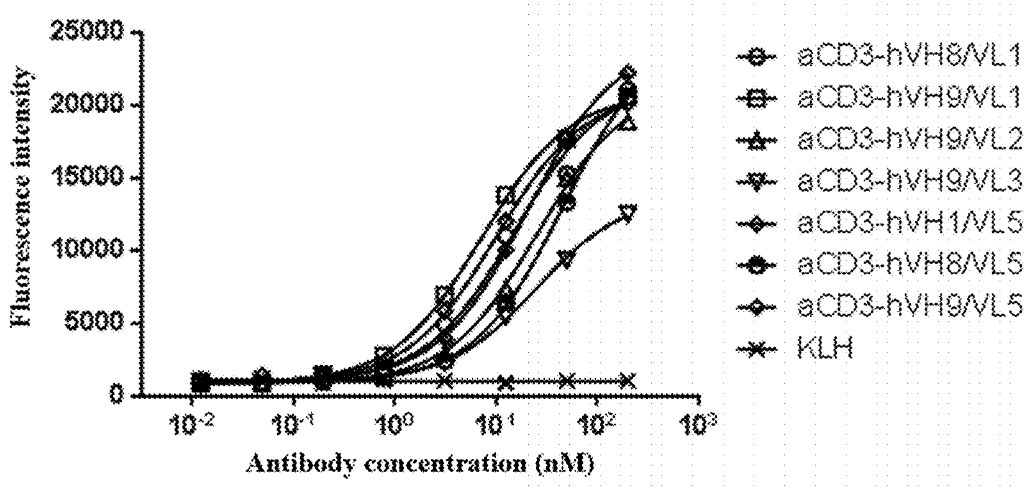
FIG. 4 shows the binding of a humanized CD3 antibody to Jurkat cells.

FIG. 4 shows a combination of humanized anti-CD3 antibodies binding to Jurkat cells, and the humanized anti-CD3 antibody hVH9/VL5 (aCD3-hVH9/VL5) binds to Jurkat cells with moderate affinity.

Example 3 Humanized Anti-CD20 Antibodies

Murine anti-CD20 antibodies or control antibodies were synthesized with reference to documents U.S. Pat. Nos. 5,736,137 and 8,529,902. Amino acid sequences of variable regions of the antibodies are as follows:

CD20-2B8:
QIVLSQSPAILSASPGEKVTMTCRASSSVSYIHWFQQKPGSSPKPWIYA
TSNLASGVPVRFSGSGSGTSYSLTISRVEAEDAATYYCQQWTSNPPTFG
GGTKLEIK
QVQLQQPGAELVKPGASVKMSCKASGYTFTSYNMHWVKQTPGRGLEWIG
AIYPGNGDTSYNQKFKGKATLTADKSSSTAYMQLSSLTSEDSAVYYCAR
STYYGGDWYFNVWGAGTTVTVSA

-continued

```
CD20-2F2:
EIVLTQSPATLSLSPGERATLSCRASQSVSSYLAWYQQKPGQAPRLLIY
DASNRATGIPARFSGSGSGTDFTLTISSLEPEDFAVYYCQQRSNWPITF
GQGTRLEIK
EVQLVESGGGLVQPGRSLRLSCAASGFTFNDYAMHWVRQAPGKGLEWVS
TISWNSGSIGYADSVKGRFTISRDNAKKSLYLQMNSLRAEDTALYYCAK
DIQYGNYYYGMDVWGQGTTVTVSS

CD20-11B8:
EIVLTQSPATLSLSPGERATLSCRASQSVSSYLAWYQQKPGQAPRLLIY
DASNRATGIPARFSGSGSGTDFTLTISSLEPEDFAVYYCQQRSDWPLTF
GGGTKVEIK
EVQLVQSGGGLVHPGGSLRLSCTGSGFTFSYHAMHWVRQAPGKGLEWVS
IIGTGGVTYYADSVKGRFTISRDNVKNSLYLQMNSLRAEDMAVYYCARD
YYGAGSFYDGLYGMDVWGQGTTVTVSS
```

Through CDR transplantation and point mutation, the anti-CD20 antibodies were optimally designed and the iso-electric point was lowered: a light chain CDR of the murine or control anti-CD20 antibody was transplanted to the framework of human antibody germline gene Vk3-20, and human KJ2*01 was used as the Joint region. A heavy chain CDR was transplanted to the framework of human VH1-69 or VH3-23, a mutation such as $Lys_{77}Asn$ was introduced to reduce the charge density of the Fv region, and human HJ4*01 was used as the Joint region. Thus, humanized Mab001 antibody, Mab002 antibody, Mab003 antibody, Mab004 antibody, Mab005 antibody, Mab006 antibody, and Mab007 antibody Mab007 were respectively obtained (see Tables 3 and 4).

A light chain variable region was cloned into a eukaryotic expression vector containing the kappa light chain constant region, and a heavy chain variable region was cloned into a eukaryotic expression vector containing the IgG4 CH1-3 constant regions. HEK293E cells were transfected, and after 5-6 days of expression, a culture supernatant was collected and purified by Protein A affinity chromatography, and the antibody concentration was determined by using a Nanodrop spectrophotometer based on the theoretical absorbance.

TABLE 3

Light chain variable region sequences of humanized anti-CD20 antibodies

| | SEQ ID NOs: 54-63 | | | | |
|---|---|---|---|---|---|
| | LCVR | | LCDR1 | LCDR2 | LCDR3 |
| Humanized anti-CD20 antibody | Amino acid sequence | Nucleotide sequence | Amino acid sequence | Amino acid sequence | Amino acid sequence |
| Mab001 | 54 | 55 | 56 | 57 | 58 |
| Mab002 | 54 | 55 | 56 | 57 | 58 |
| Mab003 | 54 | 55 | 56 | 57 | 58 |
| Mab004 | 59 | 60 | 61 | 62 | 63 |
| Mab005 | 59 | 60 | 61 | 62 | 63 |
| Mab006 | 59 | 60 | 61 | 62 | 63 |
| Mab007 | 59 | 60 | 61 | 62 | 63 |

TABLE 4

Heavy chain variable region sequences of humanized anti-CD20 antibodies

| | SEQ ID NOs: 64-85 | | | | |
|---|---|---|---|---|---|
| | HCVR | | HCDR1 | HCDR2 | HCDR3 |
| Humanized anti-CD20 antibody | Amino acid sequence | Nucleotide sequence | Amino acid sequence | Amino acid sequence | Amino acid sequence |
| Mab001 | 64 | 65 | 66 | 67 | 68 |
| Mab002 | 69 | 70 | 66 | 67 | 71 |
| Mab003 | 72 | 73 | 66 | 67 | 68 |
| Mab004 | 74 | 75 | 76 | 77 | 78 |
| Mab005 | 79 | 80 | 76 | 77 | 78 |
| Mab006 | 81 | 82 | 76 | 77 | 78 |
| Mab007 | 83 | 84 | 76 | 77 | 85 |

An amino acid sequence of a Mab001 antibody light chain variable region (VK) is shown as SEQ ID NO: 54, a nucleic acid encoding the Mab001 antibody light chain variable region is shown as SEQ ID NO: 55, and CDR1, CDR2 and CDR3 of the Mab001 antibody light chain variable region are shown as SEQ ID NO: 56-58.

EIVLTQSPGTLSLSPGERATLSCRASSSVSYIHWFQQKPGQAPRPLIYA
TSNLASGIPDRFSGSGSGTDYTLTISRLEPEDFAVYYCQQWTSNPPTFG
QGTKLEIK

An amino acid sequence of the Mab001 antibody heavy chain variable region (VH) is shown as SEQ ID NO: 64, a nucleic acid encoding the Mab001 antibody heavy chain variable region is shown as SEQ ID NO: 65, and CDR1, CDR2 and CDR3 of the Mab001 antibody heavy chain variable region are shown as SEQ ID NO: 66-68.

QVQLVQSGAEVKKPGSSVKVSCKASGYTFTSYNMHWVRQAPGQGLEWMGA
IYPGNGDTSYNQKFQGRVTLTADKSSSTAYMELSSLRSEDTAVYYCARST
YYGGDWYFNVWGQGTLVTVSS

An amino acid sequence of the Mab002 antibody light chain variable region (VK) is shown as SEQ ID NO: 54, a nucleic acid encoding the Mab002 antibody light chain variable region is shown as SEQ ID NO: 55, and CDR1, CDR2 and CDR3 of the Mab002 antibody light chain variable region are shown as SEQ ID NO: 56-58.

EIVLTQSPGTLSLSPGERATLSCRASSSVSYIHWFQQKPGQAPRPLIYAT
SNLASGIPDRFSGSGSGTDYTLTISRLEPEDFAVYYCQQWTSNPPTFGQG
TKLEIK

An amino acid sequence of the Mab002 antibody heavy chain variable region (VH) is shown as SEQ ID NO: 69, a nucleic acid encoding the Mab002 antibody heavy chain variable region is shown as SEQ ID NO: 70, and CDR1, CDR2 and CDR3 of the Mab002 antibody heavy chain variable region are shown as SEQ ID NO: 66, 67 and 71.

QVQLVQSGAEVKKPGSSVKVSCKASGYTFTSYNMIIWVRQAPGQGLEWMG
AIYPGNGDTSYNQKFQGRVTLTADKSSSTAYMELSSLRSEDTAVYYCARS
TYYGGDWYFDYWGQGTLVTVSS

An amino acid sequence of the Mab003 antibody light chain variable region (VK) is shown as SEQ ID NO: 54, a nucleic acid encoding the Mab003 antibody light chain variable region is shown as SEQ ID NO: 55, and CDR1, CDR2 and CDR3 of the Mab003 antibody light chain variable region are shown as SEQ ID NO: 56-58.

EIVLTQSPGTLSLSPGERATLSCRASSSVSYIHWFQQKPGQAPRPLIYAT
SNLASGIPDRFSGSGSGTDYTLTISRLEPEDFAVYYCQQWTSNPPTFGQG
TKLEIK

An amino acid sequence of the Mab003 antibody heavy chain variable region (VH) is shown as SEQ ID NO: 72, a nucleic acid encoding the Mab003 antibody heavy chain variable region is shown as SEQ ID NO: 73, and CDR1, CDR2 and CDR3 of the Mab003 antibody heavy chain variable region are shown as SEQ ID NO: 66-68.

EVQLVESGGGLVQPGGSLRLSCAASGYTFTSYNMHWVRQAPGQGLEWMGA
IYPGNGDTSYNQKFQGRVTLTADKSSSTAYMELSSLRSEDTAVYYCARST
YYGGDWYFNVWGQGTLVTVSS

An amino acid sequence of the Mab004 antibody light chain variable region (VK) is shown as SEQ ID NO: 59, a nucleic acid encoding the Mab004 antibody light chain variable region is shown as SEQ ID NO: 60, and CDR1, CDR2 and CDR3 of the Mab004 antibody light chain variable region are shown as SEQ ID NO: 61-63.

EIVLTQSPGTLSLSPGERATLSCRASQSVSSYLAWYQQKPGQAPRLLIYD
ASNRATGIPDRFSGSGSGTDFTLTISRLEPEDFAVYYCQQRSNWPITFGQ
GTKLEIK

An amino acid sequence of the Mab004 antibody heavy chain variable region (VH) is shown as SEQ ID NO: 74, a nucleic acid encoding the Mab004 antibody heavy chain variable region is shown as SEQ ID NO: 75, and CDR1, CDR2 and CDR3 of the Mab004 antibody heavy chain variable region are shown as SEQ ID NO: 76-78.

EVQLLESGGGLVQPGGSLRLSCAASGFTFNDYAMHWVRQAPGKGLEWVST
ISWNSGSIGYADSVKGRFTISRDNAKKTLYLQMNSLRAEDTAVYYCAKDI
QYGNYYYGMDVWGQGTLVTVSS

An amino acid sequence of the Mab005 antibody light chain variable region (VK) is shown as SEQ ID NO: 59, a nucleic acid encoding the Mab005 antibody light chain variable region is shown as SEQ ID NO: 60, and CDR1, CDR2 and CDR3 of the Mab005 antibody light chain variable region are shown as SEQ ID NO: 61-63.

EIVLTQSPGTLSLSPGERATLSCRASQSVSSYLAWYQQKPGQAPRLLIYD
ASNRATGIPDRFSGSGSGTDFTLTISRLEPEDFAVYYCQQRSNWPITFGQ
GTKLEIK

An amino acid sequence of the Mab005 antibody heavy chain variable region (VH) is shown as SEQ ID NO: 79, a nucleic acid encoding the Mab005 antibody heavy chain variable region is shown as SEQ ID NO: 80, and CDR1, CDR2 and CDR3 of the Mab005 antibody heavy chain variable region are shown as SEQ ID NO: 76-78.

EVQLLESGGGLVQPGGSLRLSCAASGFTFNDYAMHWVRQAPGKGLEWVST
ISWNSGSIGYADSVKGRFTISRDNSKNTLYLQMNSLRAEDTAVYYCAKDI
QYGNYYYGMDVWGQGTLVTVSS

An amino acid sequence of the Mab006 antibody light chain variable region (VK) is shown as SEQ ID NO: 59, a nucleic acid encoding the Mab006 antibody light chain variable region is shown as SEQ ID NO: 60, and CDR1, CDR2 and CDR3 of the Mab006 antibody light chain variable region are shown as SEQ ID NO: 61-63.

EIVLTQSPGTLSLSPGERATLSCRASQSVSSYLAWYQQKPGQAPRLLIYD
ASNRATGIPDRFSGSGSGTDFTLTISRLEPEDFAVYYCQQRSNWPITFGQ
GTKLEIK

An amino acid sequence of the Mab006 antibody heavy chain variable region (VH) is shown as SEQ ID NO: 81, a nucleic acid encoding the Mab006 antibody heavy chain variable region is shown as SEQ ID NO: 82, and CDR1, CDR2 and CDR3 of the Mab006 antibody heavy chain variable region are shown as SEQ ID NO: 76-78.

EVQLLESGGGVVQPGGSLRLSCAASGFTFNDYAMHWVRQAPGKGLEWVST
ISWNSGSIGYADSVKGRFTISRDNSKNTLYLQMNSLRAEDTAVYYCAKDI
QYGNYYYGMDVWGQGTLVTVSS

An amino acid sequence of the Mab007 antibody light chain variable region (VK) is shown as SEQ ID NO: 59, a nucleic acid encoding the Mab007 antibody light chain variable region is shown as SEQ ID NO: 60, and CDR1, CDR2 and CDR3 of the Mab007 antibody light chain variable region are shown as SEQ ID NO: 61-63.

EIVLTQSPGTLSLSPGERATLSCRASQSVSSYLAWYQQKPGQAPRLLIYD
ASNRATGIPDRFSGSGSGTDFTLTISRLEPEDFAVYYCQQRSNWPITFGQ
GTKLEIK

An amino acid sequence of the Mab007 antibody heavy chain variable region (VH) is shown as SEQ ID NO: 83, a nucleic acid encoding the Mab007 antibody heavy chain variable region is shown as SEQ ID NO: 84, and CDR1, CDR2 and CDR3 of the Mab007 antibody heavy chain variable region are shown as SEQ ID NO: 76, 77 and 85.

EVQLLESGGGVVQPGGSLRLSCAASGFTFNDYAMHWVRQAPGKGLEWVST
ISWNSGSIGYADSVKGRFTISRDNSKNTLYLQMNSLRAEDTAVYYCAKDI
QYGNYYYGMDYWGQGTLVTVSS

Binding of Humanized anti-CD20 Antibody to Tumor Cells

A lymphoma cell line Raji and Daudi cells in the logarithmic growth phase were taken, 200 μg/mL mouse IgG (Jackson ImmunoResearch) was added, and the mixture was blocked for 30 min. $5\times10^4$ cells and 50 μL, of gradient-diluted antibody (the initial concentration of 200 nM, 5-fold dilution, a total of 8 gradients) were added to each well of a 96-well U-shaped plate, and incubated on ice for 45 min.

Figure 5:
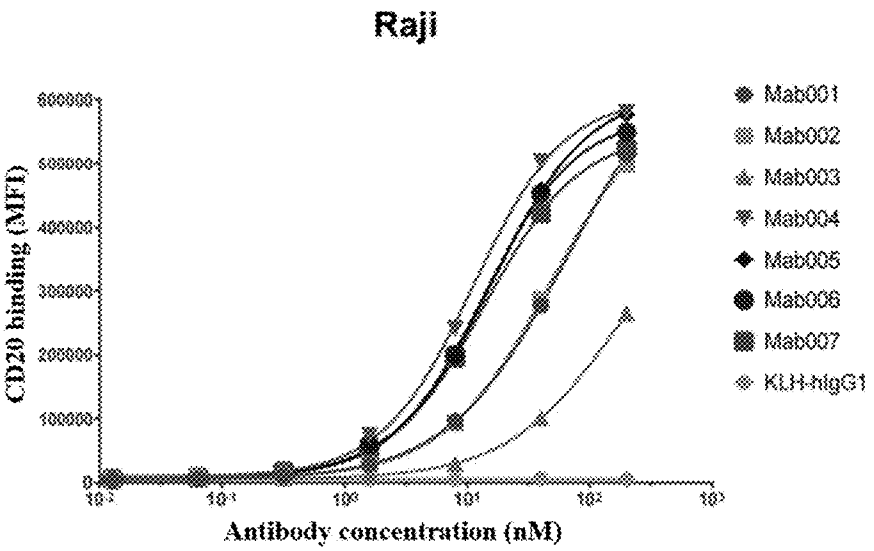
FIG. 5 shows the binding of a humanized CD20 antibody to Raji cells.
Figure 6:
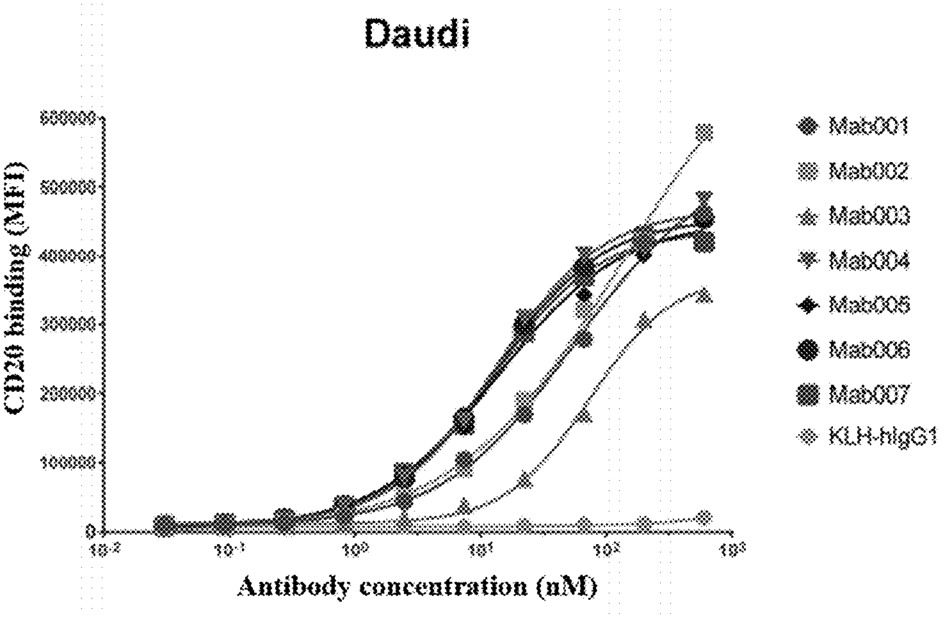
FIG. 6 shows the binding of a humanized CD20 antibody to Daudi cells.

After the cells were washed, 50 μL, of Alexa Fluro647-labelled goat anti-human IgG Fc (1: 300 dilution) was added to each well, and the mixture was incubated on ice for 45 min. 60 μL, of PI (Sigma, P4170) was added to each well, and the mixture was incubated for 5 min and detected by using a flow cytometer (iQue Screener). FIG. 5 shows that the binding of the humanized anti-CD20 antibody to Raji cells, and FIG. 6 shows the binding of the humanized anti-CD20 antibody to Daudi cells.

Example 4 Combinatorial Screening of Humanized Anti-CD20 Antibodies and Anti-CD3 Antibodies 1. Bifunctional Antibodies for Antibody Combination Screening The humanized anti-CD20 antibodies Mab002, Mab005 and Mab007 that were obtained after optimization of isoelectric point, and the humanized anti-CD3 antibody were selected to construct bispecific antibodies. Referring to Schaefer W et al. (PNAS, 2011), combinations of humanized anti-CD20 antibodies and anti-CD3 antibodies were screened: the light chain variable region of the humanized anti-CD20 antibody was cloned into a eukaryotic expression vector containing the kappa light chain constant region, the heavy chain variable region was cloned into a eukaryotic expression vector containing the mutant human IgG4 constant region, the light chain variable region of the humanized anti-CD3 antibody was cloned into a eukaryotic expression vector containing the lambda light chain constant region, the heavy chain hinge region, and the constant regions CH2 and CH3, the heavy chain variable region of the anti-CD3 antibody was cloned into a eukaryotic expression vector containing the human CH1 constant region, 4 plasmids encoding the light and heavy chain genes were mixed in a ratio of 1:1:1:1, co-transfected into HEK293E cells, and expressed for 5-6 d, and a culture supernatant was collected and purified by Protein A affinity chromatography. SEC-HPLC results show that in the bifunctional antibodies prepared by this method, i.e., Mab002×CD3, Mab005×CD3, and Mab007×CD3, the monomer content is greater than 55%, which is used for the relative activity evaluation of the following binding to target cells and killing effects.

The bifunctional antibody sequences for antibody combination screening are shown in Table 5.

TABLE 5

Bifunctional antibody sequences for antibody combination screening

| Bifunctional antibody | CD20 antibody | CD3 antibody |
|---|---|---|
| Mab002 × CD3, SEQ ID NO: 86-93, with charge variants introduced into the CD20 antigen arm and CD3 arm:<br>$V\kappa_{CD20}$: $Gln_{37}Lys$;<br>$VH_{CD20}$: $Gln_{39}Glu$;<br>$V\lambda_{CD3}$: $Gln_{40}Glu$;<br>$VH_{CD3}$: $GIN_{39}Lys$ | Chain 1: an amino acid sequence of chain 1 is shown as SEQ ID NO: 86, and a nucleic acid encoding chain 1 is shown as SEQ ID NO: 87<br>QVQLVQSGAEVKKPGSSVKVSCK<br>ASGYTFTSYNMHWVREAPGQGLE<br>WMGAIYPGNGDTSYNQKFQGRVT<br>LTADKSSSTAYMELSSLRSEDTA<br>VYYCARSTYYGGDWYFDYWGQGT<br>LVTVSSASTKGPSVFPLAPCSRS<br>TSESTAALGCLVEDYFPEPVTVS<br>WNSGALTSGVHTFPAVLQSSGLY<br>SLSSVVTVPSSSLGTKTYTCNVD<br>HKPSNTKVDERVESKYGPPCPPC<br>PAPEFEGGPSVFLFPPKPKDTLM<br>ISRTPEVTCVVVDVSQEDPEVQF<br>NWYVDGVEVHNAKTKPREEQFAS<br>TYRVVSVLTVLHQDWLNGKEYKC<br>KVSNKGLPSSIEKTISKAKGQPR<br>EPQVCTLPPSQEEMTKNQVSLSC<br>AVKGFYPSDIAVEWESNGQPENN<br>YKTTPPVLDSDGSFFLVSKLTVD<br>KSRWQEGNVFSCSVMHEALHNHY<br>TQKSLSLSLGK* | Chain 3: an amino acid sequence of chain 3 is shown as SEQ ID NO: 90, and a nucleic acid encoding chain 3 is shown as SEQ ID NO: 91<br>QAVVTQEPSLTVSPGGTVTLTCRS<br>STGAVTTSNYANWVQEKPGQAPRG<br>LIGGTNKRAPWTPARFSGSLLGGK<br>AALTITGAQAEDEAEYYCVLWYSN<br>LWVFGGGTKLTVLGQPKAAPSVTL<br>FPPSSEELQANKATLVCLISDFYP<br>GAVTVAWKADSSPVKAGVETTTPS<br>KQSNNKYAASSYLSLTPEQWKSHR<br>SYSCQVTHEGSTVEKTVAPTECSE<br>SKYGPPCPPCPAPEFEGGPSVFLF<br>PPKPKDTLMISRTPEVTCVVVDVS<br>QEDPEVQFNWYVDGVEVHNAKTKP<br>REEQFASTYRVVSVLTVLHQDWLN<br>GKEYKCKVSNKGLPSSIEKTISKA<br>KGQPREPQVYTLPPCQEEMTKNQV<br>SLWCLVKGFYPSDIAVEWESNGQP<br>ENNYKTTPPVLDSDGSFFLYSKLT<br>VDKSRWQEGNVFSCSVMHEALHNH<br>YTQKSLSLSLGK* |
| | Chain 2: an amino acid sequence of chain 2 is shown as SEQ ID NO: 88, and a nucleic acid encoding chain 2 is shown as SEQ ID NO: 89<br>EIVLTQSPGTLSLSPGERATLSC<br>RASSSVSYIHWFQKKPGQAPRPL<br>IYATSNLASGIPDRFSGSGSGTD<br>YTLTISRLEPEDFAVYYCQQWTS<br>NPPTFGQGTKLEIKRTVAAPSVF<br>IFPPSDKKLKSGTASVVCLLNNF<br>YPREAKVQWKVDNALQSGNSQES<br>VTEQDSKDSTYSLSSTLTLSKAD<br>YEKHKVYACEVTHQGLSSPVTKS<br>FNRGEC* | Chain 4: an amino acid sequence of chain 4 is shown as SEQ ID NO: 92, and a nucleic acid encoding chain 4 is shown as SEQ ID NO: 93<br>EVQLVESGGGLVQPGGSLRLSCAA<br>SGFTFNTYAMNWVRKAPGKGLEWV<br>GRIRSKYNNYATYYADSVKDRFTI<br>SRDDSKNSLYLQMNSLKTEDTAVY<br>YCVRHGNFGNSYVSWFAYWGQGTL<br>VTVSSASTKGPSVFPLAPCSRSTS<br>ESTAALGCLVKDYFPEPVTVSWNS<br>GALTSGVHTFPAVLQSSGLYSLSS<br>VVTVPSSSLGTKTYTCNVDHKPSN<br>TKVDKRV* |
| Mab005 × CD3, SEQ ID NO: 90-97, with charge variants introduced into the | Chain 1: an amino acid sequence of chain 1 is shown as SEQ ID NO: 94, and a nucleic acid | Chain 3: an amino acid sequence of chain 3 is shown as SEQ ID NO: 90, and a nucleic acid |

TABLE 5-continued

Bifunctional antibody sequences for antibody combination screening

| Bifunctional antibody | CD20 antibody | CD3 antibody |
|---|---|---|
| CD20 antigen arm and CD3 arm:<br>V$\kappa_{CD20}$: Gln$_{37}$Lys;<br>VH$_{CD20}$: Gln$_{39}$Glu;<br>V$\lambda_{CD3}$: Gln$_{40}$Glu;<br>VH$_{CD3}$: Gln$_{39}$Lys | encoding chain 1 is shown as SEQ ID NO: 95<br>EVQLLESGGGLVQPGGSLRLSCA<br>ASGFTFNDYAMHWVREAPGKGLE<br>WVSTISWNSGSIGYADSVKGRFT<br>ISRDNSKNTLYLQMNSLRAEDTA<br>VYYCAKDIQYGNYYYGMDVWGQG<br>TLVTVSSASTKGPSVFPLAPCSR<br>STSESTAALGCLVEDYFPEPVTV<br>SWNSGALTSGVHTFPAVLQSSGL<br>YSLSSVVTVPSSSLGTKTYTCNV<br>DHKPSNTKVDERVESKYGPPCPP<br>CPAPEFEGGPSVFLFPPKPKDTL<br>MISRTPEVTCVVVDVSQEDPEVQ<br>FNWYVDGVEVHNAKTKPREEQFA<br>STYRVVSVLTVLHQDWLNGKEYK<br>CKVSNKGLPSSIEKTISKAKGQP<br>REPQVCTLPPSQEEMTKNQVSLS<br>CAVKGFYPSDIAVEWESNGQPEN<br>NYKTTPPVLDSDGSFFLVSKLTV<br>DKSRWQEGNVFSCSVMHEALHNH<br>YTQKSLSLSLGK* | encoding chain 3 is shown as SEQ ID NO: 91<br>QAVVTQEPSLTVSPGGTVTLTCRS<br>STGAVTTSNYANWVQEKPGQAPRG<br>LIGGTNKRAPWTPARFSGSLLGGK<br>AALTITGAQAEDEAEYYCVLWYSN<br>LWVFGGGTKLTVLGQPKAAPSVTL<br>FPPSSEELQANKATLVCLISDFYP<br>GAVTVAWKADSSPVKAGVETTTPS<br>KQSNNKYAASSYLSLTPEQWKSHR<br>SYSCQVTHEGSTVEKTVAPTECSE<br>SKYGPPCPPCPAPEFEGGPSVFLF<br>PPKPKDTLMISRTPEVTCVVVDVS<br>QEDPEVQFNWYVDGVEVHNAKTKP<br>REEQFASTYRVVSVLTVLHQDWLN<br>GKEYKCKVSNKGLPSSIEKTISKA<br>KGQPREPQVYTLPPCQEEMTKNQV<br>SLWCLVKGFYPSDIAVEWESNGQP<br>ENNYKTTPPVLDSDGSFFLYSKLT<br>VDKSRWQEGNVFSCSVMHEALHNH<br>YTQKSLSLSLGK* |
| | Chain 2: an amino acid sequence of chain 2 is shown as SEQ ID NO: 96, and a nucleic acid encoding chain 2 is shown as SEQ ID NO: 97<br>EIVLTQSPGTLSLSPGERATLSC<br>RASQSVSSYLAWYQKKPGQAPRL<br>LIYDASNRATGIPDRFSGSGSGT<br>DFTLTISRLEPEDFAVYYCQQRS<br>NWPITFGQGTKLEIKRTVAAPSV<br>FIFPPSDKKLKSGTASVVCLLNN<br>FYPREAKVQWKVDNALQSGNSQE<br>SVTEQDSKDSTYSLSSTLTLSKA<br>DYEKHKVYACEVTHQGLSSPVTK<br>SFNRGEC* | Chain 4: an amino acid sequence of chain 4 is shown as SEQ ID NO: 92, and a nucleic acid encoding chain 4 is shown as SEQ ID NO: 93<br>EVQLVESGGGLVQPGGSLRLSCAA<br>SGFTFNTYAMNWVRKAPGKGLEWV<br>GRIRSKYNNYATYYADSVKDRFTI<br>SRDDSKNSLYLQMNSLKTEDTAVY<br>YCVRHGNFGNSYVSWFAYWGQGTL<br>VTVSSASTKGPSVFPLAPCSRSTS<br>ESTAALGCLVKDYFPEPVTVSWNS<br>GALTSGVHTFPAVLQSSGLYSLSS<br>VVTVPSSSLGTKTYTCNVDHKPSN<br>TKVDKRV* |
| Mab007 × CD3, SEQ ID NO: 98-101 and 90-93, with charge variants introduced into the CD20 antigen arm and CD3 arm:<br>V$\kappa_{CD20}$: Gln$_{38}$Lys;<br>VH$_{CD20}$: Gln$_{39}$Glu;<br>V$\lambda_{CD3}$: Gln$_{40}$Glu;<br>VH$_{CD3}$: Gln$_{39}$Lys | Chain 1: an amino acid sequence of chain 1 is shown as SEQ ID NO: 98, and a nucleic acid encoding chain 1 is shown as SEQ ID NO: 99<br>EVQLLESGGGVVQPGGSLRLSCA<br>ASGFTFNDYAMHWVREAPGKGLE<br>WVSTISWNSGSIGYADSVKGRFT<br>ISRDNSKNTLYLQMNSLRAEDTA<br>VYYCAKDIQYGNYYYGMDYWGQG<br>TLVTVSSASTKGPSVFPLAPCSR<br>STSESTAALGCLVEDYFPEPVTV<br>SWNSGALTSGVHTFPAVLQSSGL<br>YSLSSVVTVPSSSLGTKTYTCNV<br>DHKPSNTKVDERVESKYGPPCPP<br>CPAPEFEGGPSVFLFPPKPKDTL<br>MISRTPEVTCVVVDVSQEDPEVQ<br>FNWYVDGVEVHNAKTKPREEQFA<br>STYRVVSVLTVLHQDWLNGKEYK<br>CKVSNKGLPSSIEKTISKAKGQP<br>REPQVCTLPPSQEEMTKNQVSLS<br>CAVKGFYPSDIAVEWESNGQPEN<br>NYKTTPPVLDSDGSFFLVSKLTV<br>DKSRWQEGNVFSCSVMHEALHNH<br>YTQKSLSLSLGK* | Chain 3: an amino acid sequence of chain 3 is shown as SEQ ID NO: 90, and a nucleic acid encoding chain 3 is shown as SEQ ID NO: 91<br>QAVVTQEPSLTVSPGGTVTLTCRS<br>STGAVTTSNYANWVQEKPGQAPRG<br>LIGGTNKRAPWTPARFSGSLLGGK<br>AALTITGAQAEDEAEYYCVLWYSN<br>LWVFGGGTKLTVLGQPKAAPSVTL<br>FPPSSEELQANKATLVCLISDFYP<br>GAVTVAWKADSSPVKAGVETTTPS<br>KQSNNKYAASSYLSLTPEQWKSHR<br>SYSCQVTHEGSTVEKTVAPTECSE<br>SKYGPPCPPCPAPEFEGGPSVFLF<br>PPKPKDTLMISRTPEVTCVVVDVS<br>QEDPEVQFNWYVDGVEVHNAKTKP<br>REEQFASTYRVVSVLTVLHQDWLN<br>GKEYKCKVSNKGLPSSIEKTISKA<br>KGQPREPQVYTLPPCQEEMTKNQV<br>SLWCLVKGFYPSDIAVEWESNGQP<br>ENNYKTTPPVLDSDGSFFLYSKLT<br>VDKSRWQEGNVFSCSVMHEALHNH<br>YTQKSLSLSLGK* |
| | Chain 2: an amino acid sequence of chain 2 is shown as SEQ ID NO: 100, and a nucleic acid encoding chain 2 is shown as SEQ ID NO: 101<br>EIVLTQSPGTLSLSPGERATLSC<br>RASQSVSSYLAWYQKKPGQAPRL<br>LIYDASNRATGIPDRFSGSGSGT | Chain 4: an amino acid sequence of chain 4 is shown as SEQ ID NO: 92, and a nucleic acid encoding chain 4 is shown as SEQ ID NO: 93<br>EVQLVESGGGLVQPGGSLRLSCAA<br>SGFTFNTYAMNWVRKAPGKGLEWV<br>GRIRSKYNNYATYYADSVKDRFTI |

TABLE 5-continued

| Bifunctional antibody sequences for antibody combination screening | | |
|---|---|---|
| Bifunctional antibody | CD20 antibody | CD3 antibody |
| | DFTLTISRLEPEDFAVYYCQQRS | SRDDSKNSLYLQMNSLKTEDTAVY |
| | NWPITFGQGTKLEIKRTVAAPSV | YCVRHGNFGNSYVSWFAYWGQGTL |
| | FIFPPSDKKLKSGTASVVCLLNN | VTVSSASTKGPSVFPLAPCSRSTS |
| | FYPREAKVQWKVDNALQSGNSQE | SETAALGCLVKDYFPEPVTVSWNS |
| | SVTEQDSKDSTYSLSSTLTLSKA | GALTSGVHTFPAVLQSSGLYSLSS |
| | DYEKHKVYACEVTHQGLSSPVTK | VVTVPSSSLGTKTYTCNVDHKPSN |
| | SFNRGEC* | TKVDKRV* |

2. Recognition of CD20+ Cells and Jurkat cells

Raji cells and human peripheral blood leukemia T cell line Jurkat cells in the logarithmic growth phase were taken, 200 μg/mL mouse IgG was added, and the mixture was blocked for 30 min. $5\times10^4$ cells and 50 μL of gradient-diluted antibody (the initial concentration of 1800 nM, 5-fold dilution, a total of 8 gradients) were added to each well of a 96-well U-shaped plate, and incubated on ice for 45 min. After the primary antibody was washed away, 50 μL of Alexa Fluro647-labelled goat anti-human IgG Fc (1:300 dilution) was added to each well, the mixture was incubated on ice for 45 min, 60 μL of PI was added to each well, and the mixture was incubated for 5 min and detected by using a flow cytometer.

Figure 7:
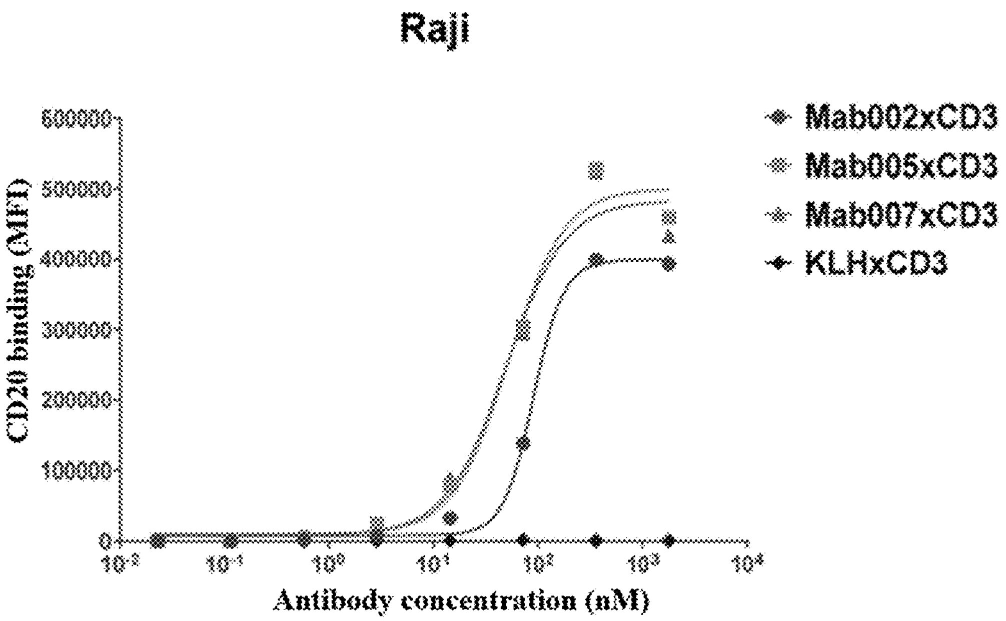
FIG. 7 shows the binding of a CD20×CD3 antibody combination to Raji cells.
Figure 8:
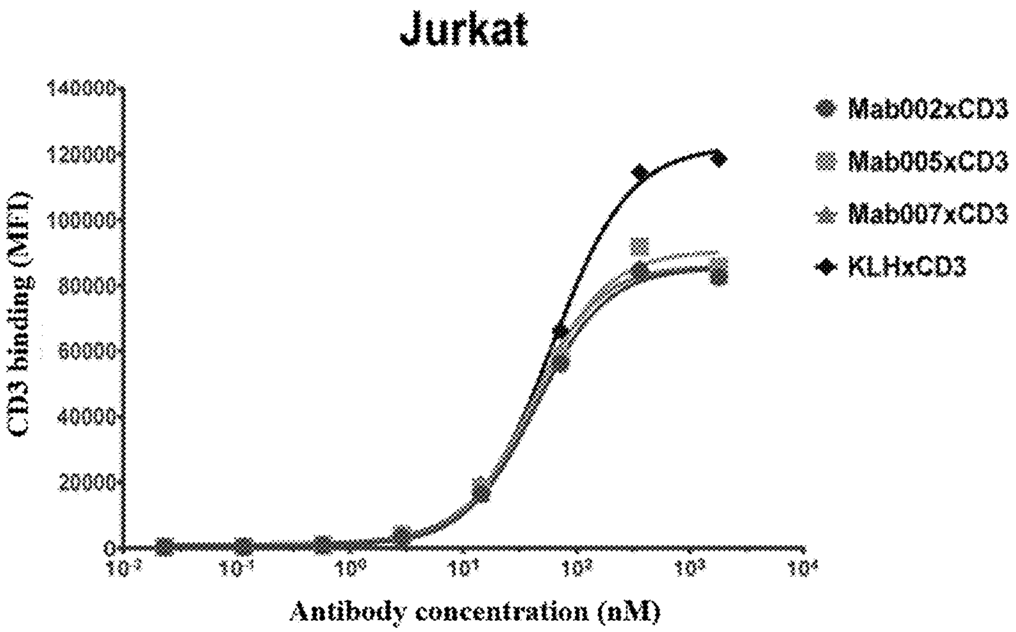
FIG. 8 shows the binding of a CD20×CD3 antibody combination to Jurkat cells.

FIG. 7 shows the binding of the anti-CD20×CD3 antibody combination to Raji cells, and FIG. 8 shows the binding of the anti-CD20×CD3 antibody combination to Jurkat cells.

3. T-Cell Dependent Cellular Cytotoxicity (TDCC) Assay

Freshly separated PBMCs were mixed with Raji cells in the logarithmic growth phase (effector/target cells=10:1), 50 μL of gradient-diluted antibody (the initial concentration of 66.7 nM, 10-fold dilution, 8 gradients) was added to each well, and the mixture was incubated at 37° C. under 5% $CO_2$ for 24 h. After culture was completed, the mixture was centrifuged at 1000 rpm for 3 min, a supernatant was collected for LDH release assay, 50 μL of supernatant was transferred to a black ELISA plate, 50 μL of LDH detection substrate was added to each well, the reaction was terminated after 10 min, LDH was detected (Biotek Synergy HT), a kill rate was calculated according to the following formula. After the supernatant was discarded, the remaining cells in the wells were washed twice with 4% calf serum, 100 μg/mL human IgG was added, the mixture was blocked for 10 min, the T cell early activation marker CD69 and late marker CD25 detection antibodies (CD25-PE, CD4-APC, CD69-FITC, and CD8-APC) were added, and the mixture was incubated on ice for 20 min. After incubation was completed, 200 μL of 4% calf serum was added to each well for washing 3 times, a supernatant was discarded, 60 μL of PI (1:200 dilution) was added to each well, the mixture was incubated on ice for 5 min and detected by using a flow cytometer (BD FACS celesta).

The formula for calculating a kill rate is as follows:

$$\text{kill rate }(\%) = \frac{\text{experimental well} - \text{target cell spontaneous death}}{\text{target cell maximum release} - \text{target cell spontaneous death}} \times 100\%$$

Figure 9:
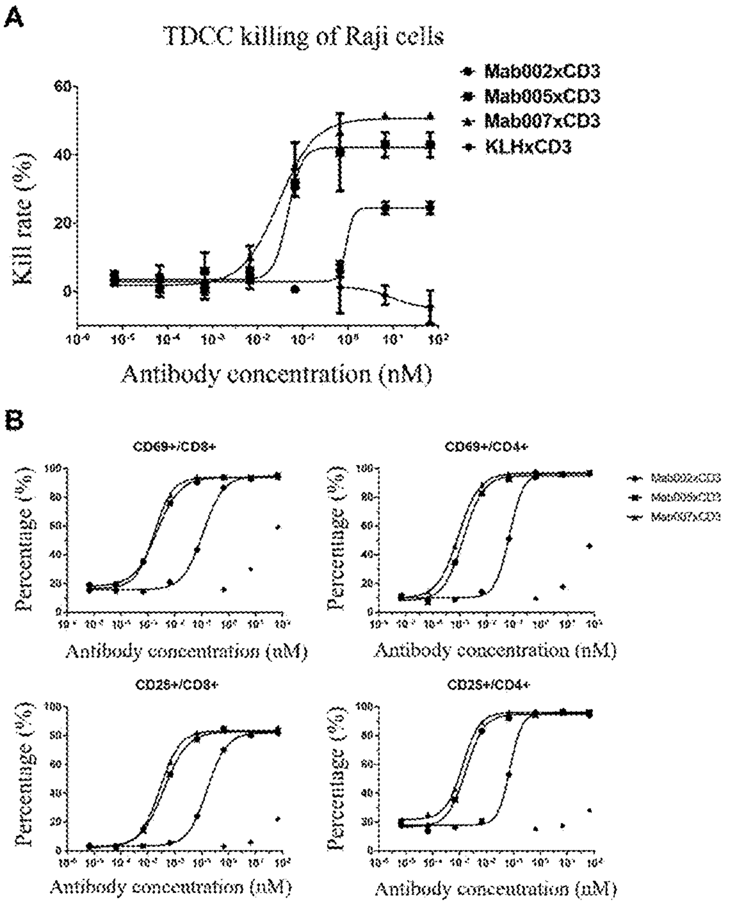

FIG. 9A shows TDCC killing effects mediated by different anti-CD20×CD3 antibody combinations on Raji cells; and FIG. 9B shows during TDCC killing, the anti-CD20×CD3 antibody combinations can stimulate T cells to upregulate the activation markers CD69 and CD25.

4. Activation of T Cell Signaling Pathways

A luciferase reporter plasmid pGL4.30[luc2P/NFAT-RE/Hygro] (Promega, E8481) was transfected into Jurkat cells, 200 μg/mL hygromycin B was added for screening, and thus, Jurkat-NFAT luc stably transfected reporter cells were obtained. CD20+ target cells, the anti-CD20×CD3 antibody, and the Jurkat-NFAT-luc reporter cells were co-incubated, after the anti-CD20×CD3 antibody bound to the target cells, the other end of the anti-CD20×CD3 antibody bound to the CD3 receptor on the surface of Jurkat cells to cause the accumulation of CD3 intracellular signaling motifs, and an activation signal was transmitted to the nucleus through the NFAT pathway, which eventually leaded to the upregulation of the expression of the reporter gene luciferase. Jurkat-NFAT-luc reporter cells and Raji cells in the logarithmic growth phase were respectively taken, and centrifuged at 1000 rpm for 10 min, a supernatant was discarded, and the cells were resuspended to a concentration of 2×106 cells/mL. 50 μL of Raji cell suspension was added to each well of a 96-well plate and centrifuged at 300 g for 5 min, a supernatant was discarded, 50 μL of Jurkat-NFAT-luc cell suspension and 50 μL of gradient-diluted antibody (the initial concentration of 20 μg/mL, 10-fold dilution, 10 gradients) were added to each well, and the mixture was cultured at 37° C. under 5% $CO_2$ for 6 h. After culture was completed, referring to the manual of ONE-Glo Luciferase Assay System (Promega), 100 μL of detection reagent was added to each well, the mixture was placed at room temperature for 3 min, and fluorescence signals were detected (Biotek Synergy HT).

Figure 10:
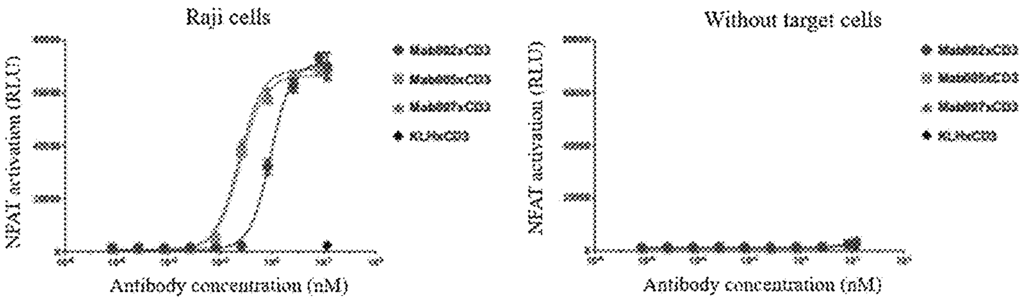
FIG. 10 shows the specific activation of NFAT pathway by different CD20×CD3 antibody combinations.

FIG. 10 shows that during co-culture with Raji cells, each anti-CD20×CD3 antibody can activate the NFAT signaling pathway of Jurkat cells, and in a case without target cells, the anti-CD20×CD3 antibodies do not activate the NFAT signaling pathway of Jurkat cells.

Example 5 Construction of CD20×CD3 κλ Bispecific Antibodies formed by Different Types of Light Chains A humanized CD3 arm ( λ light chain and paired heavy chain) and a humanized CD20 antigen arm (κ light chain and paired heavy chain) were used to construct a novel CD20×CD3 κλ bispecific antibody with the natural IgG configuration. In the case of free combination, the κ light chain or λ light chain usually tends to pair with a homologous heavy chain. Therefore, CD20×CD3 κλ001 was constructed to retain the natural sequences of the CD3 arm and the CD20 antigen arm. Meanwhile, in order to further reduce possible mismatches, based on pairing of the κ and λ light chains with the homologous heavy chains, charge variants (Tan et al., 1998) for stabilizing Fv were introduced, or complementary charge pairs $Glu_{123}Lys/Gln_{24}Lys$ and $Lys_{152}Glu/Lys_{218}Glu$ were introduced between $C_H1$/Cκ, the following 5 CD20×CD3 κλ bispecific antibodies were designed and constructed:

(1) CD20×CD3 κλ001 retaining the natural sequences of the CD3 arm and the CD20 antigen arm;

(2) CD20×CD3 κλ002 with charge variants introduced into both the CD20 antigen arm and the CD3 arm ($Vκ_{CD20}$: $Gln_{38}Lys$; $VH_{CD20}$: $Gln_{39}Glu$; $Gln_{40}Glu$; $VH_{CD3}$: $Gln_{39}Lys$);

(3) CD20×CD3 κλ003 with complementary charge pairs added between CH1/Cκ on the basis of CD20×CD3 κλ002 ($Vκ\text{-}Ck_{CD20}$: $Gln_{38}Lys\backslash Glu_{123}Lys\backslash Glu_{124}Lys$; $V_H\text{-}C_H1_{CD20}$: $Gln_{39}Glu\backslash Lys_{152}Glu\backslash Lys_{218}Glu$; $Vλ_{CD3}$: $Gln_{40}Glu$; $VH_{CD3}$: $Gln_{39}Lys$);

(4) CD20×CD3 κλ004 with charge variants for stabilizing Fv introduced into the CD20 antigen arm ($Vκ_{CD20}$: $Gln_{38}Lys$; $VH_{CD20}$: $Gln_{39}Glu$); and (5) CD20×CD3 κλ005 with charge variants introduced into the CD3 arm ($Vλ_{CD3}$: $Gln_{40}Glu$; $VH_{CD3}$: $Gln_{39}Lys$).

Figure 11:
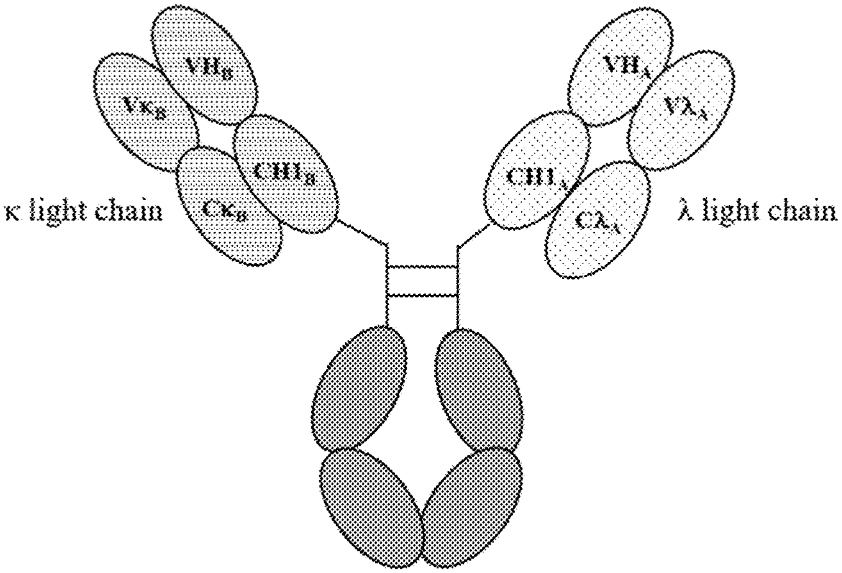
FIG. 11 shows a CD20×CD3 κλ bispecific antibody of the present disclosure.

The Fc portion of the CD20×CD3 κλ bispecific antibody adopted the human IgG4 knob-into-hole structure to achieve heterodimer pairing (Atwell et al., 1997), and the hinge region was kept stable and interaction with Fcγ receptors and Clq was weakened by mutations of $Ser_{228}Pro$, $Leu_{235}Glu$ and $Pro_{329}Ala$. FIG. 11 shows the novel CD20×CD3 κλ bispecific antibodies.

Sequences of the CD20×CD3 κλ bispecific antibodies are shown in Table 6.

TABLE 6

Sequences of CD20 × CD3 κλ bispecific antibodies

| CD20 arm | CD3 arm |
|---|---|
| CD20 × CD3 κλ001 (SEQ ID NO: 102-109): | |
| κ light chain: an amino acid sequence of the κ light chain is shown as SEQ ID NO: 102, and a nucleic acid encoding the κ light chain is shown as SEQ ID NO: 103<br>EIVLTQSPGTLSLSPGERATLSCRASQS<br>VSSYLAWYQQKPGQAPRLLIYDASNRAT<br>GIPDRFSGSGSGTDFTLTISRLEPEDFA<br>VYYCQQRSNWPITFGQGTKLEIKRTVAA<br>PSVFIFPPSDEQLKSGTASVVCLLNNFY<br>PREAKVQWKVDNALQSGNSQESVTEQDS<br>KDSTYSLSSTLTLSKADYEKHKVYACEV<br>THQGLSSPVTKSFNRGEC* | λ light chain: an amino acid sequence of the λ light chain is shown as SEQ ID NO: 106, and a nucleic acid encoding the λ light chain is shown as SEQ ID NO: 107<br>QAVVTQEPSLTVSPGGTVTLTCRSSTGA<br>VTTSNYANWVQQKPGQAPRGLIGGTNKR<br>APWTPARFSGSLLGGKAALTITGAQAED<br>EAEYYCVLWYSNLWVFGGGTKLTVLGQP<br>KAAPSVTLFPPSSEELQANKATLVCLIS<br>DFYPGAVTVAWKADSSPVKAGVETTTPS<br>KQSNNKYAASSYLSLTPEQWKSHRSYSC<br>QVTHEGSTVEKTVAPTECS* |
| Heavy chain 1: an amino acid sequence of heavy chain 1 is shown as SEQ ID NO: 104, and a nucleic acid encoding heavy chain 1 is shown as SEQ ID NO: 105<br>EVQLLESGGGVVQPGGSLRLSCAASGFT<br>FNDYAMHWVRQAPGKGLEWVSTISWNSG<br>SIGYADSVKGRFTISRDNSKNTLYLQMN<br>SLRAEDTAVYYCAKDIQYGNYYYGMDYW<br>GQGTLVTVSSASTKGPSVFPLAPCSRST<br>SESTAALGCLVKDYFPEPVTVSWNSGAL<br>TSGVHTFPAVLQSSGLYSLSSVVTVPSS<br>SLGTKTYTCNVDHKPSNTKVDKRVESKY<br>GPPCPPCPAPEFEGGPSVFLFPPKPKDT<br>LMISRTPEVTCVVVDVSQEDPEVQFNWY<br>VDGVEVHNAKTKPREEQFNSTYRVVSVL<br>TVLHQDWLNGKEYKCKVSNKGLASSIEK<br>TISKAKGQPREPQVCTLPPSQEEMTKNQ<br>VSLSCAVKGFYPSDIAVEWESNGQPENN<br>YKTTPPVLDSDGSFFLVSKLTVDKSRWQ<br>EGNVFSCSVMHEALHNHYTQKSLSLSLG<br>K | Heavy chain 2: an amino acid sequence of heavy chain 2 is shown as SEQ ID NO: 108, and a nucleic acid encoding heavy chain 2 is shown as SEQ ID NO: 109<br>EVQLVESGGGLVQPGGSLRLSCAASGFT<br>FNTYAMNWVRQAPGKGLEWVGRIRSKYN<br>NYATYYADSVKDRFTISRDDSKNSLYLQ<br>MNSLKTEDTAVYYCVRHGNFGNSYVSWF<br>AYWGQGTLVTVSSASTKGPSVFPLAPCS<br>RSTSESTAALGCLVKDYFPEPVTVSWNS<br>GALTSGVHTFPAVLQSSGLYSLSSVVTV<br>PSSSLGTKTYTCNVDHKPSNTKVDKRVE<br>SKYGPPCPPCPAPEFEGGPSVFLFPPKP<br>KDTLMISRTPEVTCVVVDVSQEDPEVQF<br>NWYVDGVEVHNAKTKPREEQFNSTYRVV<br>SVLTVLHQDWLNGKEYKCKVSNKGLASS<br>IEKTISKAKGQPREPQVYTLPPCQEEMT<br>KNQVSLWCLVKGFYPSDIAVEWESNGQP<br>ENNYKTTPPVLDSDGSFFLYSKLTVDKS<br>RWQEGNVFSCSVMHEALHNHYTQKSLSL<br>SLGK* |
| CD20 × CD3 κλ002 (SEQ ID NO: 110-117): $Vκ_{CD20}$: $Gln_{38}Lys$; $VH_{CD20}$: $Gln_{39}Glu$; $Vλ_{CD3}$: $Gln_{40}Glu$; $VH_{CD3}$: $Gln_{39}Lys$ | |
| κ light chain: an amino acid sequence of the κ light chain is shown as SEQ ID NO: 110, and a nucleic acid encoding the κ light chain is shown as SEQ ID NO: 111<br>EIVLTQSPGTLSLSPGERATLSCRASQS<br>VSSYLAWYQKKPGQAPRLLIYDASNRAT<br>GIPDRFSGSGSGTDFTLTISRLEPEDFA<br>VYYCQQRSNWPITFGQGTKLEIKRTVAA<br>PSVFIFPPSDEQLKSGTASVVCLLNNFY | λ light chain: an amino acid sequence of the λ light chain is shown as SEQ ID NO: 114, and a nucleic acid encoding the λ light chain is shown as SEQ ID NO: 115<br>QAVVTQEPSLTVSPGGTVTLTCRSSTGA<br>VTTSNYANWVQEKPGQAPRGLIGGTNKR<br>APWTPARFSGSLLGGKAALTITGAQAED<br>EAEYYCVLWYSNLWVFGGGTKLTVLGQP<br>KAAPSVTLFPPSSEELQANKATLVCLIS |

TABLE 6-continued

Sequences of CD20 × CD3 κλ bispecific antibodies

| CD20 arm | CD3 arm |
|---|---|
| PREAKVQWKVDNALQSGNSQESVTEQDS KDSTYSLSSTLTLSKADYEKHKVYACEV THQGLSSPVTKSFNRGEC* | DFYPGAVTVAWKADSSPVKAGVETTTPS KQSNNKYAASSYLSLTPEQWKSHRSYSC QVTHEGSTVEKTVAPTECS* |
| Heavy chain 1: an amino acid sequence of heavy chain 1 is shown as SEQ ID NO: 112, and a nucleic acid encoding heavy chain 1 is shown as SEQ ID NO: 113 EVQLLESGGGVVQPGGSLRLSCAASGFT FNDYAMHWVREAPGKGLEWVSTISWNSG SIGYADSVKGRFTISRDNSKNTLYLQMN SLRAEDTAVYYCAKDIQYGNYYYGMDYW GQGTLVTVSSASTKGPSVFPLAPCSRST SESTAALGCLVKDYFPEPVTVSWNSGAL TSGVHTFPAVLQSSGLYSLSSVVTVPSS SLGTKTYTCNVDHKPSNTKVDKRVESKY GPPCPPCPAPEFEGGPSVFLFPPKPKDT LMISRTPEVTCVVVDVSQEDPEVQFNWY VDGVEVHNAKTKPREEQFNSTYRVVSVL TVLHQDWLNGKEYKCKVSNKGLASSIEK TISKAKGQPREPQVCTLPPSQEEMTKNQ VSLSCAVKGFYPSDIAVEWESNGQPENN YKTTPPVLDSDGSFFLVSKLTVDKSRWQ EGNVFSCSVMHEALHNHYTQKSLSLSLG K* | Heavy chain 2: an amino acid sequence of heavy chain 2 is shown as SEQ ID NO: 116, and a nucleic acid encoding heavy chain 2 is shown as SEQ ID NO: 117 EVQLVESGGGLVQPGGSLRLSCAASGFT FNTYAMNWVRKAPGKGLEWVGRIRSKYN NYATYYADSVKDRFTISRDDSKNSLYLQ MNSLKTEDTAVYYCVRHGNFGNSYVSWF AYWGQGTLVTVSSASTKGPSVFPLAPCS RSTSESTAALGCLVKDYFPEPVTVSWNS GALTSGVHTFPAVLQSSGLYSLSSVVTV PSSSLGTKTYTCNVDHKPSNTKVDKRVE SKYGPPCPPCPAPEFEGGPSVFLFPPKP KDTLMISRTPEVTCVVVDVSQEDPEVQF NWYVDGVEVHNAKTKPREEQFNSTYRVV SVLTVLHQDWLNGKEYKCKVSNKGLASS IEKTISKAKGQPREPQVYTLPPCQEEMT KNQVSLWCLVKGFYPSDIAVEWESNGQP ENNYKTTPPVLDSDGSFFLYSKLTVDKS RWQEGNVFSCSVMHEALHNHYT |
| CD20 × CD3 κλ003 (SEQ ID NO: 114-121): Vκ-Ck$_{CD20}$: Gln$_{38}$Lys\Glu$_{123}$Lys\Gln$_{124}$Lys; V$_H$-C$_H$1$_{CD20}$: Gln$_{39}$Glu\Lys$_{152}$Glu\Lys$_{218}$Glu; Vλ$_{CD3}$: Gln$_{40}$Glu; VH$_{CD3}$: Gln$_{39}$Lys | |
| κ light chain: an amino acid sequence of the κ light chain is shown as SEQ ID NO: 118, and a nucleic acid encoding the κ light chain is shown as SEQ ID NO: 119 EIVLTQSPGTLSLSPGERATLSCRASQS VSSYLAWYQKKPGQAPRLLIYDASNRAT GIPDRFSGSGSGTDFTLTISRLEPEDFA VYYCQQRSNWPITFGQGTKLEIKRTVAA PSVFIFPPSDKKLKSGTASVVCLLNNFY VPREAKQWKVDNALQSGNSQESVTEQDS KDSTYSLSSTLTLSKADYEKHKVYACEV THQGLSSPVTKSFNRGEC* | λ light chain: an amino acid sequence of the λ light chain is shown as SEQ ID NO: 114, and a nucleic acid encoding the λ light chain is shown as SEQ ID NO: 115 QAVVTQEPSLTVSPGGTVTLTCRSSTGA VTTSNYANWVQEKPGQAPRGLIGGTNKR APWTPARFSGSLLGGKAALTITGAQAED EAEYYCVLWYSNLWVFGGGTKLTVLGQP KAAPSVTLFPPSSEELQANKATLVCLIS DFYPGAVTVAWKADSSPVKAGVETTTPS KQSNNKYAASSYLSLTPEQWKSHRSYSC QVTHEGSTVEKTVAPTECS* |
| Heavy chain 1: an amino acid sequence of heavy chain 1 is shown as SEQ ID NO: 120, and a nucleic acid encoding heavy chain 1 is shown as SEQ ID NO: 121 EVQLLESGGGVVQPGGSLRLSCAASGFT FNDYAMHWVREAPGKGLEWVSTISWNSG SIGYADSVKGRFTISRDNSKNTLYLQMN SLRAEDTAVYYCAKDIQYGNYYYGMDYW GQGTLVTVSSASTKGPSVFPLAPCSRST SESTAALGCLVEDYFPEPVTVSWNSGAL TSGVHTFPAVLQSSGLYSLSSVVTVPSS SLGTKTYTCNVDHKPSNTKVDERVESKY GPPCPPCPAPEFEGGPSVFLFPPKPKDT LMISRTPEVTCVVVDVSQEDPEVQFNWY VDGVEVHNAKTKPREEQFNSTYRVVSVL TVLHQDWLNGKEYKCKVSNKGLASSIEK TISKAKGQPREPQVCTLPPSQEEMTKNQ VSLSCAVKGFYPSDIAVEWESNGQPENN YKTTPPVLDSDGSFFLVSKLTVDKSRWQ EGNVFSCSVMHEALHNHYTQKSLSL | Heavy chain 2: an amino acid sequence of heavy chain 2 is shown as SEQ ID NO: 116, and a nucleic acid of heavy chain 2 is shown as SEQ ID NO: 117 EVQLVESGGGLVQPGGSLRLSCAASGFT FNTYAMNWVRKAPGKGLEWVGRIRSKYN NYATYYADSVKDRFTISRDDSKNSLYLQ MNSLKTEDTAVYYCVRHGNFGNSYVSWF AYWGQGTLVTVSSASTKGPSVFPLAPCS RSTSESTAALGCLVKDYFPEPVTVSWNS GALTSGVHTFPAVLQSSGLYSLSSVVTV PSSSLGTKTYTCNVDHKPSNTKVDKRVE SKYGPPCPPCPAPEFEGGPSVFLFPPKP KDTLMISRTPEVTCVVVDVSQEDPEVQF NWYVDGVEVHNAKTKPREEQFNSTYRVV SVLTVLHQDWLNGKEYKCKVSNKGLASS IEKTISKAKGQPREPQVYTLPPCQEEMT KNQVSLWCLVKGFYPSDIAVEWESNGQP ENNYKTTPPVLDSDGSFFLYSKLTVDKS RWQEGNVFSCSVMHEALHNHYTQKSLSL |
| CD20 × CD3 κλ004 (SEQ ID NO: 106-113): Vκ$_{CD20}$: Gln$_{38}$Lys; VH$_{CD20}$: Gln$_{39}$Glu | |
| κ light chain: an amino acid sequence of the κ light chain is shown as SEQ ID NO: | λ light chain: an amino acid sequence of the λ light chain is shown as SEQ ID NO: |

TABLE 6-continued

| Sequences of CD20 × CD3 κλ bispecific antibodies | |
|---|---|
| CD20 arm | CD3 arm |
| 110, and a nucleic acid encoding the κ light chain is shown as SEQ ID NO: 111<br>EIVLTQSPGTLSLSPGERATLSCRASQS<br>VSSYLAWYQKKPGQAPRLLIYDASNRAT<br>GIPDRFSGSGSGTDFTLTISRLEPEDFA<br>VYYCQQRSNWPITFGQGTKLEIKRTVAA<br>PSVFIFPPSDEQLKSGTASVVCLLNNFY<br>PREAKVQWKVDNALQSGNSQESVTEQDS<br>KDSTYSLSSTLTLSKADYEKHKVYACEV<br>THQGLSSPVTKSFNRGEC* | 106, and a nucleic acid encoding the λ light chain is shown as SEQ ID NO: 107<br>QAVVTQEPSLTVSPGGTVTLTCRSSTGA<br>VTTSNYANWVQQKPGQAPRGLIGGTNKR<br>APWTPARFSGSLLGGKAALTITGAQAED<br>EAEYYCVLWYSNLWVFGGGTKLTVLGQP<br>KAAPSVTLFPPSSEELQANKATLVCLIS<br>DFYPGAVTVAWKADSSPVKAGVETTTPS<br>KQSNNKYAASSYLSLTPEQWKSHRSYSC<br>QVTHEGSTVEKTVAPTECS* |
| Heavy chain 1: an amino acid sequence of heavy chain 1 is shown as SEQ ID NO: 112, and a nucleic acid encoding heavy chain 2 is shown as SEQ ID NO: 113<br>EVQLLESGGGVVQPGGSLRLSCAASGFT<br>FNDYAMHWVREAPGKGLEWVSTISWNSG<br>SIGYADSVKGRFTISRDNSKNTLYLQMN<br>SLRAEDTAVYYCAKDIQYGNYYYGMDYW<br>GQGTLVTVSSASTKGPSVFPLAPCSRST<br>SESTAALGCLVKDYFPEPVTVSWNSGAL<br>TSGVHTFPAVLQSSGLYSLSSVVTVPSS<br>SLGTKTYTCNVDHKPSNTKVDKRVESKY<br>GPPCPPCPAPEFEGGPSVFLFPPKPKDT<br>LMISRTPEVTCVVVDVSQEDPEVQFNWY<br>VDGVEVHNAKTKPREEQFNSTYRVVSVL<br>TVLHQDWLNGKEYKCKVSNKGLASSIEK<br>TISKAKGQPREPQVCTLPPSQEEMTKNQ<br>VSLSCAVKGFYPSDIAVEWESNGQPENN<br>YKTTPPVLDSDGSFFLVSKLTVDKSRWQ<br>EGNVFSCSVMHEALHNHYTQKSLSLSLG<br>K* | Heavy chain 2: an amino acid sequence of heavy chain 2 is shown as SEQ ID NO: 108, and a nucleic acid encoding heavy chain 2 is shown as SEQ ID NO: 109<br>EVQLVESGGGLVQPGGSLRLSCAASGFT<br>FNTYAMNWVRQAPGKGLEWVGRIRSKYN<br>NYATYYADSVKDRFTISRDDSKNSLYLQ<br>MNSLKTEDTAVYYCVRHGNFGNSYVSWF<br>AYWGQGTLVTVSSASTKGPSVFPLAPCS<br>RSTSESTAALGCLVKDYFPEPVTVSWNS<br>GALTSGVHTFPAVLQSSGLYSLSSVVTV<br>PSSSLGTKTYTCNVDHKPSNTKVDKRVE<br>SKYGPPCPPCPAPEFEGGPSVFLFPPKP<br>KDTLMISRTPEVTCVVVDVSQEDPEVQF<br>NWYVDGVEVHNAKTKPREEQFNSTYRVV<br>SVLTVLHQDWLNGKEYKCKVSNKGLASS<br>IEKTISKAKGQPREPQVYTLPPCQEEMT<br>KNQVSLWCLVKGFYPSDIAVEWESNGQP<br>ENNYKTTPPVLDSDGSFFLYSKLTVDKS<br>RWQEGNVFSCSVMHEALHNHYTQKSLSL<br>SLGK* |
| CD20 × CD3 κλ005 (SEQ ID NO: 102-105, and 114-117): $V\lambda_{CD3}$: $Gln_{40}Glu$; $VH_{CD3}$: $Gln_{39}Lys$ | |
| κ light chain: an amino acid sequence of the κ light chain is shown as SEQ ID NO: 102, and a nucleic acid encoding the κ light chain is shown as SEQ ID NO: 103<br>EIVLTQSPGTLSLSPGERATLSCRASQS<br>VSSYLAWYQQKPGQAPRLLIYDASNRAT<br>GIPDRFSGSGSGTDFTLTISRLEPEDFA<br>VYYCQQRSNWPITFGQGTKLEIKRTVAA<br>PSVFIFPPSDEQLKSGTASVVCLLNNFY<br>PREAKVQWKVDNALQSGNSQESVTEQDS<br>KDSTYSLSSTLTLSKADYEKHKVYACEV<br>THQGLSSPVTKSFNRGEC* | λ light chain: an amino acid sequence of the λ light chain is shown as SEQ ID NO: 114, and a nucleic acid encoding the λ light chain is shown as SEQ ID NO: 115<br>QAVVTQEPSLTVSPGGTVTLTCRSSTGA<br>VTTSNYANWVQEKPGQAPRGLIGGTNKR<br>APWTPARFSGSLLGGKAALTITGAQAED<br>EAEYYCVLWYSNLWVFGGGTKLTVLGQP<br>KAAPSVTLFPPSSEELQANKATLVCLIS<br>DFYPGAVTVAWKADSSPVKAGVETTTPS<br>KQSNNKYAASSYLSLTPEQWKSHRSYSC<br>QVTHEGSTVEKTVAPTECS* |
| Heavy chain 1: an amino acid sequence of heavy chain 1 is shown as SEQ ID NO: 104, and a nucleic acid encoding heavy chain 1 is shown as SEQ ID NO: 105<br>EVQLLESGGGVVQPGGSLRLSCAASGFT<br>FNDYAMHWVRQAPGKGLEWVSTISWNSG<br>SIGYADSVKGRFTISRDNSKNTLYLQMN<br>SLRAEDTAVYYCAKDIQYGNYYYGMDYW<br>GQGTLVTVSSASTKGPSVFPLAPCSRST<br>SESTAALGCLVKDYFPEPVTVSWNSGAL<br>TSGVHTFPAVLQSSGLYSLSSVVTVPSS<br>SLGTKTYTCNVDHKPSNTKVDKRVESKY<br>GPPCPPCPAPEFEGGPSVFLFPPKPKDT<br>LMISRTPEVTCVVVDVSQEDPEVQFNWY<br>VDGVEVHNAKTKPREEQFNSTYRVVSVL<br>TVLHQDWLNGKEYKCKVSNKGLASSIEK<br>TISKAKGQPREPQVCTLPPSQEEMTKNQ<br>VSLSCAVKGFYPSDIAVEWESNGQPENN<br>YKTTPPVLDSDGSFFLVSKLTVDKSRWQ | Heavy chain 2: an amino acid sequence of heavy chain 2 is shown as SEQ ID NO: 116, and a nucleic acid encoding heavy chain 2 is shown as SEQ ID NO: 117<br>EVQLVESGGGLVQPGGSLRLSCAASGFT<br>FNTYAMNWVRKAPGKGLEWVGRIRSKYN<br>NYATYYADSVKDRFTISRDDSKNSLYLQ<br>MNSLKTEDTAVYYCVRHGNFGNSYVSWF<br>AYWGQGTLVTVSSASTKGPSVFPLAPCS<br>RSTSESTAALGCLVKDYFPEPVTVSWNS<br>GALTSGVHTFPAVLQSSGLYSLSSVVTV<br>PSSSLGTKTYTCNVDHKPSNTKVDKRVE<br>SKYGPPCPPCPAPEFEGGPSVFLFPPKP<br>KDTLMISRTPEVTCVVVDVSQEDPEVQF<br>NWYVDGVEVHNAKTKPREEQFNSTYRVV<br>SVLTVLHQDWLNGKEYKCKVSNKGLASS<br>IEKTISKAKGQPREPQVYTLPPCQEEMT<br>KNQVSLWCLVKGFYPSDIAVEWESNGQP<br>ENNYKTTPPVLDSDGSFFLYSKLTVDKS |

TABLE 6-continued

| Sequences of CD20 × CD3 κλ bispecific antibodies | |
|---|---|
| CD20 arm | CD3 arm |
| EGNVFSCSVMHEALHNHYTQKSLSLSLG K* | RWQEGNVFSCSVMHEALHNHYTQKSLSL SLGK* |

Expression and Purification of CD20×CD3 κλ Bispecific Antibodies

Plasmids encoding corresponding antibody fragments were mixed in a ratio of κ light chain.) light chain heavy chain 1: heavy chain 2 being 2:2:1:1, mixed with 3 mg/mL PEI, co-transfected into CHO-S cells, and cultured in 500 mL of CD CHO AGT medium (Gibco#12490-001) at 37° C. and 150 rpm under 5% $CO_2$, and a 4% CHO Feed C+ supplement (Gibco #A25031-05) was added at day 2, day 4 and day 6 of transient transfection. After the cell viability decreased to about 85%, a fermentation broth was harvested, filtered, and purified by Protein A affinity chromatography. The cell solution was concentrated and resuspended in PBS, the absorbance was measured (Nanodrop), and the protein concentration was calculated based on the theoretical extinction coefficient.

Figure 12:
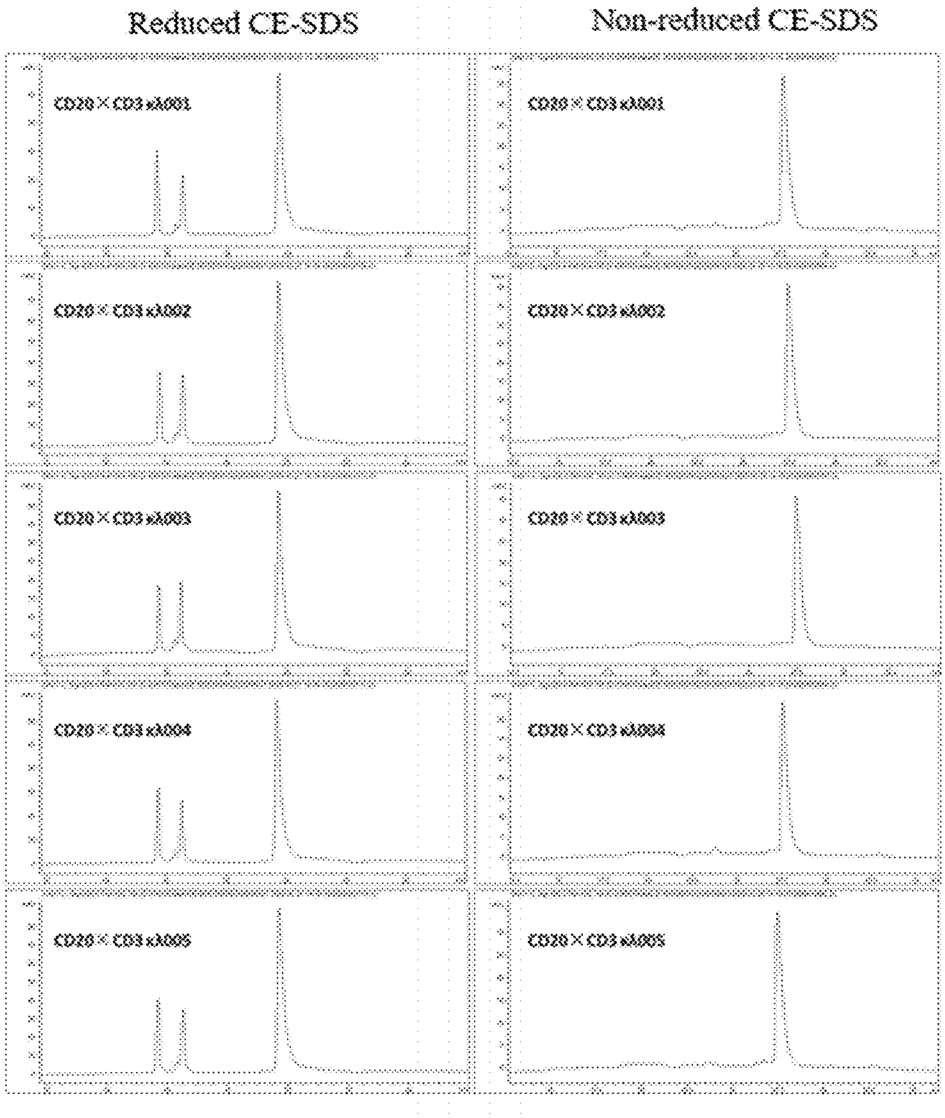
FIG. 12 shows capillary electrophoresis results of a CD20×CD3 κλ bispecific antibody.

SEC-HPLC and capillary electrophoresis results show that the purity of a monomer in the CD20×CD3 κλ bispecific antibody is close to or higher than 90% (see Table 7), and a ratio of κ light chain to λ light chain is close to 1:1 (see FIG. 12).

TABLE 7

Purity of CD20 × CD3 κλ bispecific antibody monomers (SEC-HPLC)

| | SEC-HPLC (%) | | |
|---|---|---|---|
| κλ bispecific antibody | Polymer | Monomer | Fragment |
| CD20 × CD3 κλ001 | 4.1 | 92.5 | 3.5 |
| CD20 × CD3 κλ002 | 4.6 | 90.8 | 4.5 |
| CD20 × CD3 κλ003 | 3.1 | 88.3 | 8.6 |
| CD20 × CD3 κλ004 | 4.8 | 91.1 | 4.0 |
| CD20 × CD3 κλ005 | 6.0 | 90.5 | 3.5 |

Figure 13:
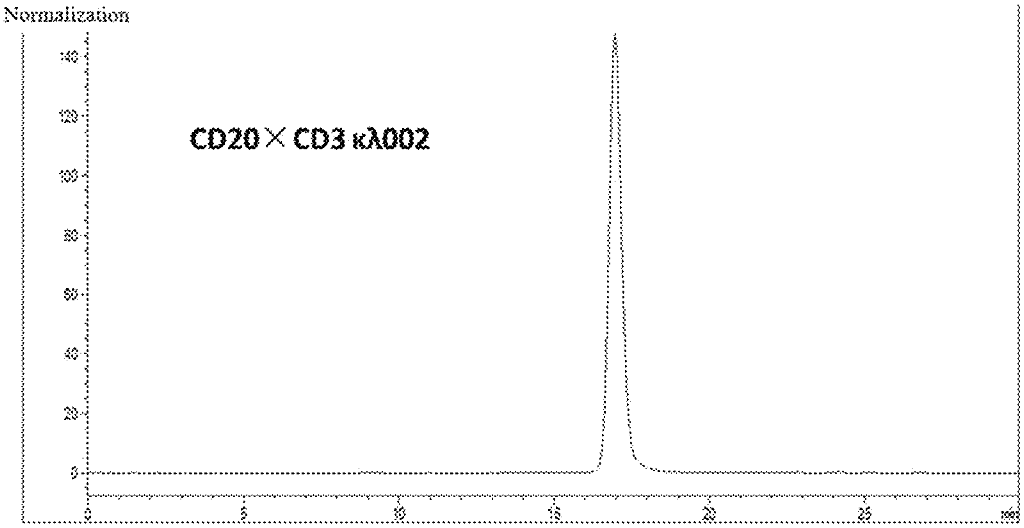
FIG. 13 shows the purification of a CD20×CD3 378 λ bispecific antibody.
Figure 14:
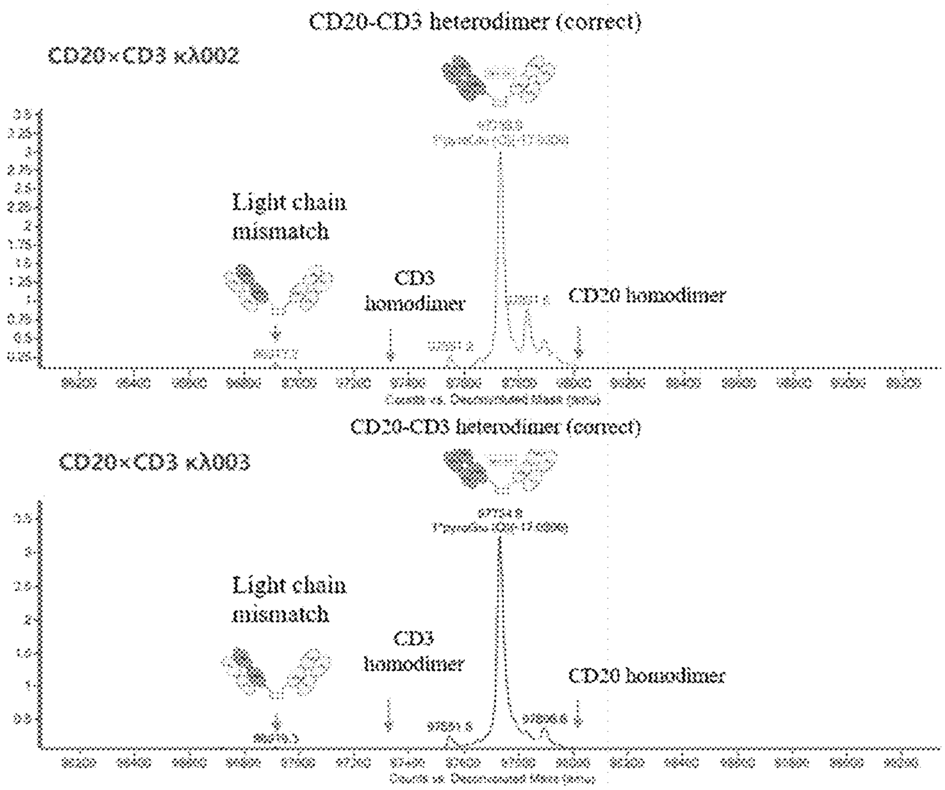
FIG. 14 shows mass spectrometry results of a CD20×CD3 κλ bispecific antibody.

The CD20×CD3 κλ bispecific antibodies were further refined and purified by Capto S ImpAct ion exchange chromatography, and elution peaks were combined through gradient elution. SEC-HPLC results show that the monomer content is higher than 99% (see FIG. 13). In the purified CD20×CD3 κλ002 and CD20×CD3 κλ003 samples, the light chain mismatch rate is extremely low (<1%), and no CD3 homodimers or CD20 homodimers are detected (see FIG. 14).

Example 6 Binding Activity of CD20×CD3 κλ Bispecific Antibodies

The affinity of the CD20 antigen arm of the bispecific antibody was determined by detecting the binding to stably transfected cells overexpressing CD20 or CD20+ tumor cells, and the affinity of the CD3 arm of the bispecific antibody was determined by detecting the binding to a recombinant CD3 antigen, Jurkat cells or freshly separated peripheral blood T cells. Detection results show that the affinity of the novel CD20×CD3 κλ bispecific antibody to tumor cells is about 3 to 5 times higher than the affinity to T cells. A positive control antibody bsAB1 was synthesized and expressed with reference to document US20170174781.

1. Binding of CD20×CD3 κλ Bispecific Antibodies to Human and Monkey CD20 Stably Transfected Cells The CHO-human CD20 and CHO-monkey CD20 stably transfected cells prepared in Example 1 in the logarithmic growth phase were taken and adjusted with 4% calf serum (Hyclone, SH30626.06) to a concentration of $5\times10^5$ cells/mL, 100 μL of cell suspension was added to each well of a 96-well U-shaped plate and centrifuged at 300 g for 5 min, a supernatant was discarded, 100 μL of gradient-diluted antibody (the initial concentration of 1800 nM, 3-fold dilution, 12 gradients) was added to each well, and the mixture was incubated at 4° C. for 60 min. 50 μL of Alexa Fluro647-labelled goat anti-human IgG Fc (1: 300 dilution) was added as a secondary antibody to each well, the mixture was incubated on ice for 20 min and washed once, 50 μL of PI solution (1:300) was added to each well, and the mixture was incubated for 5 min and detected by using a flow cytometer.

Figure 15:
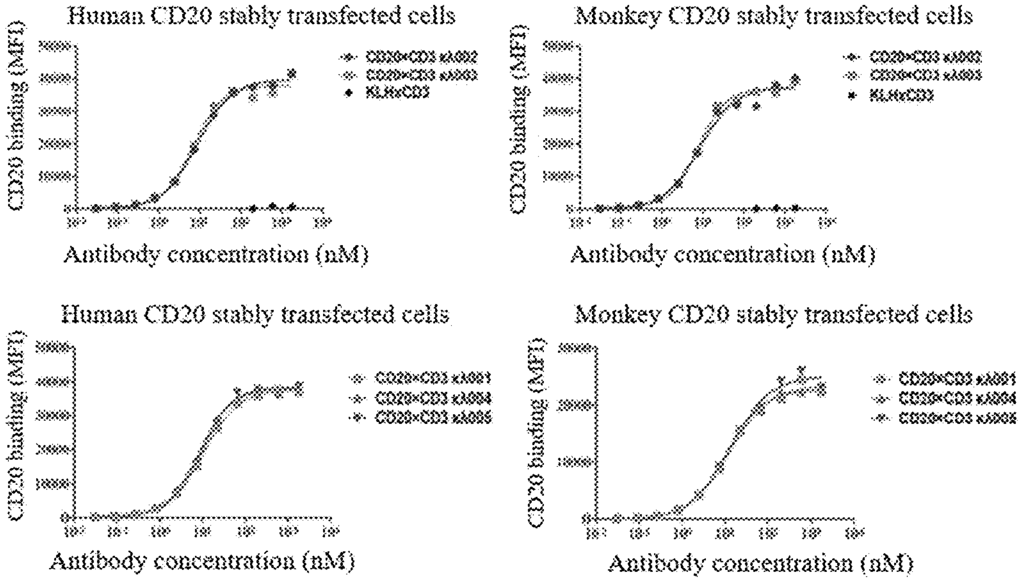
FIG. 15 shows the binding of a CD20×CD3 κλ bispecific antibody to CD20 stably transfected cells.

FIG. 15 and Table 8 show that the CD20×CD3 κλ bispecific antibodies bind to CD20 receptors on cells with high affinity, and the affinity to human and monkey CD20 stably transfected cells is equivalent.

TABLE 8

Binding of CD20 × CD3 κλ bispecific antibodies to CD20 stably transfected cells

| EC50 | Human CD20-CHO | Monkey CD20-CHO |
|---|---|---|
| CD20 × CD3 κλ001 | 10 nM | 12 nM |
| CD20 × CD3 κλ002 | 9 nM | 8 nM |
| CD20 × CD3 κλ003 | 7 nM | 8 nM |
| CD20 × CD3 κλ004 | 8 nM | 10 nM |
| CD20 × CD3 κλ005 | 9 nM | 14 nM |
| KLH × CD3 | Not bind | Not bind |

2. Binding of CD20×CD3 κλ Bispecific Antibodies to Human $CD20^+$ Tumor Cells

SU-DHL-4, Raji and NALM-6 cells in the logarithmic growth phase were taken, 200 μg/mL mouse IgG (Jackson ImmunoResearch, 115-005-03) was added, the mixture was blocked in an ice-bath for 30 min, the cells were adjusted with 4% calf serum to a concentration of $5\times10^5$ cells/mL, 100 μL of cell suspension was added to each well of a 96-well U-shaped plate and centrifuged at 300 g for 5 min, a supernatant was discarded, 100 μL of gradient-diluted antibody (the initial concentration of 1800 nM, 3-fold dilution, 12 gradients) was added to each well, and the mixture was incubated at 4° C. for 60 min. The primary antibody was washed away, 50 μL of Alexa Fluro647-labelled goat anti-human IgG Fc (1: 300 dilution) was added to each well, the mixture was incubated on ice for 20 min and washed once, 50 μL of PI was added to each well, and the mixture was incubated for 5 min and detected by using a flow cytometer.

Figure 16:
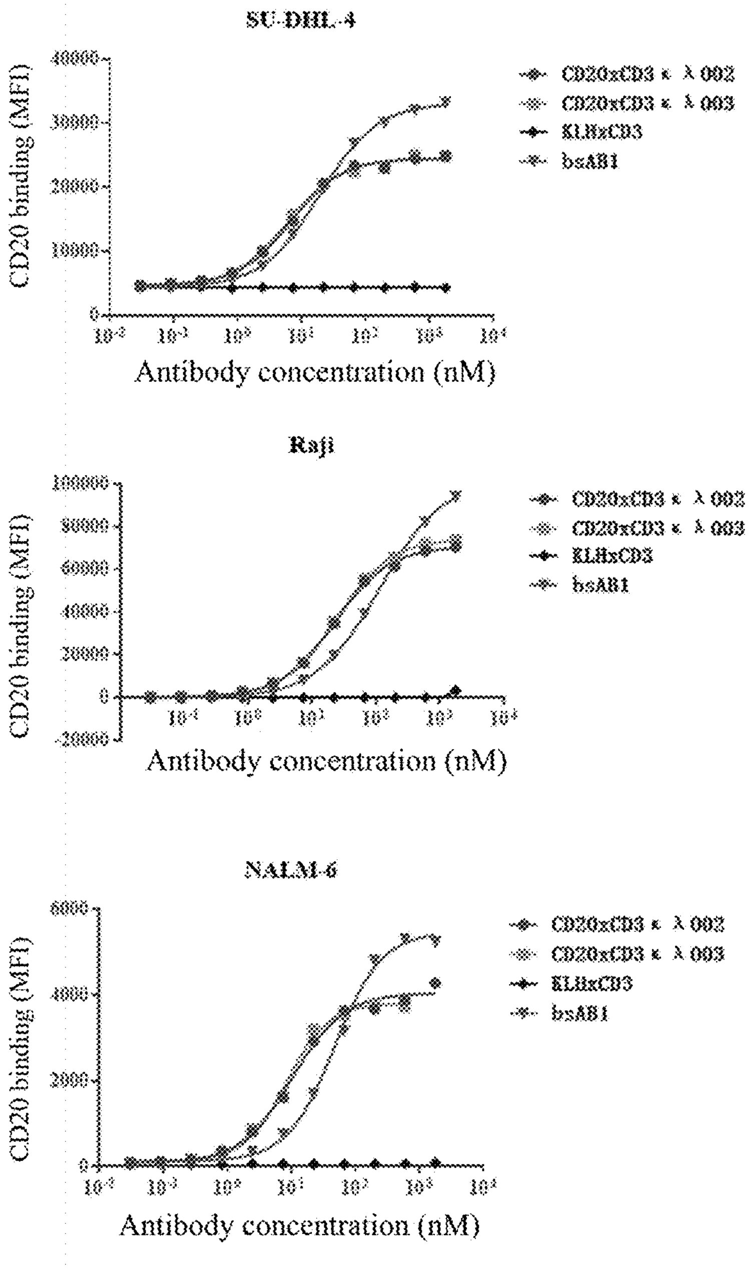
FIG. 16 shows that a CD20×CD3 κλ bispecific antibody binds to $CD20^+$ tumor cells with high affinity.

Detection results are shown in FIG. 16 and Table 9, the CD20×CD3 κλ bispecific antibodies bind to CD20+tumor cells SU-DHL-4, Raji and NALM-6 with high affinity.

TABLE 9

| Binding of CD20 × CD3 κλ bispecific antibodies to CD20+ tumor cells | | | |
|---|---|---|---|
| $EC_{50}$ (nM) | SU-DHL-4 | Raji | NALM-6 |
| CD20 × CD3 κλ002 | 7 | 23 | 10 |
| CD20 × CD3 κλ003 | 6 | 25 | 8 |
| bsAB1 | 19 | 115 | 48 |
| KLH × CD3 | Not bind | Not bind | Not bind |

3. Binding of CD20×CD3 κλ Bispecific Antibodies to Recombinant Human and Monkey CD3 Antigens 1 μg/mL recombinant human or monkey CD3γ/ε antigen was coated onto a plate and placed at 4° C. overnight. After the recombinant human or monkey CD3γ/ε antigen was blocked with skimmed milk, 100 μL of antibody (the initial concentration of 60 μg/mL, 3-fold dilution, a total of 12 gradients) was added to each well, and the mixture was incubated at room temperature for 1 h. 100 μL of goat anti-human F'(ab)2 (1:4000 dilution) was added as a secondary antibody to each well, and the mixture was incubated at room temperature for 1 h. TMB was added for color developing, 50 μL of concentrated sulfuric acid was added to terminate the reaction, the optical density at 450 nm was read by using a microplate reader, and a three-parameter fitting curve was drawn by using Graphpad software.

Figure 17:
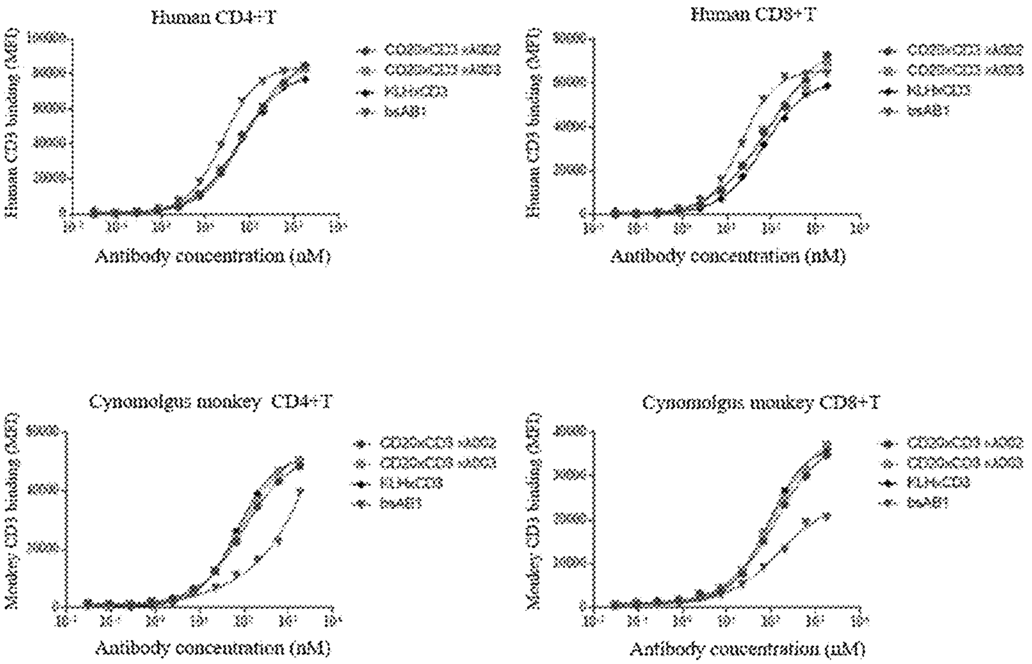
FIG. 17 shows the binding of a CD20×CD3 κλ bispecific antibody to recombinant human and cynomolgus monkey CD3εγ antigens.

Detection results are shown in FIG. 17, the CD20×CD3 κλ bispecific antibodies recognize the recombinant human and Cynomolgus monkey CD3εγ antigens with equivalent affinity.

4. Affinity Assay of CD20×CD3 κλ Bispecific Antibodies to Recombinant CD3 Antigen 10 μg/mL recombinant human or monkey CD3εγ antigen was bound to a CMS chip (GE healthcare) by amino coupling, and the binding amount of antigen was controlled to be about 200 RU. After the baseline was stable, the gradient-diluted antibody (the initial concentration of 10 μg/mL, 2-fold dilution, 7 gradients) flowed through the chip at a flow rate of 30 μL/min, with a binding time of 350 s and a dissociation time of 600 s. Kinetic constants were calculated by fitting data to a 1:1 binding model using Biacore T200 evaluation software Affinity assay results are shown in Table 10.

TABLE 10

| Affinity of CD20 × CD3 κλ bispecific antibodies to recombinant CD3 antigen | | |
|---|---|---|
| KD (nM) | Human CD3εγ | Monkey CD3εγ |
| CD20 × CD3 κλ002 | 24.2 | 31.5 |
| CD20 × CD3 κλ003 | 26.4 | 34.3 |
| KLH × CD3 | 21.6 | 21.6 |

5. Binding of CD20×CD3 κλ Bispecific Antibodies to Jurkat Cells

Jurkat cells in the logarithmic growth phase were taken, 200 μg/mL mouse IgG (Jackson ImmunoResearch, 115-005-03) was added, and the mixture was placed on ice for 30 min. The cells were adjusted with 4% calf serum to a concentration of 5×105 cells/mL, 100 μL of cell suspension was added to each well of a 96-well U-shaped plate and centrifuged at 300 g, a supernatant was centrifuged, 100 μL of gradient-diluted antibodies (the initial concentration of 1800 nM, 3-fold dilution, 12 gradients) was added to each well, and the mixture was incubated at 4° C. for 60 min. 50 μL of Aleκλ Fluro647-labelled goat anti-human IgG Fc (1: 300 dilution) was added as a secondary antibody to each well, the mixture was incubated on ice for 20 min and washed once, 50 μL of PI was added to each well, and the mixture was incubated for 5 min and detected by using a flow cytometer (BD C6).

Figure 18:
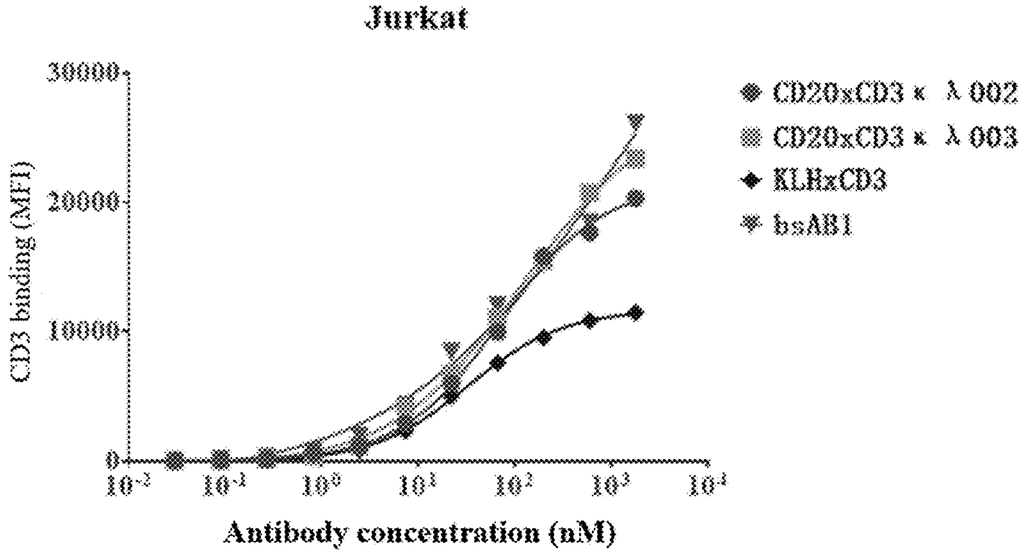
FIG. 18 shows the binding of a CD20×CD3 κλ bispecific antibody to Jurkat cells.

Detection results are shown in FIG. 18 and Table 11, the CD20×CD3 κλ bispecific antibodies bind to human leukemia T cell line Jurkat cells with moderate affinity, and $EC_{50}$ is about 71-120 nM, which is 10 times lower than the binding force of the CD20 antigen arm to CD20 receptor.

TABLE 11

| Binding of CD20 × CD3 κλ bispecific antibodies to Jurkat cells | |
|---|---|
| EC50 | Jurkat |
| CD20 × CD3 κλ002 | 71 nM |
| CD20 × CD3 κλ003 | 120 nM |
| bsAB1 | ND |
| KLH × CD3 | 33 nM |

ND: not reach saturation at high concentration

6. Binding of CD20×CD3 κλ Bispecific Antibodies to Human or Cynomolgus Monkey Peripheral Blood T Cells Fresh human or Cynomolgus monkey peripheral blood was taken and separated by Ficoll.Paque Plu (GE, 17-1440-03) to obtain PBMCs, The PBMCs was adjusted with 4% calf serum (Hyclone, SH30626.06) to a concentration of $5\times10^5$ cells/mL, 100 μL of cell suspension was added to each well of a 96-well U-shaped plate and centrifuged, a supernatant was discarded, 100 μL of gradient-diluted antibodies (the initial concentration of 1800 nM, 3-fold dilution, 11 gradients) was added to each well, and the mixture was incubated at 4° C. for 60 min. 50 μL of Alexa Fluro647-labelled goat anti-human IgG Fc (1:300 dilution) was added as a secondary antibody to each well, the mixture was placed in an ice-bath for 20 min and washed once, 50 μL of PI was added to each well, and the mixture was incubated for 5 min and detected by using a flow cytometer (BD C6).

Figure 19:
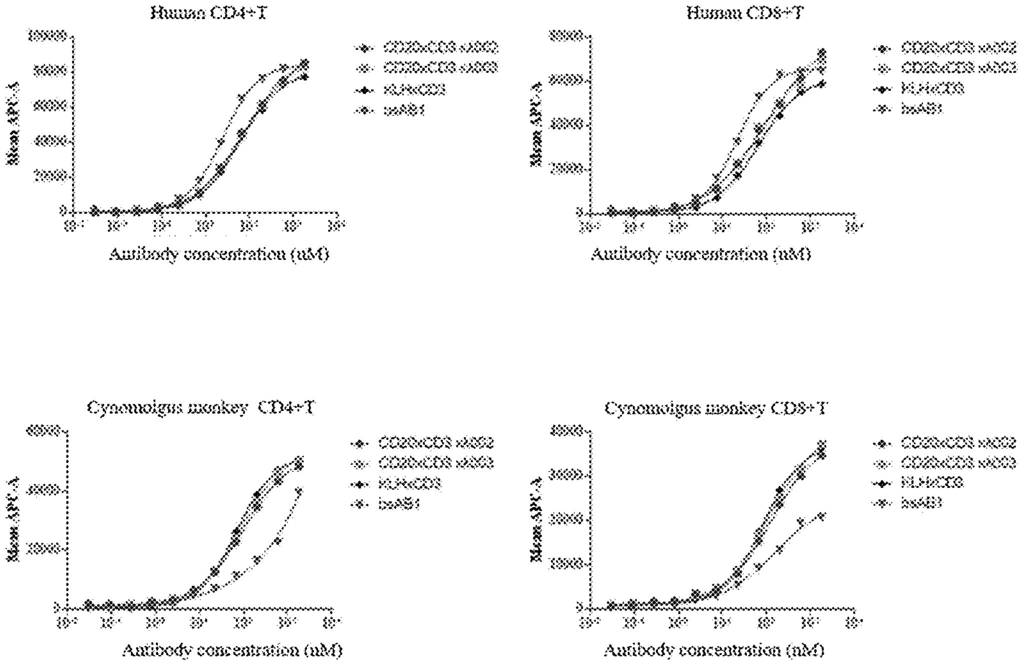
FIG. 19 shows the binding of a CD20×CD3 κλ bispecific antibody to human peripheral blood T cells.

Detection results are shown in FIG. 19 and Table 12, the CD20×CD3 κλ bispecific antibodies recognize human or Cynomolgus monkey peripheral blood CD4+T and CD8+T cells, the affinity to human T cells is about 65-98 nM, the affinity to Cynomolgus monkey T cells is about 89-124 nM, the affinity is equivalent and 10 times weaker than the binding force of the CD20 antigen arm to CD20 receptor, which is conducive to the preferential enrichment of the bispecific antibodies to tumor cells.

TABLE 12

| Binding of CD20 × CD3 κλ bispecific antibodies to peripheral blood T cells | | | | |
|---|---|---|---|---|
| EC50 (nM) | Human $CD4^+T$ | Human $CD8^+T$ | Monkey $CD4^+T$ | Monkey $CD8^+T$ |
| CD20 × CD3 κλ002 | 73 | 98 | 97 | 124 |
| CD20 × CD3 κλ003 | 69 | 65 | 89 | 120 |
| bsAB1 | 25 | 22 | ND | 150 |
| KLH-CD3 | 62 | 65 | 69 | 85 |

ND: not reach saturation at high concentration

Example 7 CD20×CD3 x7 Bispecific Antibody-Mediated TDCC

Freshly separated PMBCs were taken and mixed with target cells NALM-6, TMD-8 and Toledo in the logarithmic growth phase, respectively, in an effector/target cell ratio of 8:1, 50 μL of gradient-diluted antibody (the initial concentration of 66.7 nM, 10-fold dilution, 8 gradients) was added to each well, and the mixture was cultured at 37° C. under 5% $CO_2$ for 24 h. After culture was completed, 50 μL of supernatant was transferred to a new black ELISA plate, 50 μL of LDH detection substrate was added to each well, the reaction was terminated after 10 min, LDH release was detected, the remaining cells in the wells were washed twice with 4% calf serum, 100 μg/mL human IgG was added, the mixture was incubated for 10 min, T cell activation detection antibodies (CD25-PE, CD4-APC, CD69-FITC, and CD8-APC) were added, and the mixture was incubated on ice for 20 min. The mixture was washed, a supernatant was discarded, 60 μL of PI was added to each well, the mixture was incubated on ice for 5 min and detected by using a flow cytometer.

Figure 20:
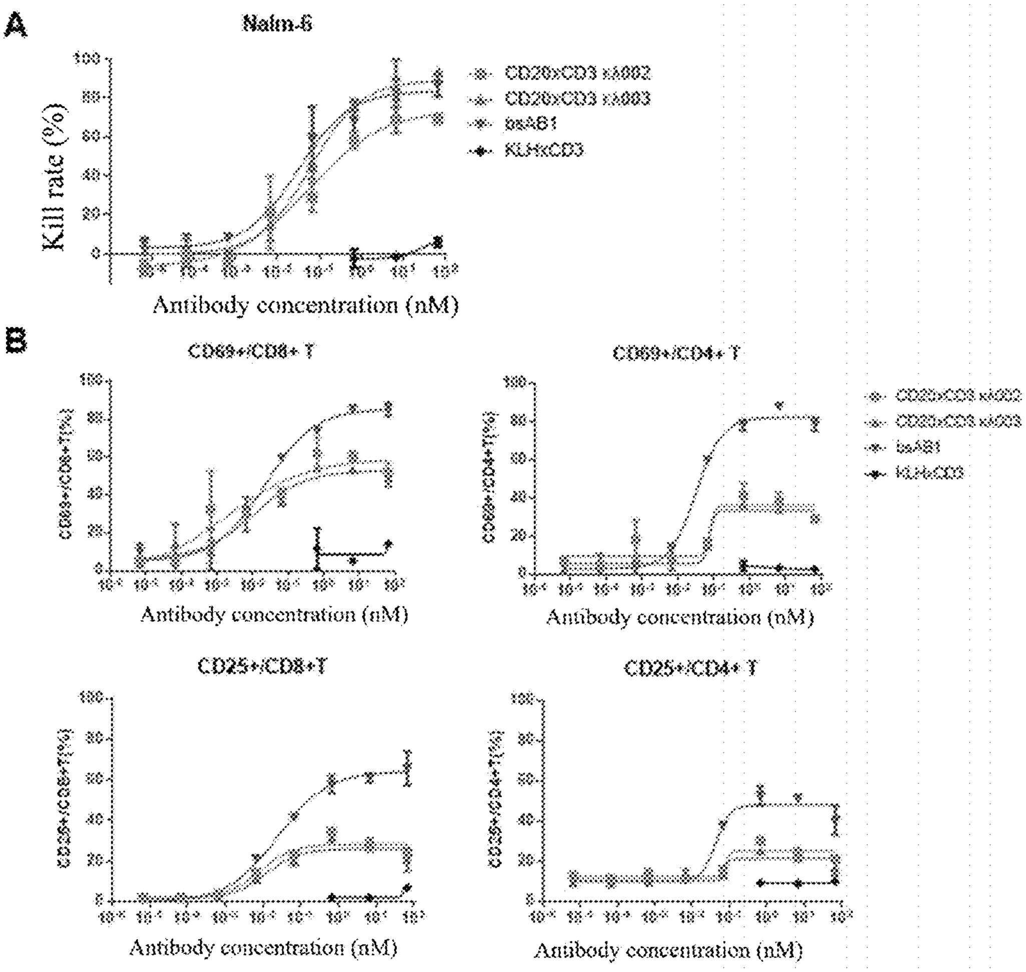
Figure 21:
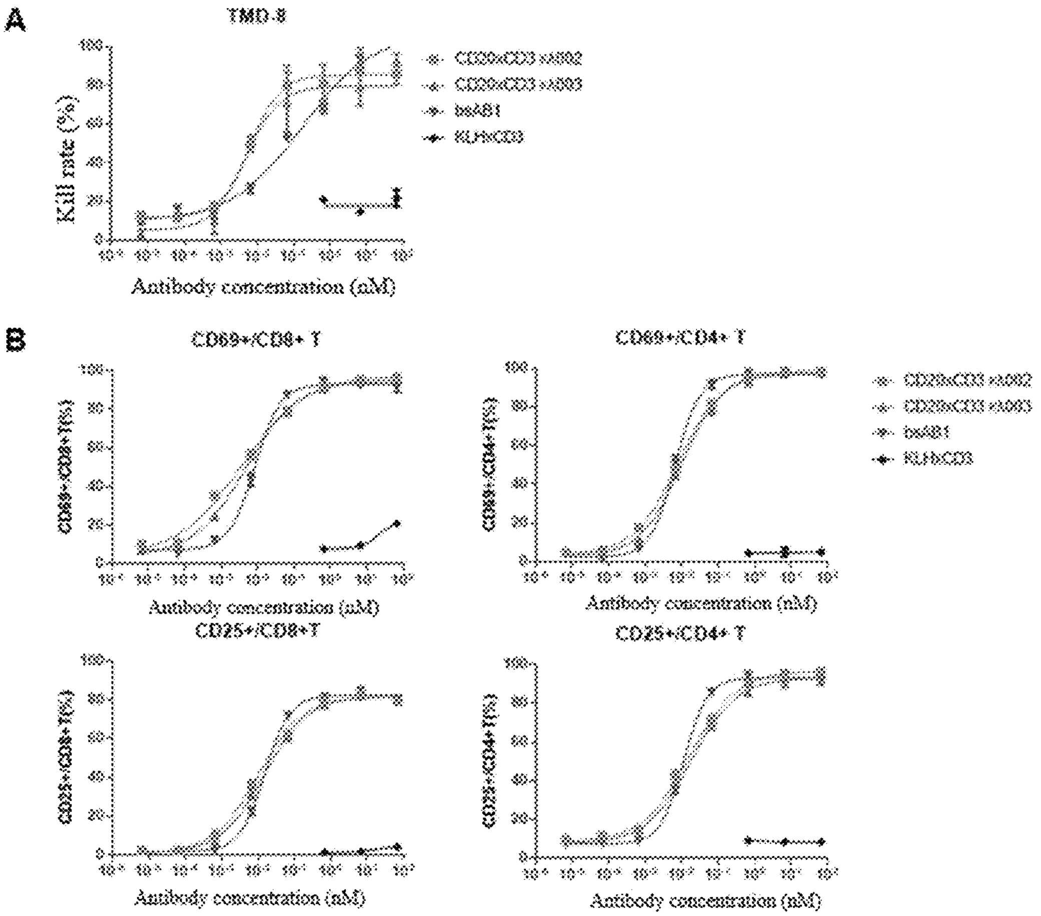
Figure 22:
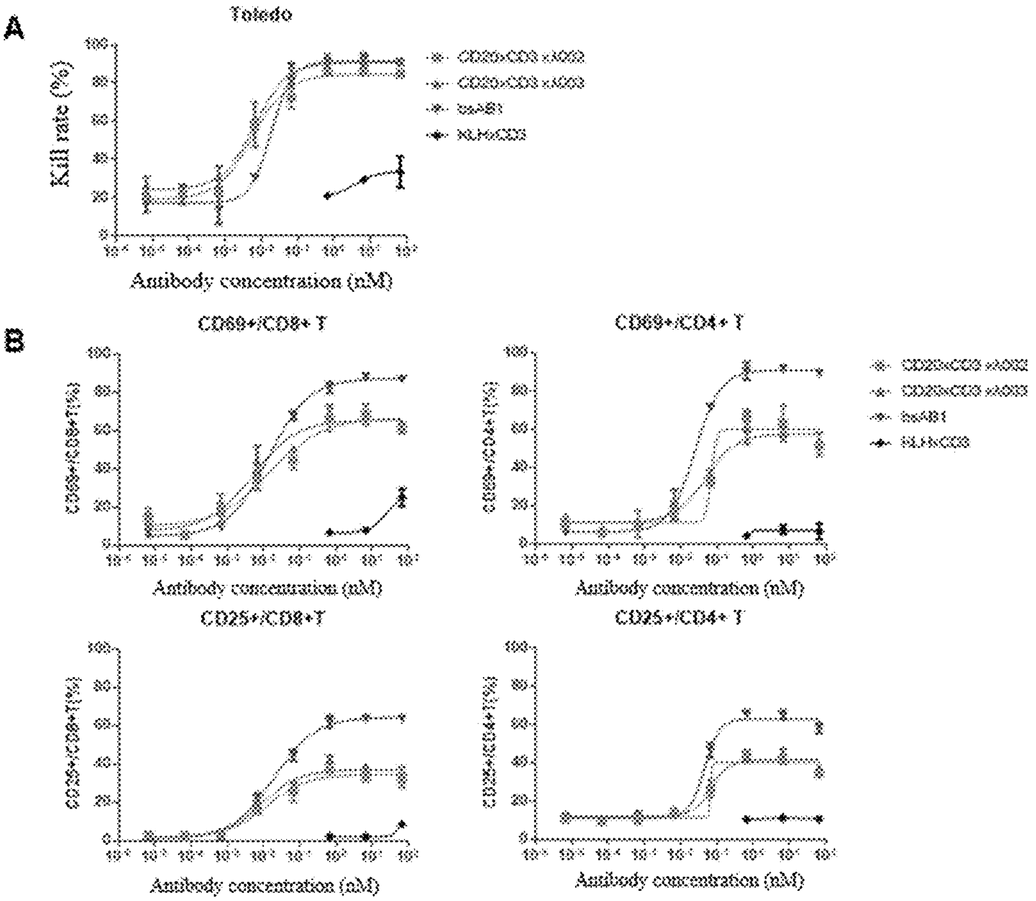

FIG. 20A and FIG. 20B respectively show the killing of human lymphoid leukemia cells Nalm-6 and the activation of T cells by the CD20×CD3 κλ bispecific antibodies. FIG. 21A and FIG. 21B respectively show the killing of TMD-8 cells and the activation of T cells by the CD20×CD3 κλ bispecific antibodies. FIG. 22A and FIG. 22B respectively show the killing of Toledo cells and the activation of T cells by the CD20×CD3 κλ bispecific antibodies. For tumor cells Nalm-6, TMD-8 and Toledo with different CD20 expression levels, both CD20×CD3 κλ002 and CD20×CD3 κλ003 can mediate effective T cell killing, the killing activity is equivalent to or slightly stronger than that of the control antibody bsAB1, the activation effect on T cells is milder than that of the latter.

Example 8 Activation of T Cell Activation Pathway by CD20×CD3 κλ Bispecific Antibodies Jurkat-NFAT-luc reporter cells and CD20-positive target cells (SU-DHL-4, Raji and NALM-6 cells) in the logarithmic growth phase were taken and centrifuged, a supernatant was discarded, and the cells were resuspended to a concentration of $2\times10^6$ cells/mL. 50 μL of target cells were inoculated into each well of a 96-well plate and centrifuged at 300 g for 5 min, a supernatant was discarded, 50 μL of Jurkat-NFAT-luc reporter cells was inoculated into each well of the 96-well plate, 50 μL of gradient-diluted CD20×CD3 κλ bispecific antibody or control antibody KLH×CD3 (the initial concentration of 20 μg/mL, 10-fold dilution, 10 gradients) was added to each well, and the mixture was incubated at 37° C. under 5% $CO_2$ for 6 h. After culture was completed, referring to the manual of ONE-Glo Luciferase Assay System, 100 μL of detection reagent was added to each well, and the mixture was placed at room temperature for 3 min and detected by using a microplate reader (Biotek Synergy HT).

Figure 23:
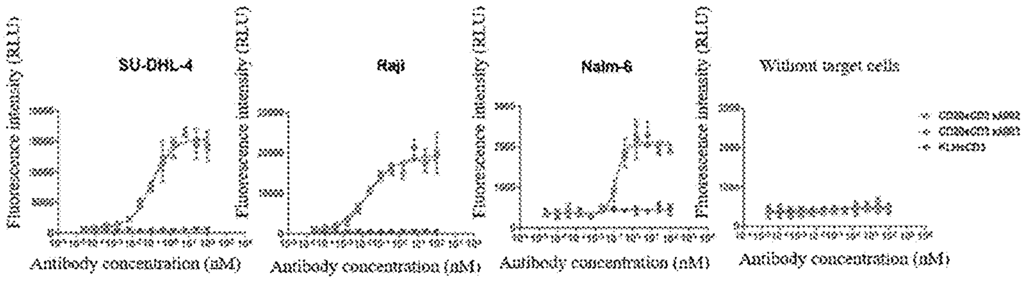
FIG. 23 shows the activation of T cell signaling pathway by a CD20×CD3 κλ bispecific antibody.

Detection results are shown in FIG. 23 and Table 13, and in a case that tumor cells with different CD20 expression levels serve as target cells, all the CD20×CD3 κλ bispecific antibodies can activate the NFAT signaling pathway of T cells.

TABLE 13

Activation of T cell NFAT pathway by CD20 × CD3 κλ bispecific antibodies

| $EC_{50}$ (nM) | SU-DHL-4 | Raji | NALM-6 |
|---|---|---|---|
| CD20 × CD3 κλ002 | 0.10 | 0.02 | 0.14 |
| CD20 × CD3 κλ003 | 0.11 | 0.02 | 0.14 |
| KLH × CD3 | — | — | — |

Example 9 Activation of Cytokine Release by CD20×CD3 κλ Bispecific Antibodies When mediating the killing of B-NHL tumor cells Raji or autologous B cells, the CD20×CD3 κλ bispecific antibodies can activate T cells and stimulate the release of related cytokines in PBMCs. $2\times10^5$ fresh PBMCs were mixed with $1\times10^5$ Raji cells and 50 μL of gradient-diluted antibody (the initial concentration of 66.7 nM, 10-fold dilution, 8 gradients), and the mixture was incubated at 37° C. under 5% $CO_2$ for 24 h. Contents of IL-2, IL-6, IFN-γ, TNF-α, etc. in a culture supernatant were detected by multi-index flow protein quantification for micro samples (cytometric bead array, (CBA)). The supernatant in the wells was discarded, the remaining cells in the wells were washed twice with 4% calf serum, 100 μg/mL human IgG was added, the mixture was blocked for 10 min, T cell activation detection reagents (CD25-PE, CD4-APC, CD69-FITC and CD8-APC) were added, and the mixture was incubated on ice for 20 min. The mixture was washed, a supernatant was discarded, 60 μL of PI was added to each well, the mixture was incubated for 5 min, and CD4+ and CD8+ T cell activation markers were detected by using a flow cytometer (BD FACS celesta). Steps of the killing test on autologous B cells were the same as above, but no Raji cells were added during incubation.

Figure 24:
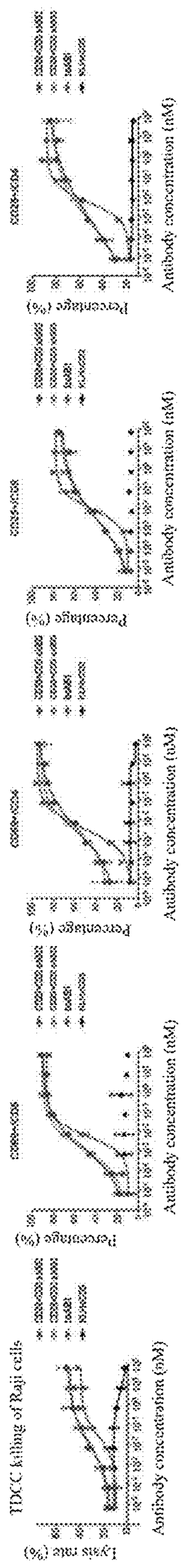
Figure 25:
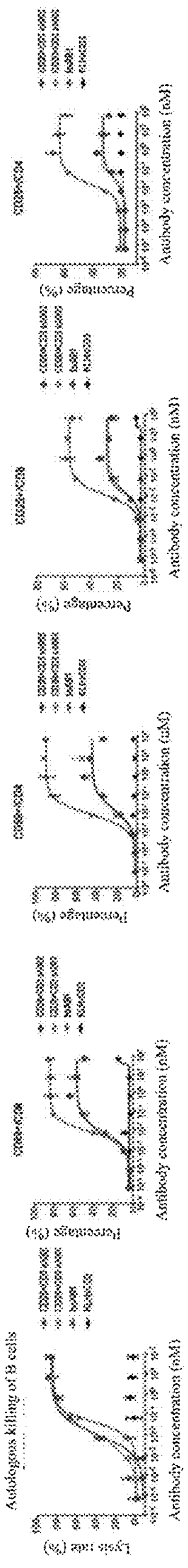
Figure 26:
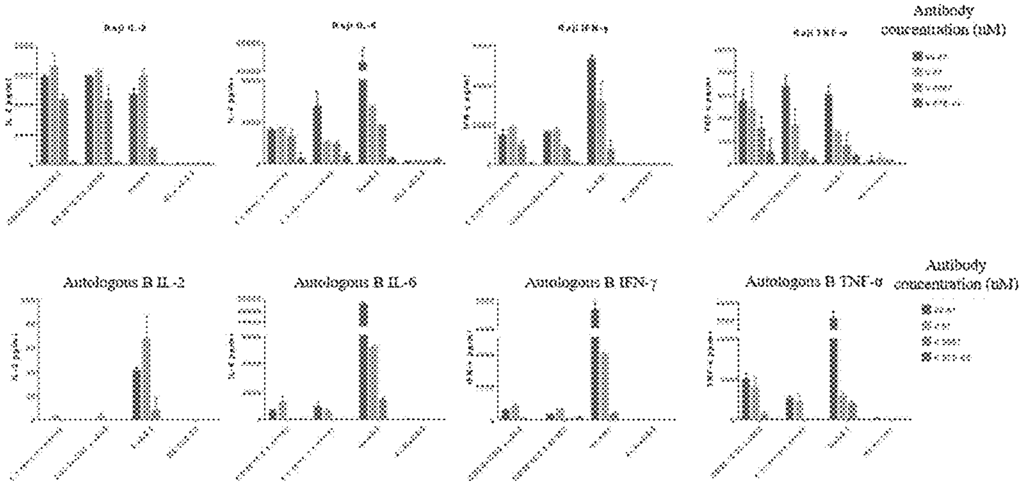

FIG. 24 shows the TDCC activity of the CD20×CD3 κλ bispecific antibodies on Raji cells and the activation of T cells in the process. FIG. 25 shows the elimination of autologous B cells by the CD20×CD3 κλ bispecific antibodies and the activation of T cells in the process. FIG. 26 shows the release of related cytokines during the killing of Raji cells or the elimination of autologous B cells. In a case that the CD20×CD3 κλ bispecific antibody is co-incubated with Raji cells highly expressing CD20 and PBMCs, or is incubated with PBMCs only, the CD20×CD3 κλ bispecific antibody-mediated killing activity on Raji cells or autologous B cells is equivalent to or slightly stronger than that of the control antibody bsAB1. However, the activation effect on T cells in the TDCC process is relatively milder, upregulation of the expression of the markers CD69 and CD25 is significantly lower or not higher than that of the control antibody. Similarly, the stimulated secretion amounts of cytokines IL-6, INF-γ, IL-2 and TNF-α are significantly less than or not greater than that of the latter, and the massive release of IL-6, INF-γ, etc. can trigger severe cytokine storm syndrome.

Example 10 Binding of CD20 ×CD3 κλ Bispecific Antibodies to Fcγ Receptor

50 μg/mL His-Tag antibody was conjugated to a CM5 chip through amino groups, and recombinant proteins FcγRI, FcγRIIAH131 and FcγRIIIAV158 with His tags (Sino Biological, #10256-H08H/10374-H08H1/10389-H08H1) were respectively captured for a capture time of 40 s at a flow rate of 10 μL/min. After the baseline was stable, the gradient-diluted antibody (the initial concentration of 37.5 μg/mL, 2-fold dilution) flowed through the chip at a flow rate of 30 μL/min for a binding time of 120 s and a dissociation time of 200 s, and affinity constants were obtained by fitting with Biacore evaluation software.

It can be seen from Table 14, the CD20×CD3 κλ antibodies do not bind to FcγRI, FcγRIIAH131 and FcγRIIIAV$_{158}$, the wild-type IgG4 control antibody binds to FcγRI with high affinity and weakly binds to FcγRIIAH131.

TABLE 14

Affinity of CD20 × CD3 κλ bispecific antibodies to Fcγ receptor

| KD | FcγRI | FcγRIIA$_{H131}$ | FcγRIIIA$_{V158}$ |
|---|---|---|---|
| CD20 × CD3 κλ002 | Not bind | Not bind | Not bind |
| CD20 × CD3 κλ003 | Not bind | Not bind | Not bind |
| IgG4 isotype control | 14 nM | Weak | Not bind |

Example 11 Immune Reconstituted Mouse Models of Subcutaneous Raji Transplantation Tumors 6-8-week-old female B-NGD mice (Biocytogen) were selected and subcutaneously inoculated with 3×10$^6$ Raji cells, after the tumor grew to 60mm3, the mice were randomly divided into groups that were respectively set as a 3.0 mg/kg administration group, a 0.6 mg/kg administration group, a 0.12 mg/kg administration group, and a negative control group (KLH×CD3, 3 mg/kg). 1×10$^7$ PBMC cells were injected into each mouse via the tail vein, the mice were subjected to administration for the first time 3 days later, and the administration was performed once every 5 days and in a total of 3 times. The tumor volume and body weight of the mice were monitored. After the experiment was completed, the mice were killed by neck dislocation, and tumors were taken out, weighed, and recorded.

Figure 27:
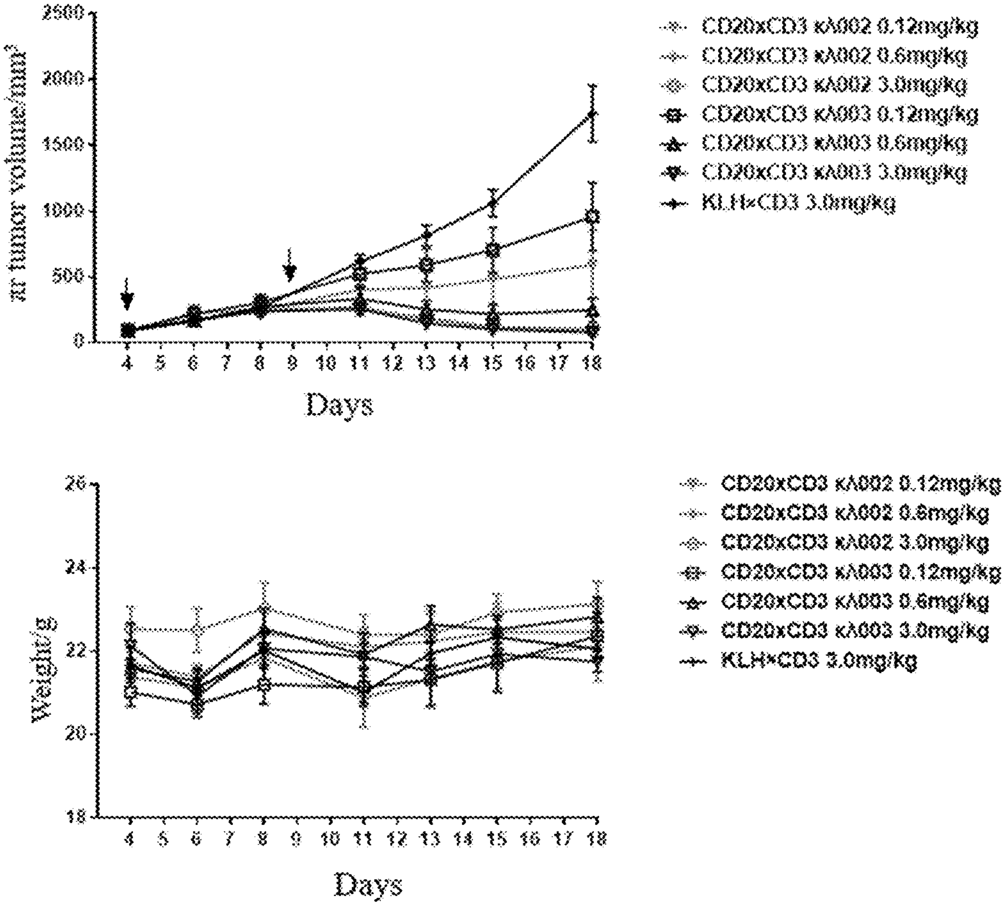
FIG. 27 shows an inhibiting effect of a CD20×CD3 κλ bispecific antibody on immunodeficient mouse models of subcutaneous Raji transplantation tumor.
Figure 28:
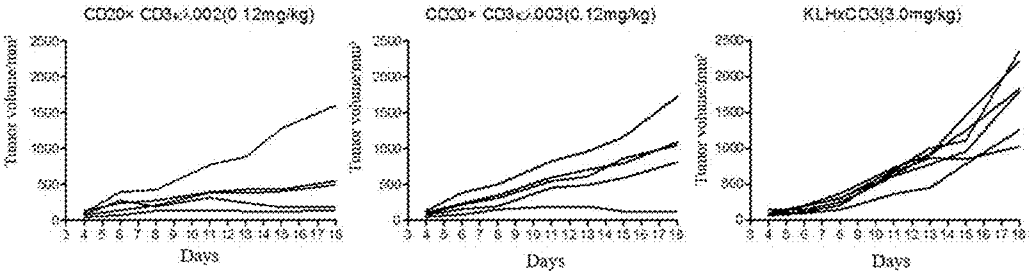

Results are shown in FIG. 27, the in vivo efficacy of the CD20×CD3 κλ bispecific antibody is dose-dependent, and the tumor inhibition rates of medium dose and high dose are 82% and 89%, respectively. The tumor-bearing mice tolerated the above doses well, without adverse reactions such as weight loss. FIG. 28 shows that the CD20×CD3 κλ002 achieves tumor inhibition (n=5) in 4 mice in the low-dose group (0.12 mg/kg).

Example 12 Immunodeficient Mouse Models of Subcutaneous Raji and Human PBMC Mixed Tumor 6-8-week-old female B-NGD mice (Biocytogen) were selected, Raji (3×10$^6$) and human PBMC (5×10$^6$) were mixed and inoculated subcutaneously in the mice, and after the tumor volume reached 60-100 mm$^3$, the mice were randomly divided into groups. The groups were respectively set as a 3.0 mg/mL administration group, a 0.6 mg/mL administration group, a 0.12 mg/mL administration group, and a negative group (KLH×CD3, 3 mg/kg). The administration was performed once every 5 days and in a total of 2 times. The tumor volume and body weight of the mice were monitored. After the experiment was completed, the mice were killed by neck dislocation, and tumors were taken out, weighed, and recorded.

Figure 29:
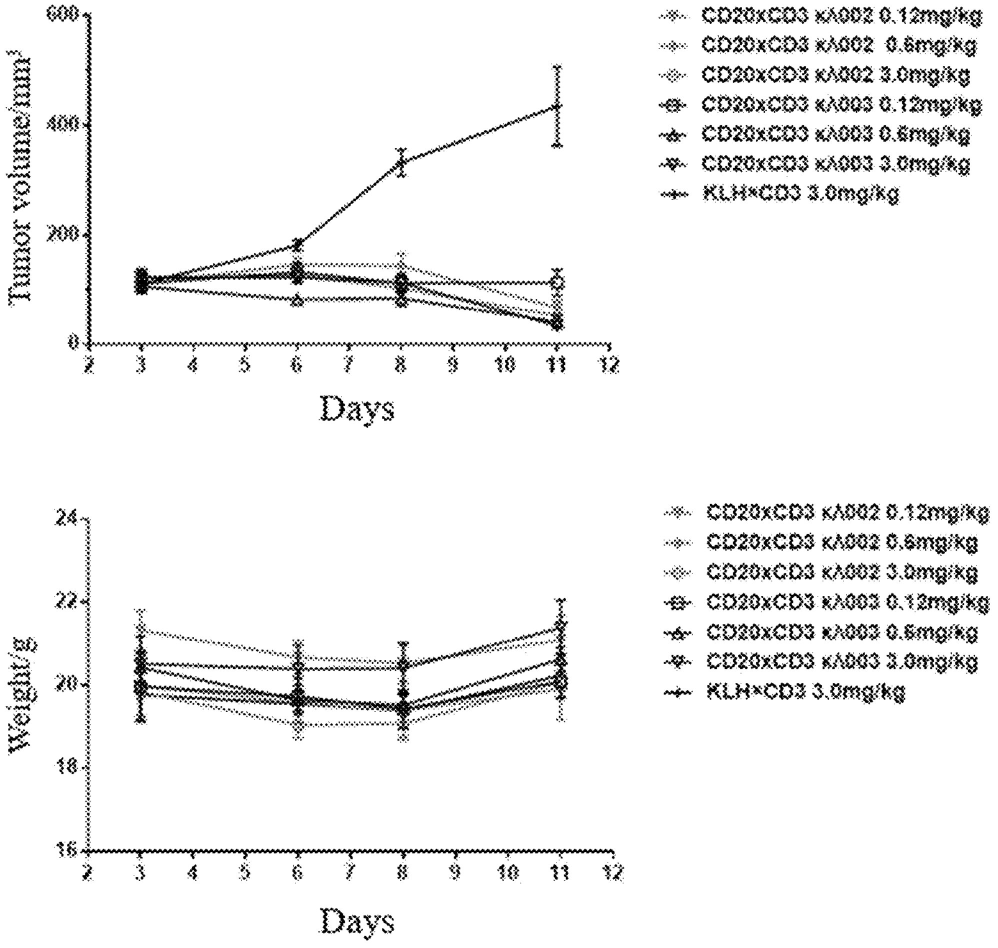

Results are shown in FIG. 29, the in vivo efficacy of the CD20×CD3 κλ bispecific antibody is dose-dependent, the tumor inhibition rates of low, medium and high doses are 65%, 98% and 162%, respectively, and the tumors in the high and medium dose groups are completely inhibited or regressed.

Example 13 Efficacy of CD20×CD3 κλ Bispecific Antibody in Cynomolgus Monkeys

Figure 30:
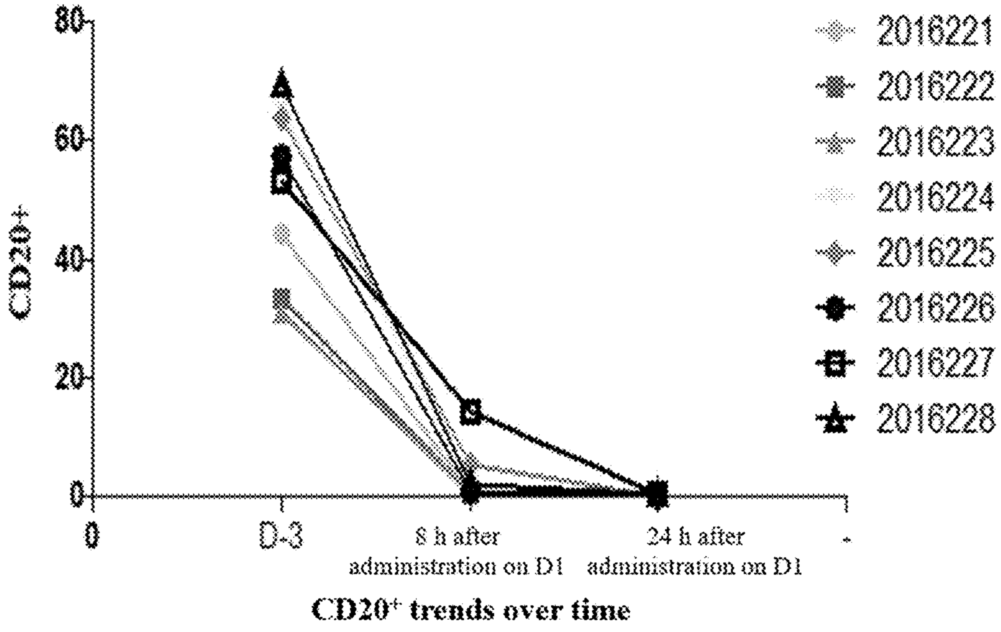
FIG. 30 shows that cynomolgus monkey B cells are quickly eliminated after administration of a CD20×CD3 κλ bispecific antibody.

8 Cynomolgus monkeys were divided into 4 dose groups, 2 monkeys per dose group, half male and half female. Doses of CD20×CD3 κλ002 bispecific antibody that were administered to the dose groups were 0.3 mg/kg, 1 mg/kg, 3 mg/kg (once a week for 3 weeks, 4 times), and 1 mg/kg (single administration). A dosing regimen is shown in Table 15. During the administration period and the recovery period, all the monkeys in each group were in good general condition, without toxic reactions, death or near-death. There is no obvious abnormal change in body temperature in each dose group, and the waveform of lead II electrocardiogram is normal. There are no obvious abnormalities in indicators such as heart rate, R-R interval, P-R interval, QT interval, QRS duration, systolic blood pressure, and diastolic blood pressure. At different time points after administration, changes in the number of B and T cell colonies in peripheral blood were analyzed by flow cytometry. B cells were identified with cell surface marker CD20 (CD20+ cells), and T cells were identified with CD3 (CD3+ cells). 8 hours after administration, B cells in peripheral blood were quickly eliminated, and 24 hours after administration, the number of B cells was less than the lower limit of detection (see FIG. 30).

TABLE 15

Dosing regimen of CD20 × CD3 κλ bispecific antibodies

| Group | Dose | Administration route and frequency | Sex | Animal No. |
|---|---|---|---|---|
| Low-dose group | 0.3 mg/kg | IV, once a week/3 weeks D 1, D 8, D 15, and D 22 | Male<br>Female | 2016221<br>2016222 |
| Medium-dose group | 1 mg/kg | IV, once a week/3 weeks D 1, D 8, D 15, and D 22 | Male<br>Female | 2016223<br>2016224 |
| High-dose group | 3 mg/kg | IV, once a week/3 weeks D 1, D 8, D 15, and D 22 | Male<br>Female | 2016225<br>2016226 |
| Medium-dose group | 1 mg/kg | IV, D 1 single administration | Female<br>Male | 2016227<br>2016228 |

The invention claimed is:

1. A bispecific antibody or an antigen-binding portion thereof, comprising: (a) a first binding domain that binds to CD20 on a surface of a target cell, the first binding domain comprising: (i) a first light chain, and (ii) a first heavy chain; wherein the first light chain comprises complementarity-determining regions (CDRs) CDR1, CDR2, and CDR3 comprising the amino acid sequence of SEQ ID NOs: 61, 62, and 63, respectively, and wherein the first heavy chain comprises CDRs CDR1, CDR2, and CDR3 comprising the amino acid sequence of SEQ ID NOs: 76, 77, and 85, respectively; and (b) a second binding domain that binds to CD3 on a surface of a T cell, the second binding domain comprising: (iii) a second light chain; and (iv) a second heavy chain; wherein the second light chain comprises complementarity-determining regions (CDRs) CDR1, CDR2, and CDR3 comprising the amino acid sequence of SEQ ID NOs: 7, 8, and 21, respectively, and wherein the second heavy chain comprises CDRs CDR1, CDR2, and CDR3 comprising the amino acid sequence of SEQ ID NOs: 26, 27, and 28, respectively.

2. The bispecific antibody or the antigen-binding portion thereof according to claim 1, wherein the first binding domain comprises:
- (a) a first light chain variable region comprising the amino acid sequence of SEQ ID NO: 59; and
- (b) a first heavy chain variable region comprising the amino acid sequence of SEQ ID NO: 83.

3. The bispecific antibody or the antigen-binding portion thereof according to claim 1, wherein the second binding domain comprises:
- (a) a second light chain variable region comprising the amino acid sequence of SEQ ID NO: 18; and
- (b) a second heavy chain variable region comprising the amino acid sequence of SEQ ID NO: 50.

4. The bispecific antibody or the antigen-binding portion thereof according to claim 1, wherein the first binding domain comprises:
- (a) a light chain comprising the amino acid sequence of SEQ ID NO: 100, and
- (b) a heavy chain comprising the amino acid sequence of SEQ ID NO: 98.

5. The bispecific antibody or the antigen-binding portion thereof according to claim 1, wherein the second binding domain comprises:
- (a) a light chain comprising the amino acid sequence of SEQ ID NO: 90; and
- (b) a heavy chain comprising the amino acid sequence of SEQ ID NO: 92.

6. A composition comprising the bispecific antibody or the antigen-binding portion thereof according to claim 1.

7. A kit comprising the bispecific antibody or the antigen-binding portion thereof according to claim 1.

8. The bispecific antibody or the antigen-binding portion thereof according to claim 1, wherein the first binding domain comprises:
- (a) a first light chain variable region comprising the amino acid sequence of SEQ ID NO: 59; and
- (b) a first heavy chain variable region comprising the amino acid sequence of SEQ ID NO: 83; and wherein the second binding domain comprises:
- (a) a second light chain variable region comprising the amino acid sequence of SEQ ID NO: 18; and
- (b) a second heavy chain variable region comprising the amino acid sequence of SEQ ID NO: 50.

9. The bispecific antibody or the antigen-binding portion thereof according to claim 1, wherein the first binding domain comprises:
- (a) a light chain comprising the amino acid sequence of SEQ ID NO: 100, and
- (b) a heavy chain comprising the amino acid sequence of SEQ ID NO: 98; and wherein the second binding domain comprises:
- (c) a light chain comprising the amino acid sequence of SEQ ID NO: 90, and
- (d) a heavy chain comprising the amino acid sequence of SEQ ID NO: 92.

10. The bispecific antibody or the antigen-binding portion thereof according to claim 1, wherein the first binding domain comprises:
- (a) a first light chain variable region comprising the amino acid sequence of SEQ ID NO: 59 with a Gln to Lys substitution at position 38 of SEQ ID NO:59; and
- (b) a first heavy chain variable region comprising the amino acid sequence of SEQ ID NO: 83 with a Gln to Glu substitution at position 39 of SEQ ID NO:83.

11. The bispecific antibody or antigen-binding portion thereof according to claim 1, wherein the first binding domain comprises:

(a) a light chain comprising the amino acid sequence of SEQ ID NO: 110, and (b) a heavy chain comprising the amino acid sequence of SEQ ID NO: 112.

12. The bispecific antibody or the antigen-binding portion thereof according to claim 1, wherein the second binding domain comprises:

(a) a light chain comprising the amino acid sequence of SEQ ID NO: 114; and (b) a heavy chain comprising the amino acid sequence of SEQ ID NO: 116.

13. The bispecific antibody or the antigen-binding portion thereof according to claim 1, wherein the first binding domain comprises:

(a) a first light chain variable region comprising the amino acid sequence of SEQ ID NO: 59 with a Gln to Lys substitution at position 38 of SEQ ID NO:59; and (b) a first heavy chain variable region comprising the amino acid sequence of SEQ ID NO: 83 with a Gln to Glu substitution at position 39 of SEQ ID NO:83; and wherein the second binding domain comprises:

(a) a second light chain variable region comprising the amino acid sequence of SEQ ID NO: 18; and (b) a second heavy chain variable region comprising the amino acid sequence of SEQ ID NO: 50.

14. The bispecific antibody or the antigen-binding portion thereof according to claim 1, wherein the first binding domain comprises:

(a) a light chain comprising the amino acid sequence of SEQ ID NO: 110, and (b) a heavy chain comprising the amino acid sequence of SEQ ID NO: 112; and wherein the second binding domain comprises:

(c) a light chain comprising the amino acid sequence of SEQ ID NO: 114, and (d) a heavy chain comprising the amino acid sequence of SEQ ID NO: 116.

* * * * *